United States Patent
Hills et al.

(10) Patent No.: US 6,549,007 B1
(45) Date of Patent: *Apr. 15, 2003

(54) ON-LINE NMR IMAGING OF A SOLID OR LIQUID OBJECT UNDERGOING CONTINUOUS TRANSLATIONAL MOTION

(75) Inventors: Brian Philip Hills, Norwich (GB); Kevin Michael Wright, Norwich (GB)

(73) Assignee: Institute of Food Research, Norwich (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/600,773

(22) PCT Filed: Jan. 21, 1999

(86) PCT No.: PCT/GB99/00210

§ 371 (c)(1),
(2), (4) Date: Sep. 11, 2000

(87) PCT Pub. No.: WO99/38026

PCT Pub. Date: Jul. 29, 1999

(30) Foreign Application Priority Data

Jan. 23, 1998 (GB) .............................. 9801622

(51) Int. Cl.[7] .................................. G01V 3/00
(52) U.S. Cl. .................. 324/306; 324/303; 324/318
(58) Field of Search ................. 324/303, 306, 324/307, 309, 318, 322, 314, 315, 300

(56) References Cited

U.S. PATENT DOCUMENTS

| | | | |
|---|---|---|---|
| 4,424,484 A | 1/1984 | Lauffer | 324/307 |
| 4,616,180 A | * 10/1986 | Compton | 324/309 |
| 4,617,516 A | 10/1986 | Schenck | 324/318 |
| 5,343,148 A | 8/1994 | Westphal | 324/309 |
| 5,532,593 A | 7/1996 | Maneval et al. | 324/306 |
| 5,602,477 A | 2/1997 | McCarthy et al. | 324/315 |
| 5,684,399 A | * 11/1997 | Bayer | 324/306 |
| 6,268,727 B1 | * 7/2001 | King et al. | 324/306 |

FOREIGN PATENT DOCUMENTS

EP    0726 458 A    * 8/1996

OTHER PUBLICATIONS

S. Lee, U.S. pat. No. 5,752,901, May 19, 1998, abstract.
Y. Kim, et al., U.S. pat. No. 5,650,986, Jul. 22, 1997, abstract.
A.P. Gusenkov, et al., pat. No. RU2,042,443, Aug. 27, 1995, abstract.
Y.H. Lee, U.S. pat. No. 5,453,305, Sep. 26, 1995, abstract.
S.C. Jacobsen, et al., pat. No. EP–490,666, Jun. 17, 1992, abstract; U.S. pat. No. 5,197,044, Mar. 23, 1993, abstract; U.S. pat. No. 5,440,526, Aug. 8, 1995, abstract.
E.B. Boskamp, et al., U.S. pat. No. 5,030,915, Jul. 9, 1991, abstract; pat. No. EP–443,677, Aug. 28, 1991, abstract.
R.C. Lee, et al., pat. No. EP–334,608, Sep. 27, 1989, abstract; U.S. pat. No. 4,938,473, Jul. 3, 1990, abstract.
Tellier, Charles "On–Line Applications in Food Science" pp. 105–122 1990 Reference No. XP 002105195.

(List continued on next page.)

Primary Examiner—Edward Lefkowitz
Assistant Examiner—Tiffany A. Fetzner
(74) Attorney, Agent, or Firm—Dickstein Shapiro Morin & Oshinsky LLP

(57) ABSTRACT

A nuclear magnetic resonance imaging technique is applied to objects undergoing translational motion for analysis of objects on a conveyor passing through an imaging unit. The objects are passed through the imaging module at a predetermined velocity (v), in which there is provided: a spatially uniform, constant magnetic field ($B_0$) substantially parallel to the direction of the velocity (v); a linear magnetic field gradient ($G_z$) substantially parallel to the direction of the velocity (v); and a radiofrequency field ($B_z$) pulse transverse to field $B_0$. Selected nuclear magnetic resonance parameters from said objects are then detected for subsequent imaging and analysis.

41 Claims, 48 Drawing Sheets

OTHER PUBLICATIONS

J.S. Best, et al., pat. No. EP–111,755 A, Jun. 27, 1984, abstract; pat. No. EP–111,755B, Aug. 2, 1989, abstract; U.S. pat. No. 4,547,824, Oct. 15, 1985, abstract.

Raymond Lee Organization, pat. No. CH–568,172, Oct. 31, 1975, abstract.

G. Laukien, et al., U.S. pat. No. 5, 545,997, Aug. 13, 1996, abstract.

M. Westphal, pat. No. GB2,296,329, Jun. 26, 1996, abstract; U.S. pat. No. 5,666,054, Sep. 9, 1997, abstract.

R. M. Bentley, et al., U.S. 5,473,221, Dec. 5, 1995, abstract.

M. Westphal, pat. No. GB2,290,386, Dec. 20, 1995, abstract; pat. No. DE4,421,335, Dec. 21, 1995, abstract; pat. No. GB2,290,386, May 6, 1998, abstract; U.S. pat. No. 5,563,567, Oct. 8, 1996, abstract.

G. Laukien, et al., pat. No. DE4,416,907, Sep. 7, 1995, abstract; pat. No. GB2,289,343, Nov. 15, 1995, abstract; U.S. pat. No. 5,485,088, Jan. 16, 1996, abstract.

A. Maillot, et al. pat. No. EP–612095, Aug. 24, 1994, abstract; pat. No. EP–612095, Jun. 4, 1997, abstract; U.S. pat. No. 5,408,159, Apr. 18, 1995, abstract.

T. Kawaguchi, et al., pat. No. DE4,335,807, Apr. 28, 1994, abstract; U.S. pat. No. 5,625,331, Apr. 29, 1997, abstract.

D.J. Schaefer, U.S. pat. No. 5,293,126, Mar. 18, 1994, abstract; pat. No. EP–620922, Oct. 26, 1994, abstract.

B. Defontaine, pat. No. WO9,317,487, Sep. 2, 1993, abstract; pat. No. EP–628225, Dec. 14, 1994, abstract; U.S. pat. No. 5,606,205, Feb. 25, 1997, abstract.

V.V. Skvortsov, et al., pat. No. SU1,261,427, Feb. 7, 1992, abstract.

Z. Jajtic, et al., pat. No. DE4,125,779, Dec. 17, 1992, abstract.

T. Oue, et al., pat. No. DE4,136,834, May 14, 1992, abstract; pat. No. GB2,252,168, Jul. 29, 1992, abstract; U.S. pat. No. 5,343,183, Aug. 30, 1994, abstract.

Anonymous, pat. No. RD–327095, Jul. 10, 1991, abstract.

D.B. Cruickshan, et al., pat. No. GB2,235,339, Feb. 27, 1991, abstract; pat. No. GB2,235,339, Feb. 9, 1994, abstract.

A. Kasten, et al., pat. No. DE3,914,243, Oct. 31, 1990, abstract; pat. No. DE3,914,243, Jun. 9, 1993, abstract; pat. No. EP–470095, Mar. 16, 1994, abstract; U.S. pat. No. 5,276,399, Jan. 4, 1994, abstract.

G. Laukien, et al., pat. No. DE3,907,927, Sep. 20, 1990, abstract; pat. No. DE3,907,927, Jun. 9, 1993, abstract; pat. No. EP–462131, Oct. 27, 1993, abstract; U.S. pat. No. 5,168,211, Dec. 1, 1992, abstract.

J.T. Dibene, et al., pat. No. WO9006574, Jun. 14, 1990, abstract; pat. No. EP–446277, Sep. 18, 1991, abstract; U.S. pat. No. 4,945,434, Jul. 31, 1990, abstract.

W.F. Hannan, U.S. pat. No. 4,935,650, Jun. 19, 1990, abstract.

J. Bergstroem, et al., pat. No. SE–459378, Jun. 26, 1989, abstract; pat. No. EP–424402, May 2, 1991, abstract; U.S. pat. No. 5,300,861, Apr. 5, 1994, abstract.

D. Even, pat. No. EP–331559, Sep. 6, 1989, abstract; pat. No. EP–331559, May 29, 1991, abstract; U.S. pat. No. 4,864,173, Sep. 5, 1989, abstract.

J. Couvreur, et al., pat. No. GB2,207,004, Jan. 18, 1989, abstract, pat. No. DE3,823,493, Jan. 26, 1989, abstract; pat. No. GB2,207,004, Jan. 18, 1989, abstract; U.S. pat. No. 4,843,361, Jun. 27, 1989, abstract.

J.W. Carlson, U.S. pat. No. 4,755,755, Jul. 5, 1988, abstract; pat. No. GB2,202,793, Aug. 15, 1990, abstract.

G. Mesenich, et al., pat. No. GB2,199,698, Jul. 13, 1988, abstract; pat. No. GB2,199,698, Jun. 19, 1991, abstract; U.S. pat. No. 4,840,163, Jun. 20, 1989, abstract.

M. Kazuki, pat. No. WO8,607,459 Dec. 18, 1986, abstract; pat. No. EP–225390, Jan. 30, 1991, abstract; U.S. pat. No. 4,774,486, Sep. 27, 1988, abstract.

G.N. Kovshov, et al., pat. No. SU1,199,917, Dec. 23, 1985, abstract.

G. Aubert, pat. No. WO8,603,882, Jul. 3, 1986, abstract; U.S. pat. No. 4,748,429, May 31, 1988, abstract.

N. Krause, pat. No. DE3,340,384, May 15, 1985, abstract; pat. No. EP–142077, May 22, 1985, abstract; U.S. pat. No. 4,592,363, Jun. 3, 1986, abstract.

D. Tronc, et al., pat. No. FR2,551,258, Mar. 1, 1985, abstract.

D.N. Harrison, et al., pat. No. ZA8,304,339, Jan. 24, 1984, abstract; U.S. pat. No. 4,517,846, May 21, 1985, abstract.

J. Knaak, pat. No. DE3,244,473, Jun. 7, 1984, abstract; pat. No. EP–111187, Jun. 2, 1984, abstract; U.S. pat. No. 4,522,073, Jun. 11, 1985.

P. Vandijk, pat. No. EP–105550, Apr. 18, 1984, abstract; pat. No. EP–105550, Dec. 17, 1986, absract; U.S. pat. No. 4,564,812, Jan. 14, 1986, abstract.

K.W. McGlashan, U.S. pat. No. 4,429,293, Jan. 31, 1984, abstract; pat. No. DE3,417,392, Nov. 15, 1984, abstract; pat. No. GB2,140,200, Nov. 21, 1984, abstract.

M. Fujimoto, et al., pat. No. EP—74085, Mar. 16, 1983, abstract; pat. No. EP—74085, Jul. 8, 1987, abstract; U.S. pat. No. 4,481,824, Nov. 13, 1984, abstract.

H. Linn, pat. No. DE3,120,607, Nov. 4, 1982, abstract; U.S. pat. No. 4,568,809, Feb. 4, 1986, absract.

I.R. Kirillov, et al., pat. No. SU–782690, Jan. 23, 1982, abstract.

H. R. Jory, et al., pat. No. GB2,094,546, Sep. 15, 1982, abstract; pat. No. DE3,208,293, Sep. 23, 1982, abstract; pat. No. GB2,094,546, Nov. 14, 1984, abstract.

O.S. Rafikov, et al., pat. No. SU–798387, Jan. 26, 1981, abstract.

J. Gross, et al., pat. No. BE–888808, Aug. 28, 1981, abstract; pat. No. DE3,118,998, Mar. 11, 1982, abstract.

V.G. Mikhailovs, et al., pat. No. SU–656384, May 25, 1981, abstract.

H. Gerken, et al., pat. No. DE2,935,939, Mar. 26, 1981, abstract; pat. No. DE2,935,939, Dec. 28, 1989, abstract.

R.F. Schmoock, U.S. pat. No. 4,253,340, Mar. 3, 1981, abstract; pat. No. DE3,006,723, Apr. 2, 1981, abstract; pat. No. GB2,059,066, Apr. 15, 1981, abstract.

V.V. Permyakov, et al., pat. No. SU–734818, May 26, 1980, abstract.

G.I. Kovshov, et al., pat. No. SU–678183, Aug. 8, 1979, abstract.

S. Kofink, pat. No. DE2,903,817, Aug. 8, 1980, abstract.

W. Kiene, et al., pat. No. DE2,743,954, Apr. 12, 1979, abstract.

Pat. No. FR2,129,863, abstract.

U.S. pat. No. 3,663,361, abstract.

\* cited by examiner

ON-LINE NMR IMAGING OF A SOLID OR LIQUID OBJECT UNDERGOING CONTINUOUS TRANSLATIONAL MOTION

The present invention relates to nuclear magnetic resonance phenomena and in particular to the use thereof in imaging and analysis techniques.

This present application describes the development of a low-cost, robust, and fast, on-line nuclear magnetic resonance (NMR) imager (and associated protocols) suitable for imaging a solid object undergoing continuous translational motion. To date, conventional NMR and MRI measurements on solid objects are performed when they are stationary. This prevents the application of NMR imaging methods to objects moving continuously on conveyor belts, or to semi-solid materials being extruded or otherwise ejected. This severely limits the development of MRI as a sensor in an on-line industrial process. In contrast, the NMR techniques and protocols described in this specification are specifically designed to apply to objects in motion and do not succeed unless the object is translating. This distinguishes the present application from previous NMR and MRI approaches.

Conventional MRI velocity measurements on flowing fluids are a possible exception to the statement that conventional NMR methods are performed only on stationary objects. However the protocols used to image fluid flow are not applicable to solid objects moving with constant velocity. In contrast, the techniques described in the present specification can be applied both to solid translating objects and also to flowing fluids.

An on-line imaging technique which is fast, low-cost, robust and fully automated is important in a number of commercial environments. Some conventional MRI techniques, such as echo planar imaging (EPI), are "fast", with image acquisition times of 100 milliseconds or less, but they require expensive equipment, such as rapidly switched (500 to 2000 Hz), low inductance, strong (10–40 mT m$^{-1}$) gradient generating units, and are not suitable for application in a factory environment and cannot easily be automated. Moreover, motion of an object being imaged during the EPI acquisition time has an adverse effect on EPI image quality. For example, an object of size 5 cm, moving with a velocity of 1 m/s would move its own length (5 cm) if the EPI image acquisition time is 50 ms. In contrast the present specification shows that object motion is essential to the success of the present invention and does not degrade image quality. Moreover the hardware is low cost (relative to today's commercial NMR spectrometers), robust, and can be fully automated.

The present invention exploits a fundamental physical principle of motional relativity, namely, that a time varying magnetic field (or time-varying field gradient) can be applied to an object in either of two equivalent ways. In the first, conventional, way, the object is stationary and the magnetic field is varied in time. In the second way, exploited by the present invention, the magnetic field (or field gradient) is steady, and instead, the object is moved through the field (or field gradient). The latter way has not, hitherto, been exploited for on-line magnetic resonance imaging.

It is an object of the present invention to provide a method for obtaining magnetic resonance imaging data in respect of an object which is undergoing translational motion.

It is a further object of the present invention to provide apparatus for gathering magnetic resonance imaging data on objects passing therethrough.

It is a further object of the invention to provide a method and apparatus for real time monitoring of objects passing through an imaging unit using magnetic resonance imaging techniques.

According to one aspect, the present invention provides a method of nuclear magnetic resonance imaging comprising the steps of:
   conveying an object to be imaged through an imaging module at predetermined velocity, v;
   generating, within the imaging module, a spatially characterised, constant magnetic field $B_0$ substantially parallel to the direction of the velocity, v;
   generating, within the imaging module, a spatially characterised magnetic field gradient, $G_z$ substantially parallel to the direction of the velocity, v;
   generating, within the imaging module, a radiofrequency field $B_1$ pulse transverse to field $B_0$;
   detecting nuclear magnetic resonance signals weighted with at least one selected nuclear magnetic resonance parameter from said object.

According to another aspect, the present invention provides an apparatus for gathering nuclear magnetic resonance imaging data comprising:
   a first field generating means for generating a spatially characterised, constant magnetic field $B_0$ in an imaging unit volume having a predetermined length along a longitudinal axis thereof, the $B_0$ field being parallel to said longitudinal axis;
   a second field generating means for generating, in said imaging unit volume, a spatially characterised magnetic field gradient $G_z$ substantially parallel to $B_0$;
   a third field generating means for generating, within the imaging unit volume, radiofrequency field $B_1$ pulses transverse to field $B_0$;
   receiver means for detecting nuclear magnetic resonance signals weighted with at least one selected nuclear magnetic resonance parameter from said object;
   wherein at least said second field generating means comprises a coil having cylindrical geometry.

According to a further aspect, the present invention provides an apparatus for gathering nuclear magnetic resonance imaging data comprising:
   a first field generating means for generating a spatially characterised, constant magnetic field $B_0$ in an imaging unit volume having a predetermined length along a longitudinal axis thereof, the $B_0$ field being parallel to said longitudinal axis;
   a second field generating means for generating, in said imaging unit volume, a spatially characterised magnetic field gradient $G_z$ substantially parallel to $B_0$;
   a third field generating means for generating, within the imaging unit volume, radiofrequency field $B_1$ pulses transverse to field $B_0$;
   receiver means for detecting nuclear magnetic resonance signals weighted with at least one selected nuclear magnetic resonance parameter from said object;
   wherein at least said second field generating means comprises a coil having adjacent loops thereof separated by a distance which increases or decreases as a function of the distance along the coil axis.

Embodiments of the present invention will now be described, by way of example, and with reference to the accompanying drawings in which:

FIGS. 17 to 24 show the results of converting a motionally modified free induction decay signal into an image projection in which FIG. 17 shows the signal intensity values of the original profile;

FIG. 18 shows the signal intensity values of a transformed echo with no phase error;

FIG. 19 shows the signal intensity values of a transformed echo with phase error;

FIG. 20 shows the signal intensity values of a transformed second half of an echo with no phase error;

FIG. 21 shows the sign intensity values of a transformed second half of an echo with phase error;

FIG. 22 shows the signal intensity values of a transformed symmetrized echo with no phase error;

FIG. 23 shows the signal intensity values of a transformed symmetrized echo with phase error;

FIG. 24 shows the signal intensity values of a transformed symmetrized echo with phase correction;

Figure 47:
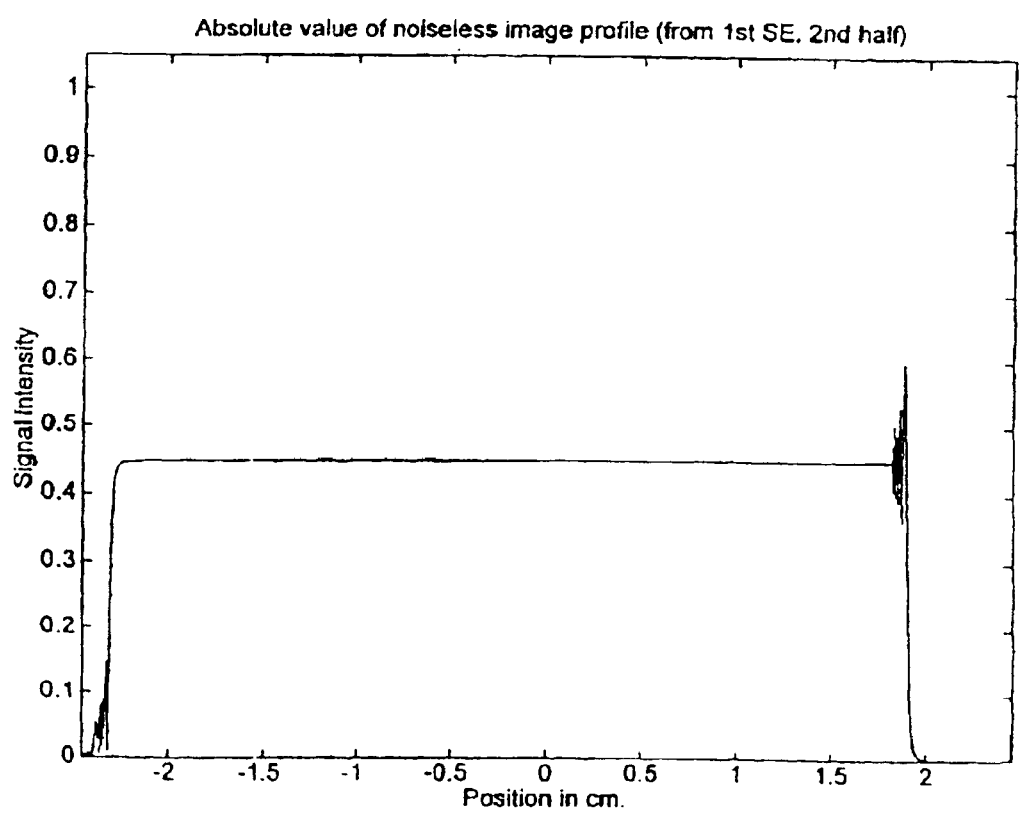
Figure 48:
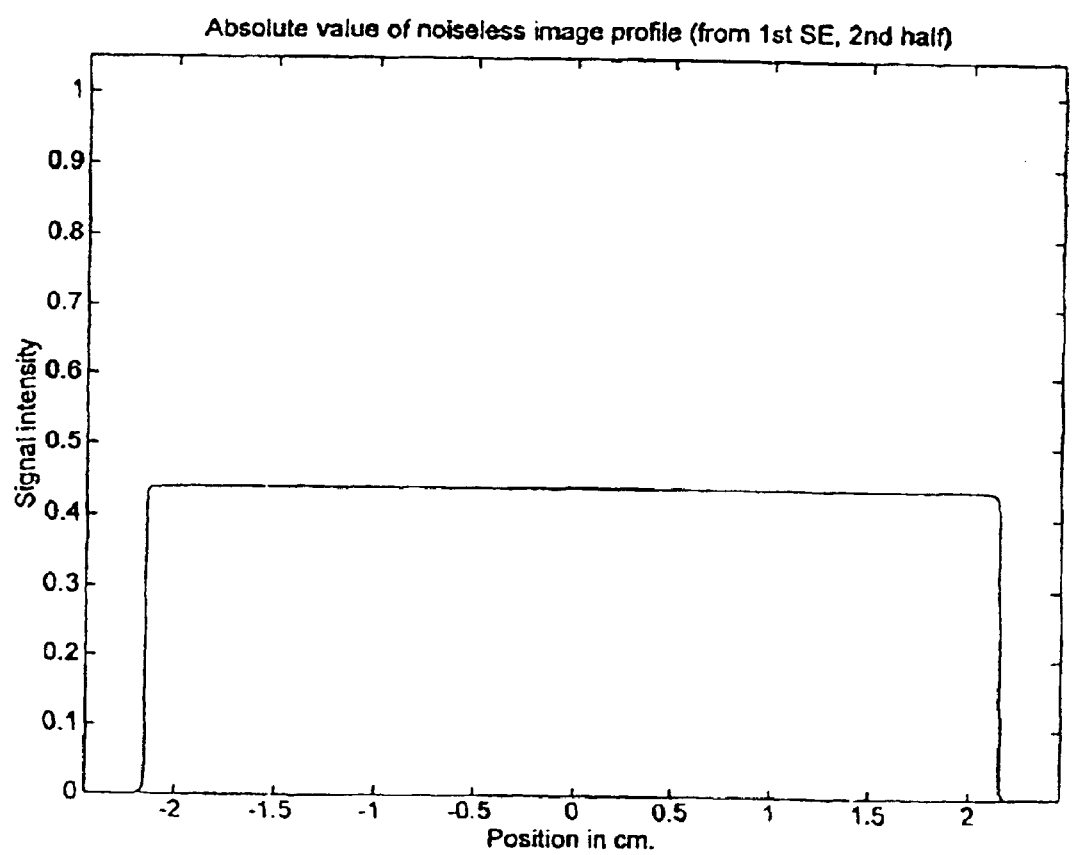

FIG. 47 shows the distortion in the output as a function of z derived from transforming the first motionally modified spin echo in a Hahn spin echo sequence, from a rectangular object, where the gradient field deviates from the ideal value by −2%; and FIG. 48 shows an undistorted output as a function of z derived from transforming the first motionally modified spin echo in a Hahn spin echo sequence, from a rectangular object where the gradient field is at the ideal value.

a) Motionally Modified Free Induction Decays (MMFID's) and Motionally Modified Spin-echoes (MMSE's)

The present invention exploits what can be called "motionally modified free induction decays" (MMFID's), and motionally modified spin echoes (MMSE's). We therefore begin with a description of how an MMFID and an MMSE are formed and how they can be exploited for on-line imaging.

Consider a solid object moving in a straight line with uniform velocity v. Preferably, the first step in the on-line method is to induce longitudinal magnetisation $M_z$ in the object in the same direction as the velocity vector v. The second step involves acquiring the Free Induction Decay (FID) by irradiating with a hard 90°, on-resonance, radiofrequency pulse in a static, homogeneous magnetic field $B_0$, oriented parallel to the velocity vector v, and in the presence of a linear magnetic field gradient $G_z$ also oriented parallel to $B_0$ and v. Then the FID will be modulated by the motion and attenuated by transverse relaxation $T_2^*$.

The existence of MMFID's can be demonstrated both using analytic mathematical methods (as described in greater detail in Appendix 1) and by computer simulation (as described in greater detail in Appendix 2, where a novel computer algorithm is presented for extracting an image projection from the motionally-modified FID).

The existence of MMSE's can also be demonstrated using analytic mathematical methods (as described in greater detail in Appendix 3) and by computer simulation (as described in greater detail in Appendix 4). An MMSE is created with the spin echo pulse sequence 90-τ-180-τ-MMSE, when the object to be imaged is moving with constant velocity v in the presence of a constant, linear field gradient $G_z$ oriented parallel to v. In Appendix 3 it is shown that, contrary to the conventional spin-echo sequence, there is no spin echo for an arbitrary pulse spacing τ because of destructive dephasing by motion through the field gradient. However, provided the pulse spacing τ is set equal to a multiple of the acquisition time AQ a motionally modified spin echo (MMSE) can be formed. Setting τ equal to AQ is a necessary, but not a sufficient condition for formation of MMSE's. The dwell time and gradient also need matching with a sample velocity and sample length. The method for doing this is explained in Appendix 8. Clearly, a train of MMSE's can be created using successive 180 pulses in the sequence 90-τ-(180-τ-MMSE)$_n$ where n≧1 and τ is a multiple of AQ. Appendix 4 presents a novel computer algorithm for extracting an image from an MMSE.

b) Hardware Requirements for Creating MMFID's and MMSE's

Figure 1:
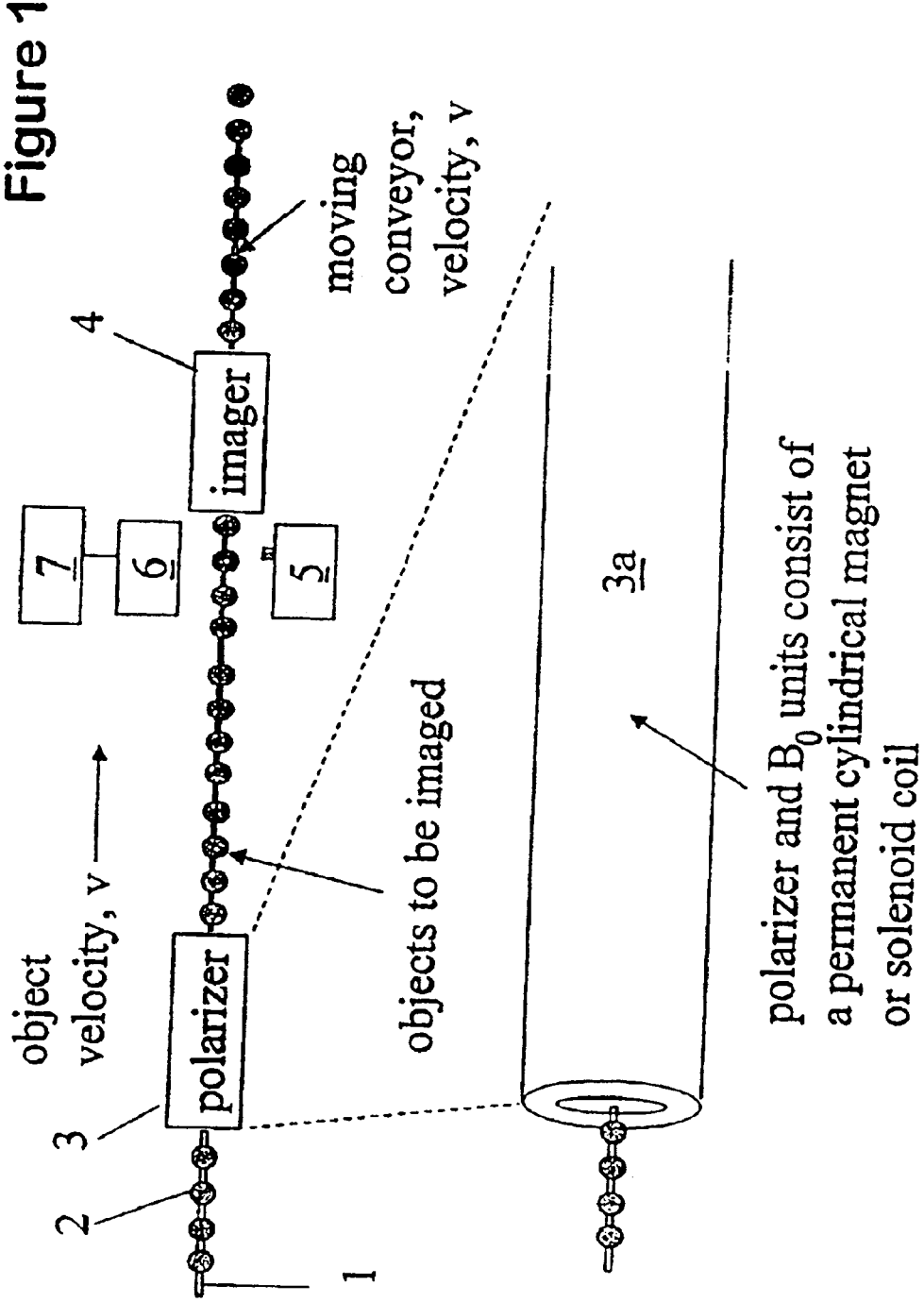
FIG. 1 shows a schematic diagram showing principles of a nuclear magnetic resonance imaging apparatus according to the present invention.

The objects to be imaged travel in a single-file manner down a conveyor tube, pneumatic tube, belt or other suitable means, schematically shown on FIG. 1 as conveyor 1. The conveyor 1 and all the objects 2 on it preferably move with a constant velocity v. Although the imaging procedure is tolerant of small vibrations of each object (see below), there should be substantially no reorientation of the objects 2 relative to the conveyor 1. In practice this can be arranged by simply holding the objects, in e.g. foam supports (not shown), along the conveyor 1.

The hardware required to create and observe motional echoes consists of separate cylindrically shaped units which enclose the conveyor and can be positioned at various positions along the conveyor. The conveyor 1 carrying the objects to be imaged then travels down the central axis of the cylindrical units, although precise lateral positioning of the objects within the cylindrical units is not essential where uniform fields across the x and y axes are used. A modular approach to the design of the hardware provides greater adaptability to a plurality of applications.

Because the object to be imaged is travelling with velocity v and it takes a finite time (at least AQ) to acquire the NMR signal(s), it is necessary that the $B_0$ field, radiofrequency field $B_1$, and gradient field $G_z$, are all spatially homogeneous over a distance of, at least v×AQ, along the conveyor.

Figure 45:
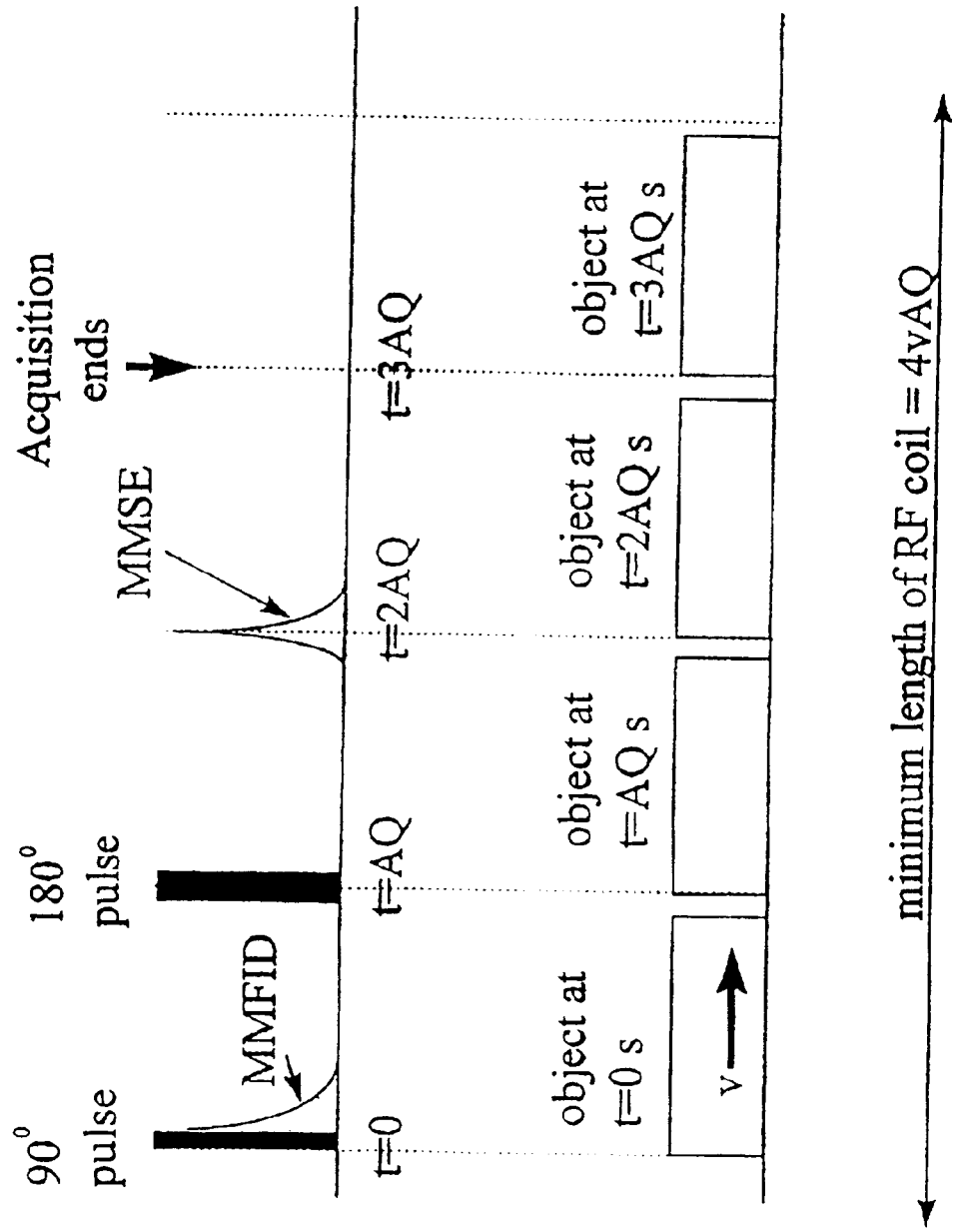
FIG. 45 shows a schematic diagram illustrating distance travelled by an object during excitation and acquisition using a Hahn echo pulse sequence.

For the Hahn echo sequence consisting of a 90 degree radiofrequency excitation pulse followed by a 180 degree pulse a time 2×AQ later, the distance travelled by the object between excitation and echo acquisition is actually 3v×AQ. This is illustrated in FIG. 45. This means that $B_0$ field, the radiofrequency field, $B_1$, and the gradient field, $G_z$, are all preferably homogeneous over a distance of at least 4v×AQ in order to encompass the whole object during its motion.

According to the preferred embodiment illustrated, the hardware devices as described below for generating the $B_0$ field, radiofrequency field $B_1$, and field gradient $G_z$ is that they are all cylindrically shaped with lengths that can be extended indefinitely, at least in principle. This distinguishes them from conventional NMR arrangements, such as U-shaped magnets, radiofrequency Helmholtz coils, birdcage coils etc. which would create homogeneous fields only over a limited distance along the conveyor.

The Polarizer Unit

We consider a solid object moving with constant velocity v. The first step in obtaining an image of the object is to induce longitudinal magnetisation within it by application of a constant external magnetic field. This is done in the polarizer unit 3 illustrated in FIG. 1. If the object has a short $T_1$, then the polarizer consists either of a single, straight, hollow, cylindrical permanent magnet 3a of length L, as shown in the FIG. 1 inset, or a solenoid coil electromagnet of length L. The object moves on the conveyor 1, preferably down the central axis inside the cylindrical polarizer. The time spent inside the polarizer is L/v and for 100% polarization it is preferred that this should be at least $5T_1$. However, 100% polarization is not an essential requirement of the on-line imager and lower degrees of polarization can be used.

If $T_1$ is long (several seconds) L may be impracticably large, in which case a series of solenoids or permanent magnets can be arranged in, for example a spiral arrangement and the conveyor passed along the spiral. Once the object is sufficiently polarized it passes, with velocity v, into the imaging module which creates MMFID's.

The Imaging Module

Depending on the application, an imaging module 4 consists of some or all of five different hardware units. These are called the $B_0$ unit; the RF unit; the $G_z$ unit; the $G_x$ unit; and the $G_\phi$ unit respectively. To create MMFID's or MMSE's, only the three $B_0$, RF and $G_z$ units are required.

The $B_0$ Unit

The polarized object 2 emerging from the polarizer 3 on the conveyor 1 passes into a spatially uniform, constant magnetic field $B_0$ created by the $B_0$ unit within the imaging unit 4. Like the polarizer unit, the $B_0$ field can be created by a hollow cylindrical permanent magnet or by a hollow cylindrical solenoid electromagnet called, for convenience, the $B_0$ unit. The conveyor carrying the polarized objects then moves down the middle of the cylinder with uniform velocity in a direction parallel to the cylinder axis and preferably along the cylinder axis. The direction of the polarized longitudinal magnetisation in the object leaving the polarizer should be in the same direction as $B_0$ in the $B_0$ unit. The magnet can be of any desired length provided the $B_0$ field everywhere in the object is spatially uniform. if the object $T_1$ is sufficiently short then the polarizer and $B_0$ units can be combined into a single continuous unit.

The RF Unit

Figure 2:
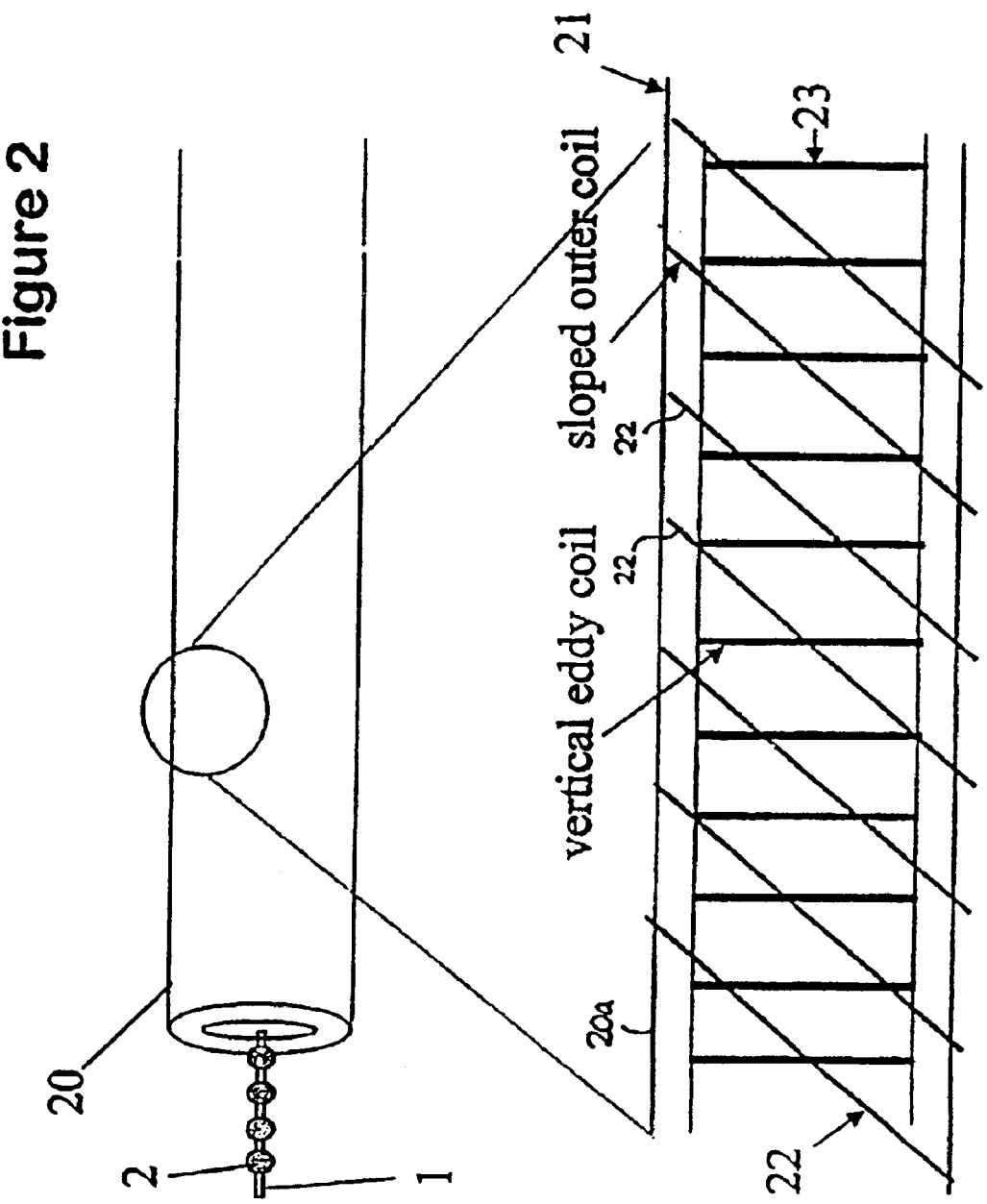
FIG. 2 shows a schematic diagram of an exemplary RF field generating unit suitable for use in the present invention.

This is illustrated in FIG. 2. The on-resonance, radiofrequency field $B_1$, which must be transverse to $B_0$, can be generated by the specially designed, cylindrical "radiofrequency solenoid-like coil" which we call the "RF unit". Preferably this also acts as a receiver coil and its particular preferred form is fully described in the reference, "A solenoid-like coil producing transverse radiofrequency fields for MR imaging"by E. K. Jeong, D. H. Kim, M. J. Kim, S. H. Lee, J. S. Suh and Y. K. Kwong in J. Magn. Reson. 127 (1997) 73–79. Article no. MN971172.

The RF unit 20 as described therein includes a pair of cylindrical coils: a first, outer coil 21 which has the plane of each loop 22 tilted with respect to the cylinder (z) axis to generate an RF field with a component perpendicular to the cylinder axis. A second, inner coil 23 acts as an eddy-current coil which eliminates the longitudinal component of the RF field, leaving an RF field entirely perpendicular to the cylinder axis.

A special characteristic of this device is the generation of a uniform radiofrequency field over a long z distance. This distinguishes it from more conventional RF generators such as the standard saddle coil, birdcage or cavity resonator. Such conventional devices could be used for the purposes of the present invention, provided they are of sufficient size that their RF field is uniform over distances exceeding the distance moved by the object during the acquisition time (3v×AQ, in a spin echo imaging experiment, where v is the velocity and AQ is the acquisition time, see FIG. 45). The solenoid-like RF unit coil 20a overcomes this limitation and can be easily situated inside and concentric with the $B_0$ unit solenoid coil or permanent magnet. The RF unit 20 is interfaced with conventional electronic equipment and computers for control, acquisition and image processing.

The $G_z$ Unit

Figure 3:
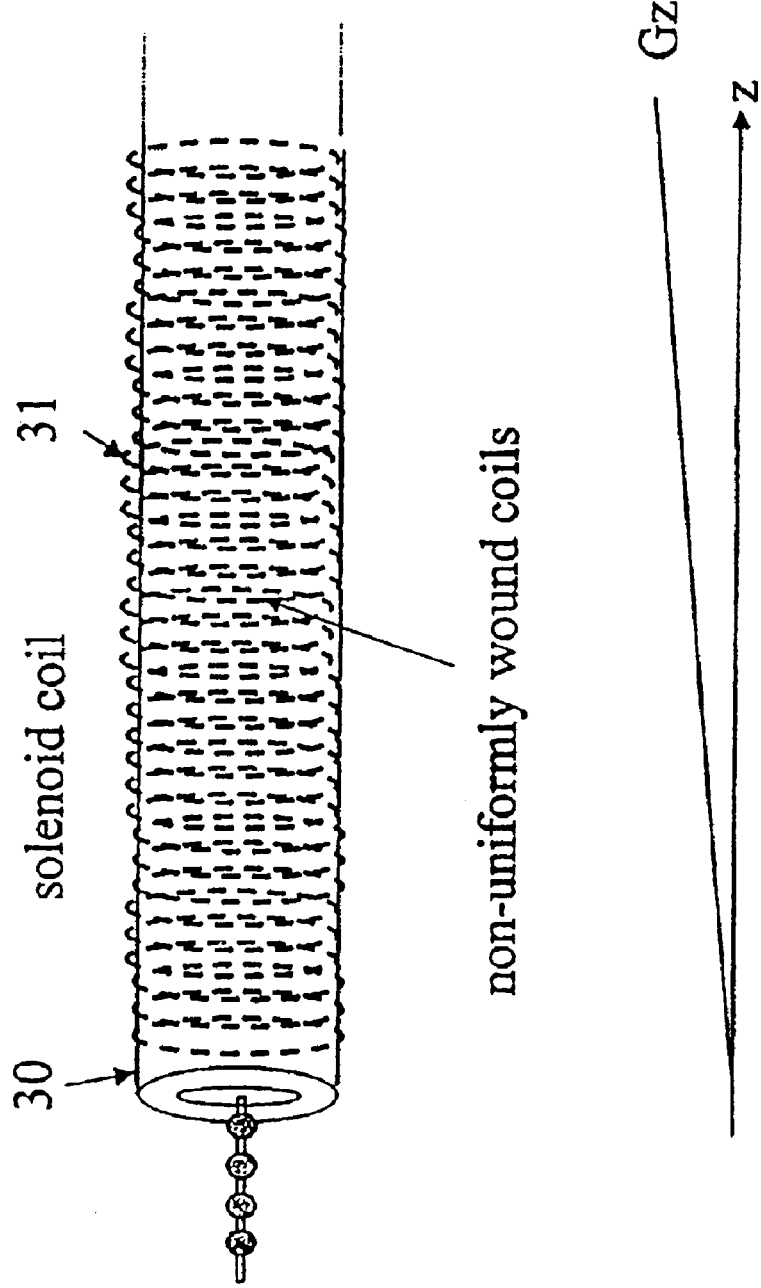
FIG. 3 shows a schematic diagram of an exemplary $G_z$ field generating unit according to the present invention.

This is illustrated in FIG. 3. The linear magnetic field gradient $G_z$ is oriented parallel to $B_0$ and the direction of object motion and is generated by the $G_z$ unit. Preferably, this comprises a specially designed, non-uniformly wound cylindrical solenoid coil 30 as shown, in which the spacing of the turns 31 of the coil 30 vary as a function of z-position. This is described more fully in Appendix 5 which includes computer calculations of the field gradient G within the unit. Note that the gradient will need to be matched to the sample velocity and other parameters, so that a suitably sized image is created. The factors determining the magnitude of the $G_z$ gradient magnitudes are detailed in Appendix 8. It may also be possible to create the extended linear $G_z$ gradient using permanent magnets.

The gradient solenoid unit 30 will be located inside and concentrically with the $B_0$ unit and around the radiofrequency solenoid-like RF unit. It can be made of any desired length, subject to a minimum length below which the gradient is no longer sufficiently uniform for undistorted image acquisition.

The $G_x$ Unit

Figure 4:
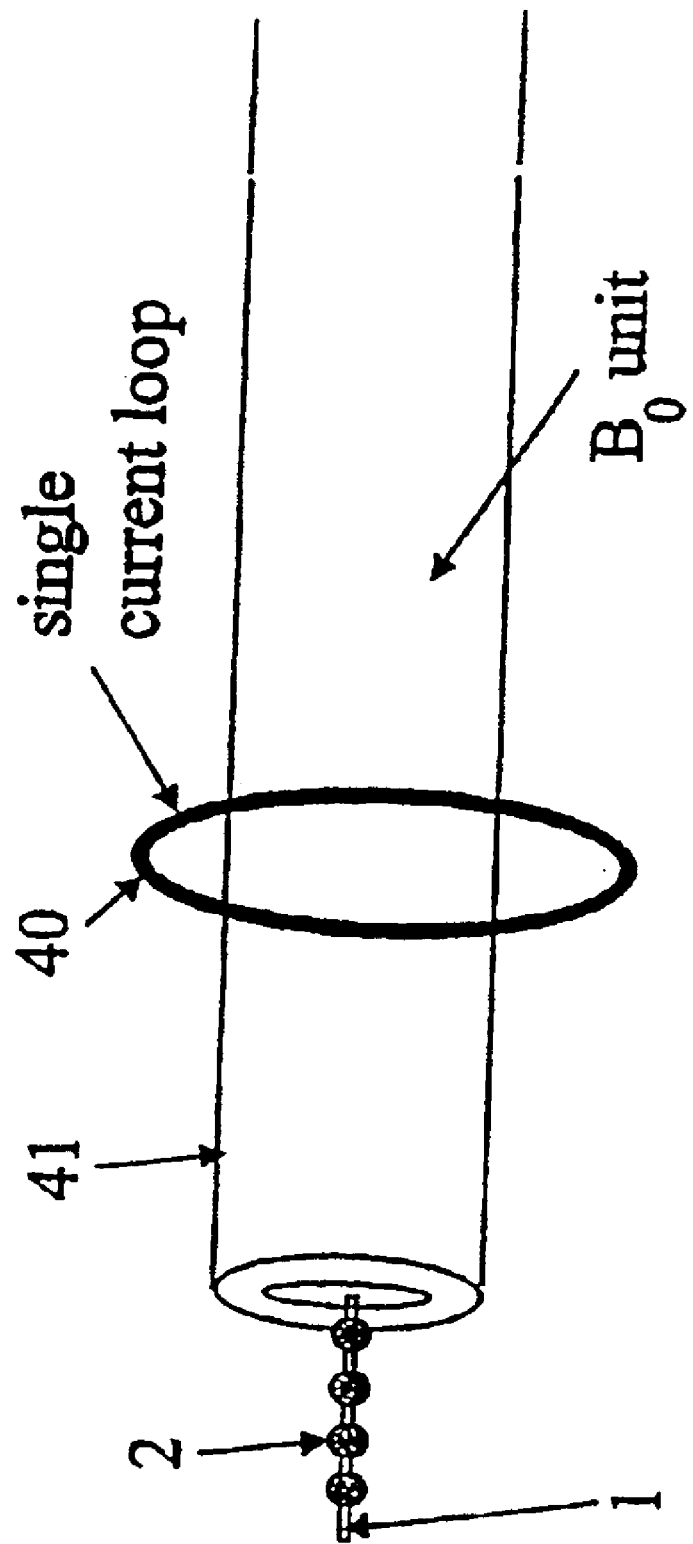
FIG. 4 shows a schematic diagram of an exemplary $G_x$ field generating unit suitable for use in the present invention.

This is illustrated schematically in FIG. 4 and the magnetic fields are simulated in Appendix 6. Where diffusion-weighted on-line imaging is required, an optional fourth type of hardware unit comprising a single electric coil 40 can be used which surrounds the $B_0$ unit 41. The $G_x$ unit creates a steady, spatially localised, non-uniform magnetic field gradient $G_x$ transverse to $B_0$. The coil 40 is wound around the gradient ($G_z$ unit 30) or RF solenoid unit 20 at a single location.

The $G_\phi$ Unit

Figure 5:
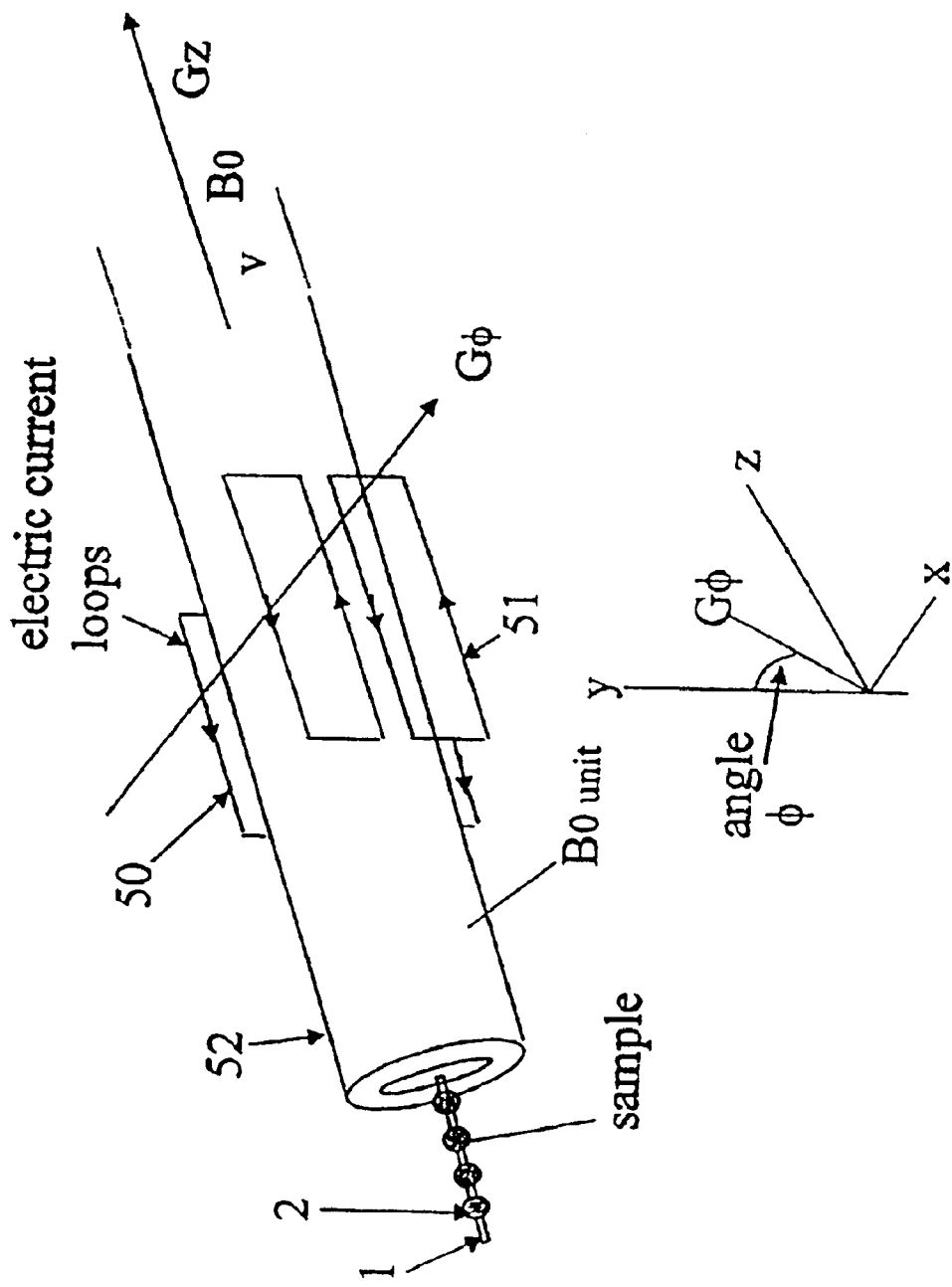
FIG. 5 shows a schematic diagram of an exemplary $G_\phi$ field generating unit suitable for use in the present invention.

With reference to FIG. 5, where 2- or 3-dimensional imaging is required (as apart from one-dimensional projection imaging along the direction of motion, z), additional linear, steady, magnetic field gradients transverse to $B_0$ can be created in a conventional way with, for example, carrying imbalanced currents coils 50, 51 placed at suitable locations around the $B_0$ unit 52 magnet. The optional additional coils needed to create these gradients, we call a $G_\phi$ unit because the field can be oriented at an angle $\phi$ to the vertical.

Triggering the NMR Pulse Sequence

This can be done electronically by arranging for the object to be imaged to cut a laser or infra-red beam traversing the conveyor as the object enters the imaging unit. This is provided by suitable conventional light source 5 and a receiver unit 6 coupled to a control circuit 7. An electronic delay then triggers the first 90° radiofrequency pulse. If two laser beams are used spaced along the conveyor, the velocity v of the object can be measured and this used to calculate the timing of the radiofrequency pulses automatically.

Minimising Eddy Currents

It is important that the units creating $B_0$, $B_1$ and the gradients do not interfere with each other via the creation of eddy currents. Eddy currents can be minimised by using a ceramic-ferrite permanent magnet for $B_0$. The solenoid-like RF unit has also been designed to minimise eddy currents (see the above reference). However, in the present invention, eddy current effects can be minimised by exploiting the motional relativity principle. Namely, the field $B_0$ and field gradients, $G_z$ (and $G_x$, see below) are preferably kept constant in time and the object to be imaged is moved instead. The obvious exception is the radiofrequency unit which must be switched to create time-varying radiofrequency pulses.

The on-line imager uses various combinations of these basic hardware units to create images of the moving object using one or more of the on-line imaging protocols listed and described below. Which combination of units is used, and their arrangement along the conveyor, will be determined by the to choice of on-line imaging protocol which, in turn, will be determined in part by the nature and velocity of the object: to be imaged and the information required.

On-line Imaging Protocols

Because the NMR signal is acquired from an object moving with constant velocity v in a linear field gradient $G_z$ oriented parallel to v, the conventional NMR pulse sequences will not, in general, succeed in giving image projections of the object. For example, Fourier transformation of the FID obtained with a 90° pulse on the moving object in the field gradient will not give an image projection of the object. Nor, in general, will spin echoes or stimulated echoes be observed with conventional pulse sequences such as the Hahn echo (96-τ-180-acquired), the CPMG or Stimulated echo sequences. (These pulse sequences are described in standard textbooks on MRI such as P. T. Callaghan, *Principles of NMR microscopy*, Oxford Science Publications, Oxford, 1991). Moreover, conventional Fourier transformation of the echoes would not give a image projection of the object. Special acquisition conditions and methods for extracting the image are therefore now described.

a) Creating a One-dimensional Image Projection from an MMFID

The digitised MMFID, acquired in quadrature, must first be transformed in the time domain by multiplication with the factor $\exp\{-i\gamma G.vt^2/2\}$, where t is the acquisition time after the 90° pulse. This removes a phase factor created by motion with velocity v in a linear magnetic field gradient $G_z$ The resulting transformed FID is then corrected for zero-order phase imbalance by adjusting the phase so as to give a zero first point in the imaginary part of the FID. A full echo is then formed by reflecting the FID using its complex conjugate. Finally the echo is Fourier transformed to obtain an image projection. A fast computer algorithm for achieving this is described in Appendix 2, together with simulated transforms.

b) Methods for Creating Image Contrast Using Motionally Modified Spin Echoes (MMSE's) and Motionally Modified Free Induction Decays (MMFID's)

Figure 6:
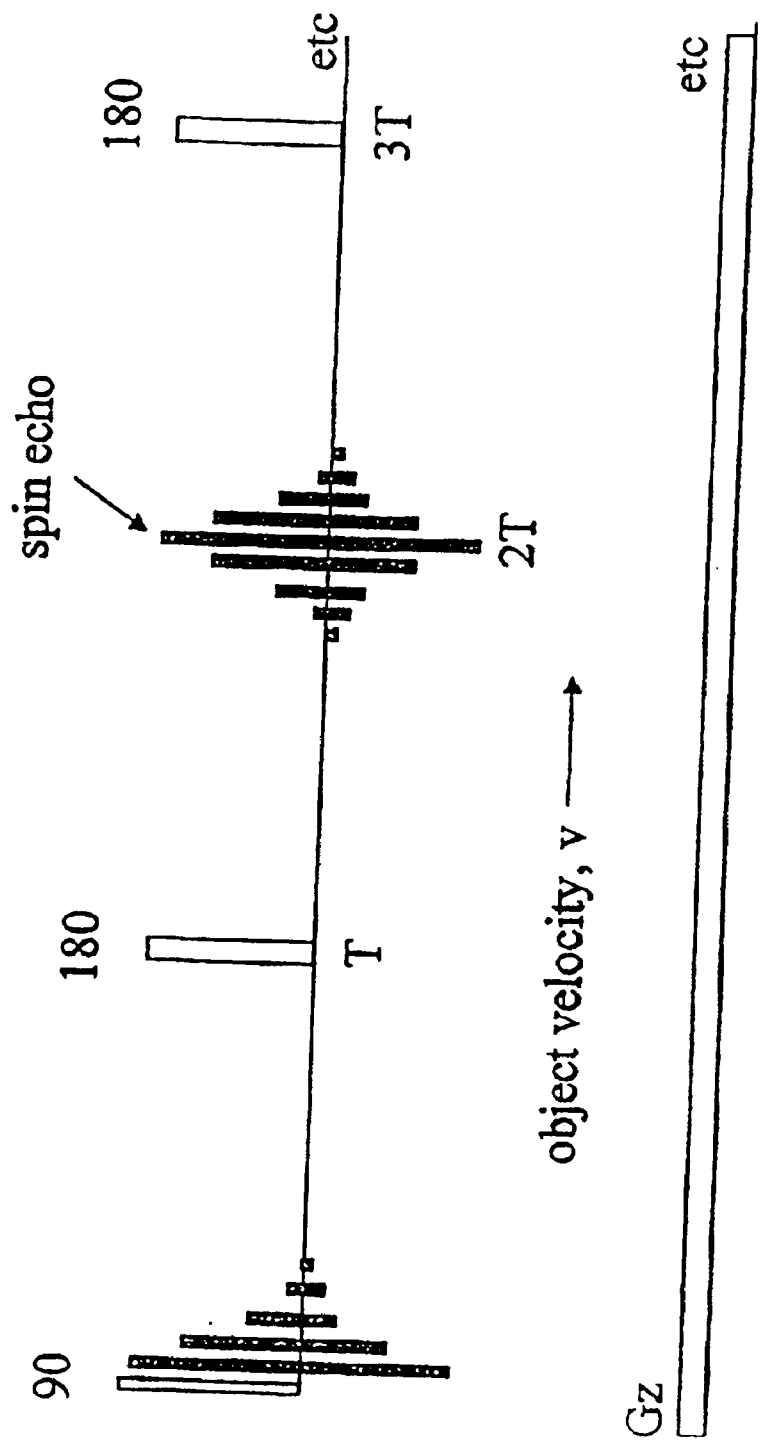
FIG. 6 shows an exemplary pulse sequence suitable for $T_2$ weighting based on motionally modified spin echoes.

In many applications, such as the on-line detection of bruises in fruit, it is desirable that images are acquired with contrast (or intensity distribution) weighted by one or more of several NMR parameters such as the relaxation times $T_2^*$, $T_2$, $T_1$, or the self-diffusion coefficient, D, or the flow velocity (in the case of fluids). The following protocols describe how motionally modified FID's (MMFID's) and/or motionally modified spin echoes (MMSE's) can be used to create images weighted by each of these parameters:

$T_2$ Contrast in Images Created Using Motionally Modified Spin Echoes $T_2$ contrast in images can be created using spin echoes created by hard 180° pulses with a modified Hahn echo or CPMG (Carr Purcell Meiboom Gill) pulse sequence applied to the moving object in the linear field gradient $G_z$. As shown in Appendix 3, for a spin echo to be observed, the pulse spacing $\tau$ must be an integral multiple of the acquisition time AQ. Moreover, an image projection can only be extracted from the spin echo if it is first transformed to remove a motional phase factor. This is described in Appendix 4. A representative pulse sequence is shown in FIG. 6. $T_2$ contrast is important because different parts of the object are often associated with different values of $T_2$ and this will be seen in the image projection. This can be exploited in many ways. For example, frozen parts of foods have a much shorter $T_2$ than unfrozen regions so that frozen and unfrozen parts of a food can be distinguished in the image.

$T_1$ Contrast Using Motionally Modified Spin Echoes

Figure 7:
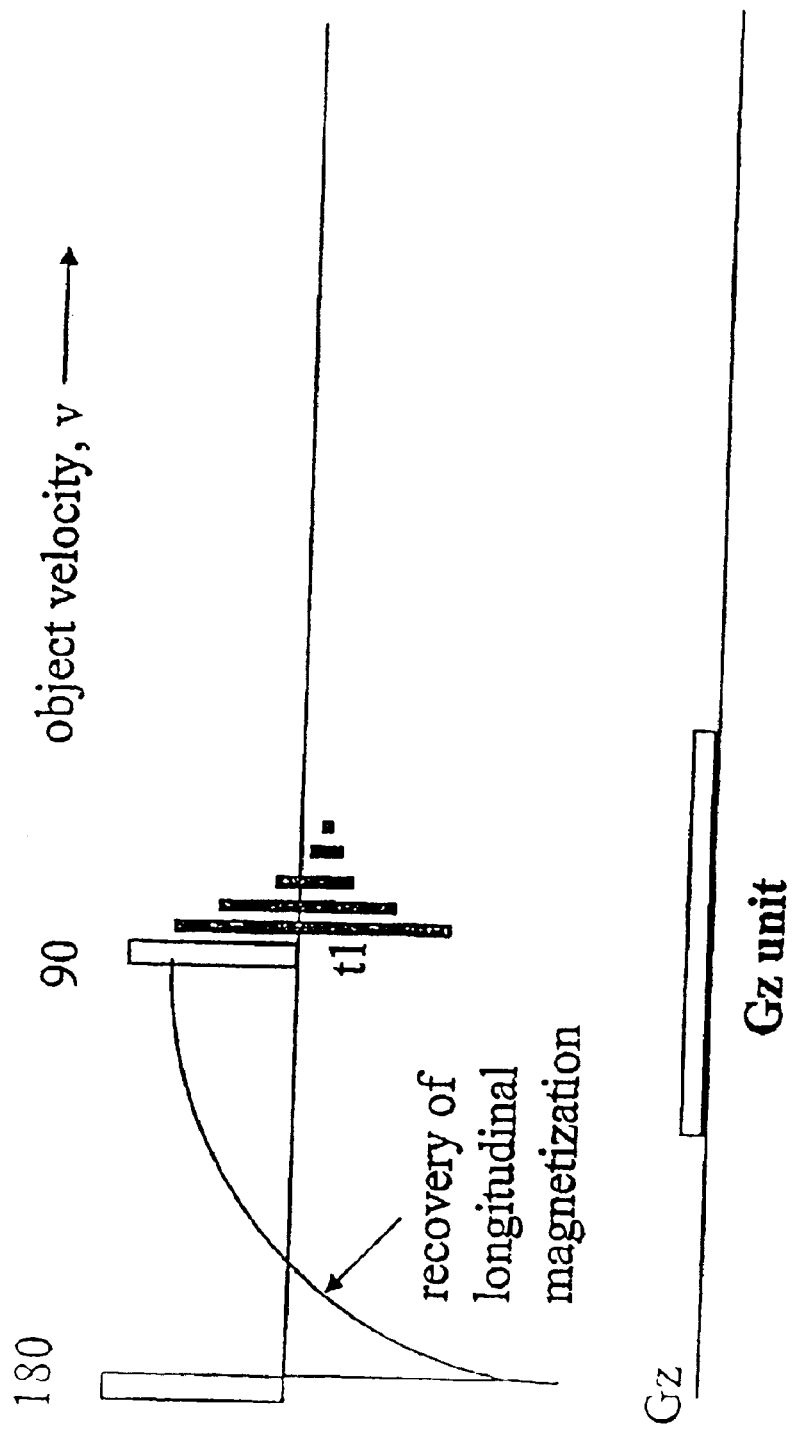
FIG. 7 shows an exemplary pulse sequence suitable for $T_1$ weighting based on motionally modified inversion recovery.
Figure 8:
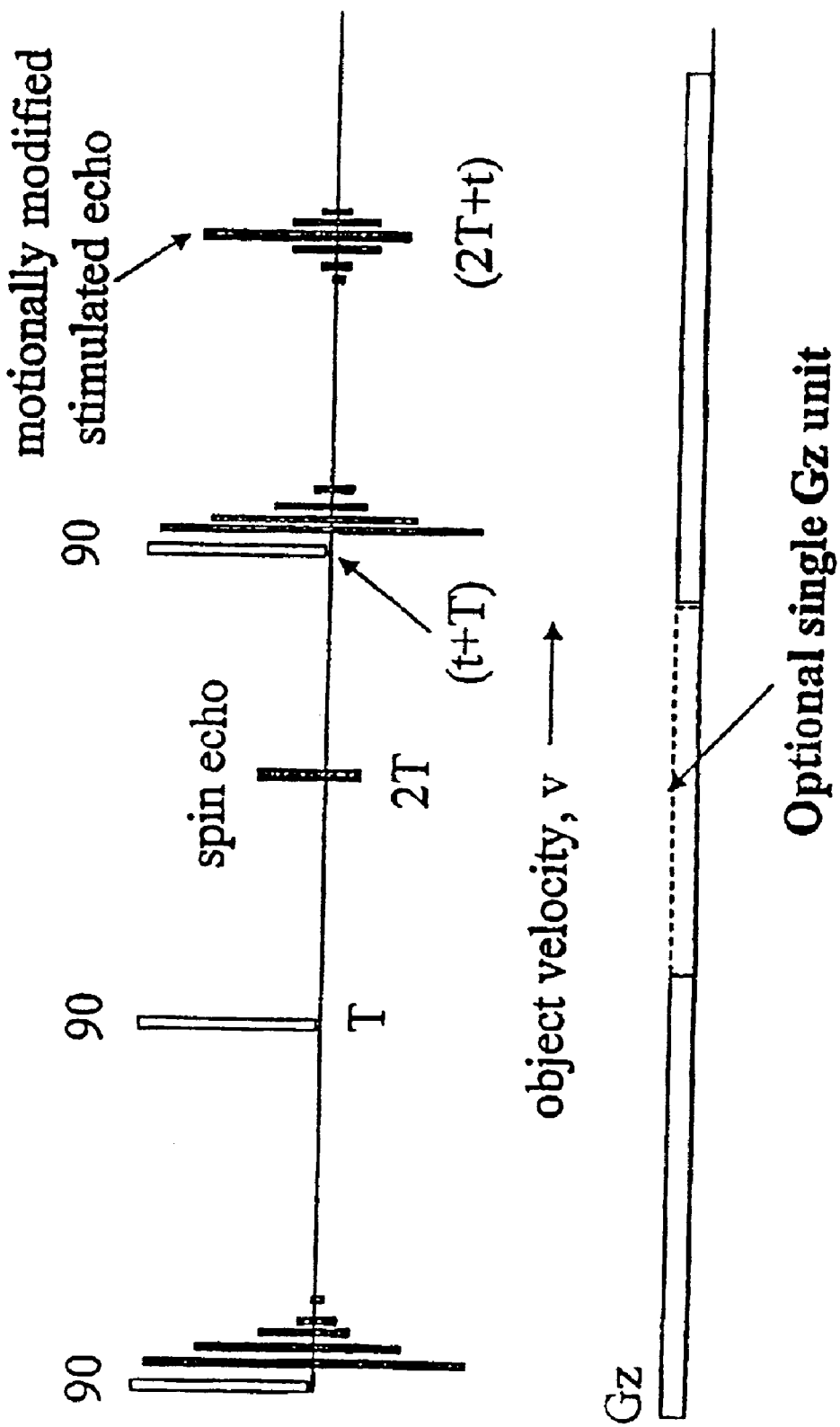
FIG. 8 shows an exemplary pulse sequence suitable for $T_1$ and diffusive weighted imaging based on motionally modified stimulated echoes.

There are several possible ways of introducing $T_1$ contrast into the images. The simplest is to use the inversion recovery sequence whereby the polarized magnetisation, M(0) is inverted by a hard 180° pulse and allowed to recover for a fixed time delay t1, adjusted for each application. After the time delay t1 an MMFID is created by a hard 90° pulse generated by the RF unit in the presence of the linear gradient created by the $G_z$ unit. The pulse sequence is illustrated in FIG. 7. If $T_1$ is sufficiently long, the initial hard 180° pulse can be eliminated by setting the polarizer unit to give $B_0$ antiparallel to v. An alternative pulse sequence which has the advantage of permitting two images to be obtained and compared, one with T1 weighting, the other without involves the stimulated echo pulse sequence. A representative pulse sequence is shown in FIG. 8. Note that a motionally modified stimulated echo is only formed if T=nAQ, and that, because only longitudinal magnetisation exists between the second and third 90° pulse (during the time t) the gradient $G_z$ can be turned off between them. This has the advantage of permitting the use of two $G_z$ units and two RF units rather than one very long unit.

Figure 9:
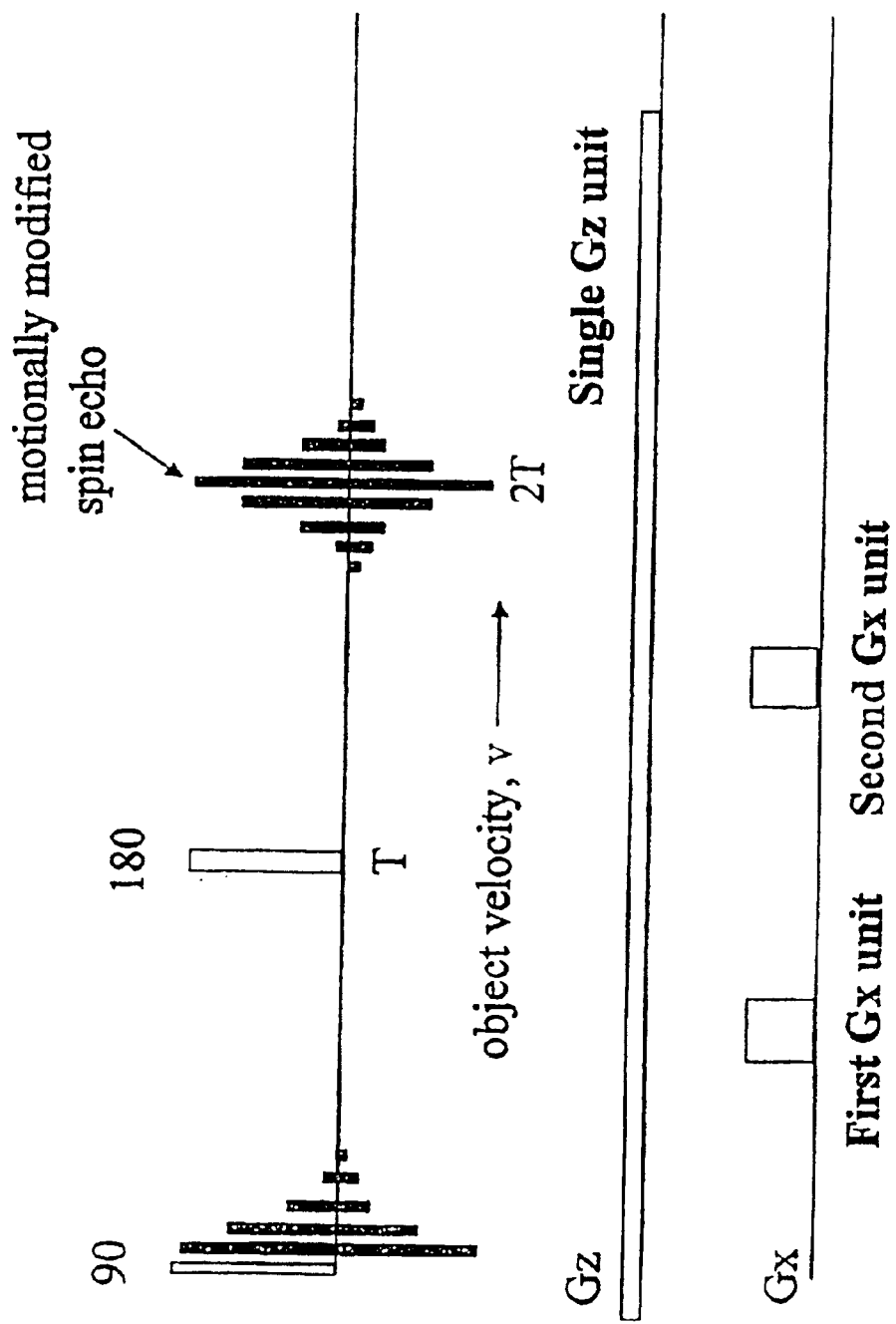
FIG. 9 shows an exemplary pulse sequence suitable for diffusion weighting based on motionally modified spin echoes.
Figure 10:
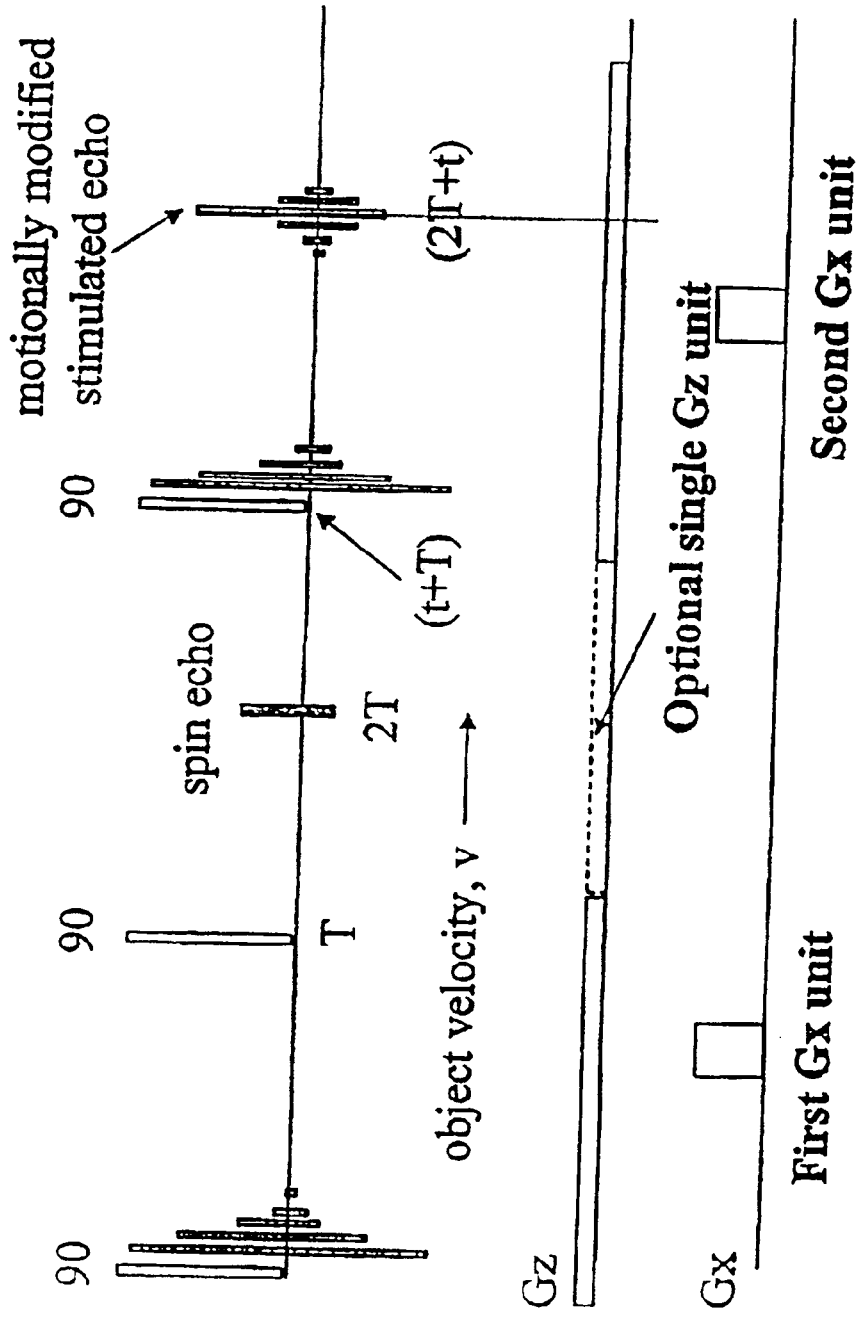
FIG. 10 shows an exemplary pulse sequence suitable for $T_1$ and diffusive weighted imaging based on motionally modified stimulated echoes.

Diffusion Contrast by Combining Motional Echoes with Motion-generated Pulsed field Gradients Diffusion contrast can be created, explicitly, using two or more $G_x$ units. Each $G_x$ unit creates a constant, localised, non-uniform gradient $G_x$ across the solenoid axis and transverse to the $B_0$ field. Motion of the object through these static $G_x$ gradients is equivalent to imposing time-varying (pulsed) field gradients. Suitable pulse sequences are shown in FIGS. 9 and 10. The first is based on the motionally modified Hahn echo pulse sequence; the second on a motionally modified stimulated-echo pulse sequence.

$T_1$ (Low Field) Contrast using MMFID's

Figure 11:
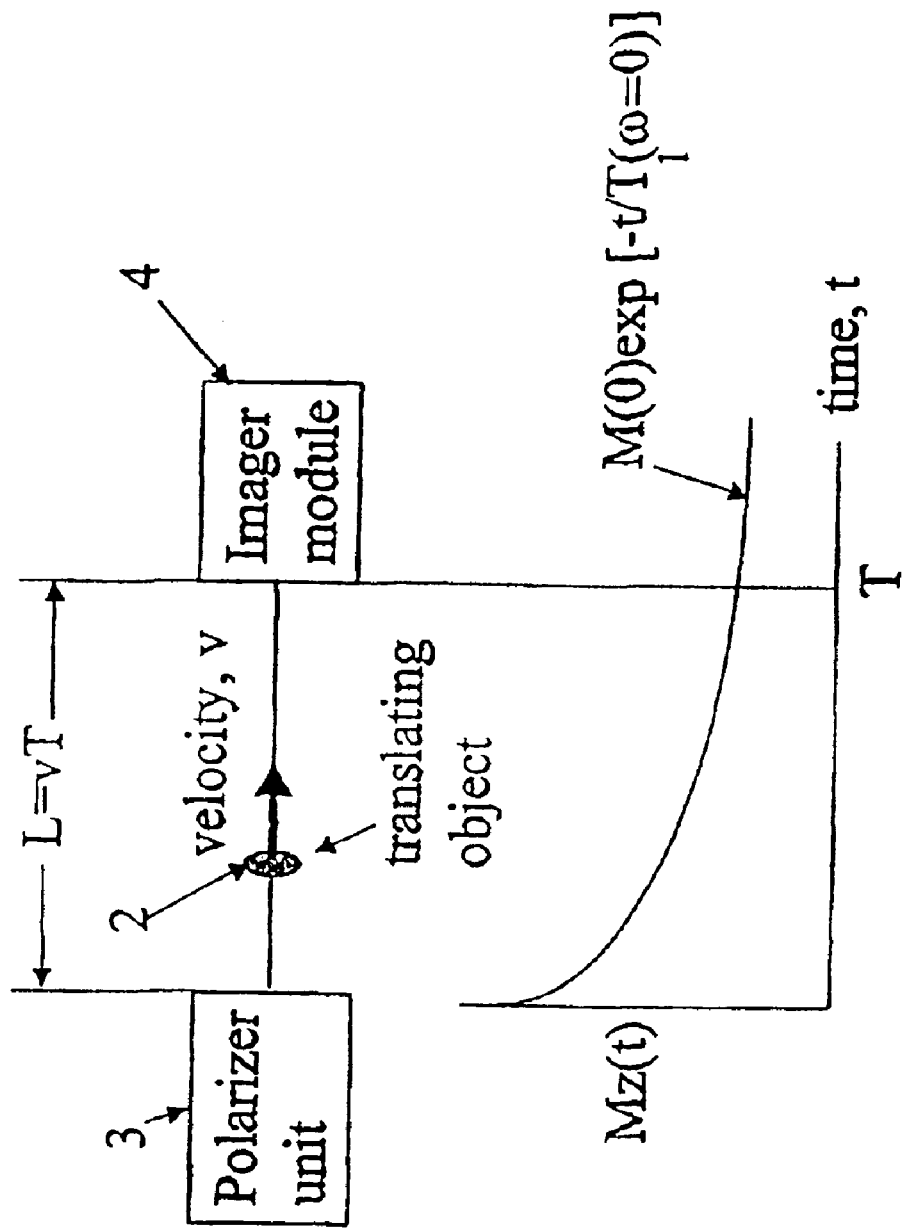
FIG. 11 shows an exemplary arrangement suitable for weighting motional echoes with $T_1$ (low field) relaxation.

With reference to FIG. 11, between the polarizing unit 3 and the imaging unit 4 the sample 2 contains longitudinal magnetisation relaxing in the earth's magnetic field. By varying the time spent between the polarizer and detector, various amounts of $T_1$(low field) relaxation can be introduced. A suitable arrangement is shown in FIG. 11.

c) On-line Detection of Defects and Changes in a Moving Object by Difference Imaging Using Motional Echoes In some applications the acquisition of a single, parameter-weighted image is insufficient to identify a defect, bruise, foreign body etc. In such cases it may be necessary to take the difference between an image (called the first image) acquired with a contrast weighting which is insensitive to the presence of the defect and a second image weighted with a parameter (such as $T_2^*$, $T_2$, $T_1$, or D) which is changed by the presence of the defect. Taking suitably processed differences between the first and second images will then highlight the presence, position and extent of the defect.

The first image can be calculated from the MMFID generated by the first 90° pulse in the pulse sequences listed above. The second image can be calculated from one (or more) of the motionally modified spin echoes generated subsequently.

The difference imaging protocol may, if necessary, be combined with image registration software and/or signal processing software, such as Wiener filtering. All such operations are performed in the least possible time using a fast computer, such as a 233 MHz PC.

d) 2 or 3 Dimensional On-line Imaging Protocols

There are several strategies for this:

Methods Based on Motionally Modified Spin Echoes

Figure 12:
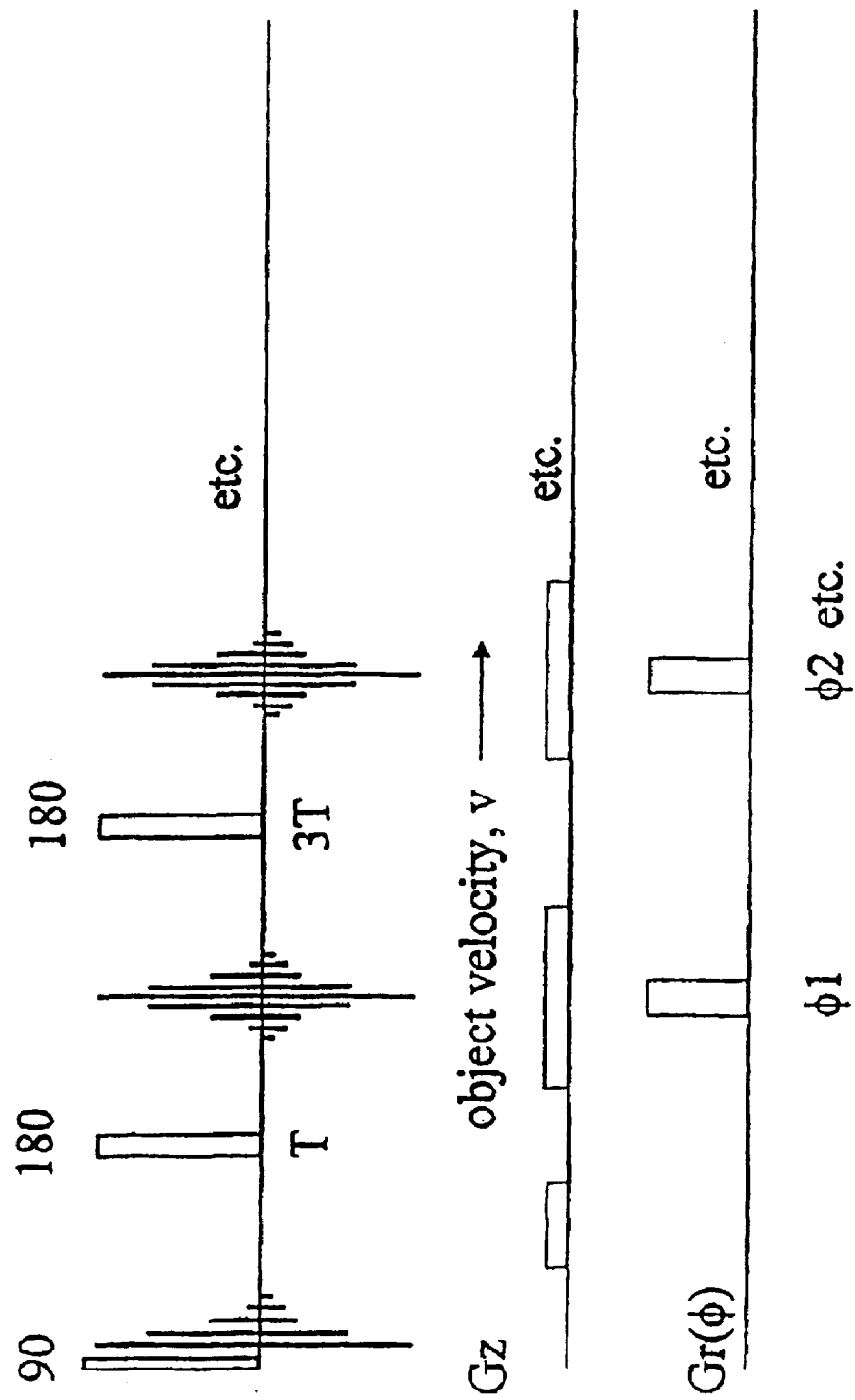
FIG. 12 shows an exemplary pulse sequence suitable for three-dimensional imaging based on motional echoes.

It is possible to undertake 3-dimensional imaging by making use of the $G_\phi$ units to acquire MMSE's in a uniform, steady magnetic field gradient $G_\phi$ oriented transverse to $B_0$ and to the direction of motion v. 3-dimensional imaging uses the back-projection technique, whereby the angular orientation $\phi$ of the field $G_\phi$ relative to the vertical ($\phi=0$) is incremented in equal angular steps between successive motional echoes (or $G_\phi$ units). A representative 3-dimensional pulse sequence is shown in FIG. 12. The image resolution in the transverse (x-y, or r,$\phi$ plane) is determined by the number of increments in the angle $\phi$ and hence by the number of $G_\phi$ units. The success of the protocol requires a long $T_2$ so that sufficient spin echoes can be acquired, and the pulse spacing T must be an integral multiple of AQ.

Methods Based on the Motional Equivalence Principle

Figure 13:
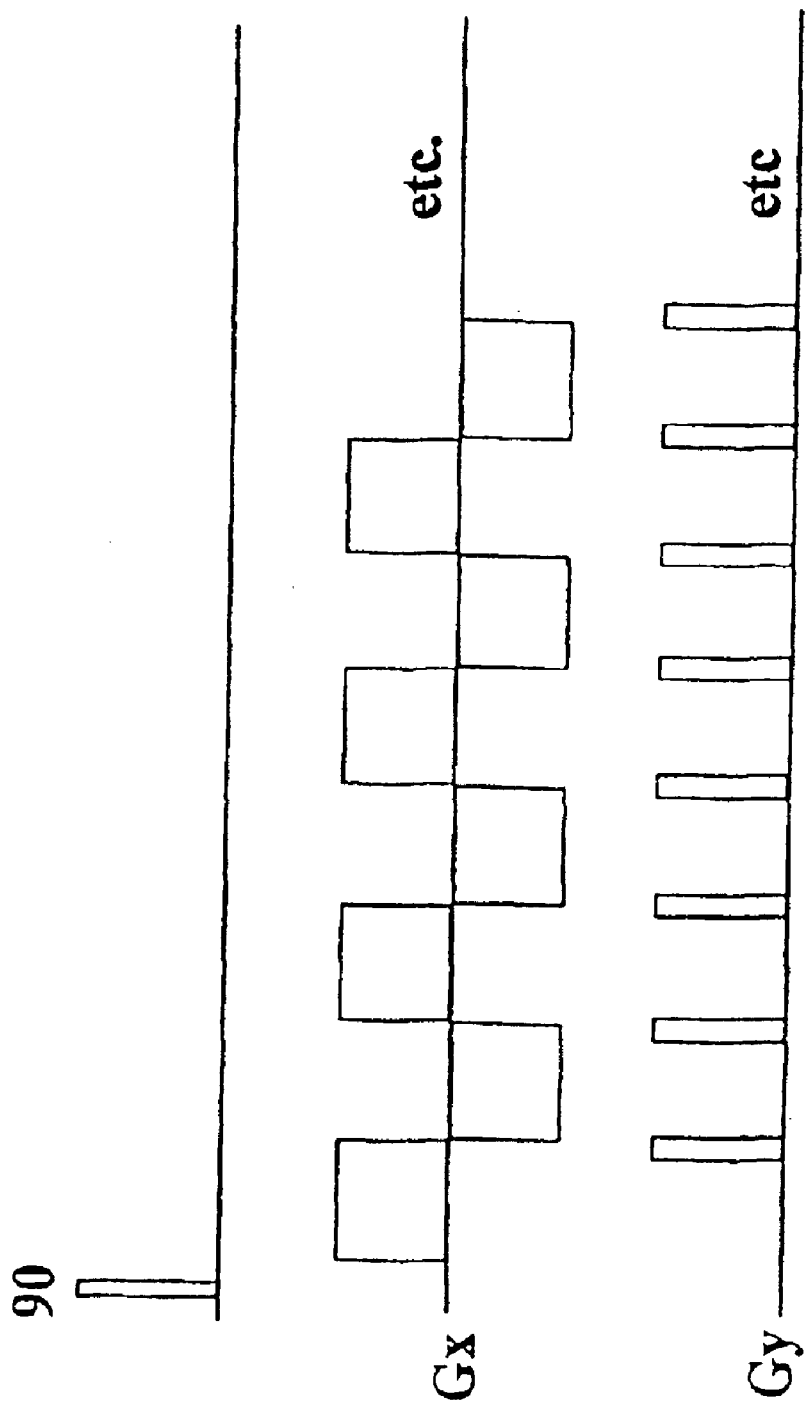
FIG. 13 shows an on-line variation of an echo planar imaging pulse sequence of imaging in the x-y plane.

The Echo Planar Imaging (EPI) protocol uses rapidly switched gradients to generate an image of a non-translating object. Instead of a stationary object and rapidly switched gradients it is possible to create an equivalent pulse sequence by moving the object with linear velocity through an array of steady gradients. A suitable arrangement for two-dimensional imaging in the (x-y) plane transverse to the object's velocity is shown in FIG. 13. Because the gradients are steady there is no problem with eddy current interference. The transverse gradients are created by locating $G_\phi$ units along the $B_0$ and RF units.

e) On-line Flow Imaging Using MMFID's

MMFID's can also be used to determine the velocity distribution in fluids undergoing steady flow down a tube. This is useful for on-line measurements of rheological properties of fluids. Each volume element in a fluid in steady flow has a constant velocity, and so behaves as a very small rigid body and contributes its own motional echo at a position (or time) which depends on its velocity. By analysing the MMFID it is therefore possible to extract the velocity distribution in the fluid. The analysis is presented in greater detail in Appendix 7 for the special case that a thin slice of fluid is initially excited and that this slice is only a single voxel wide. In practice a thin slice of fluid in a plane perpendicular to the flow can be excited using a soft, shaped slice-selective radiofrequency pulse (which can be created by the RF unit) in the presence of the $G_z$ gradient created by the $G_z$ unit.

f) On Line MRI Temperature Mapping

Conventional MRI temperature mapping on stationary objects exploits the temperature dependence of NMR parameters such as the initial magnetisation M(0), the longitudinal relaxation time $T_1$ or the diffusion coefficient D. The on-line protocols presented above also provide M(0), $T_1$ or D weighted profiles of the moving object. By calibrating the temperature dependence of the M(0), $T_1$ or D weighting it is therefore possible to detect on-line temperature changes in the object non-invasively. This could be of benefit in on-line monitoring of chilling or heating processes.

The present invention has thus far been described with reference to specific embodiments. It will be understood, however, that a number of modifications can be made thereto. For example, although the preferred embodiment requires that an object is undergoing continuous, uniform translational motion, in fact the object can be undergoing any non-zero velocity or finite acceleration providing that its movement can be precisely characterised such that the effect of the changing velocity on the nuclear magnetic resonance signals can be predetermined. For example, modification of the factor $\exp\{-i\gamma G.vt^2/2\}$ used in transforming the MMFID signal would be required according to the precise velocity or acceleration of the object.

This has particular significance where objects to be imaged are falling off the end of a conveyor belt, for example. In that situation, the motion of an object can be precisely characterised where it is undergoing continuous acceleration. Arrival of the object into the imaging system and/or determination of its translational motion can be determined by optical beams, as discussed earlier.

Similarly, although it is desirable, as in the preferred embodiments, for the magnetic field $B_0$ to be spatially uniform and for the magnetic field gradient $G_z$ to be linear, it will be understood that these conditions need not hold providing that both the field $B_0$ and the field $G_z$ can be precisely pre-characterised such that appropriate compensation can be made for non-linearities in the transformations for image processing. This enables possible use of non-symmetrical, but precisely characterised coils.

The on-line imaging system and protocols described above find a significant number of important commercial applications, of which examples are enumerated below.

EXAMPLE 1

On line detection of damaged, bruised or diseased fruit and vegetables moving on a conveyor. For example, the bruised region of an apple has a longer $T_2^*$ and a shorter $T_2$ than healthy apple tissue. The difference imaging protocol should therefore be able to detect the existence and extent of bruising.

EXAMPLE 2

On-line detection of foreign bodies within foods on a conveyor. A foreign body such as glass or plastic gives no NMR signal in the imager unit. Metal will produce gross image distortions.

EXAMPLE 3

On-line monitoring of the extent of freezing of foods during e.g. Blast Freezing. Here it is important that the inside is completely frozen. Frozen regions give no NMR signal. Unfrozen parts give an NMR signal.

EXAMPLE 4

On-line detection of the degree of ripeness of fruit. Melons being an obvious application.

EXAMPLE 5

On-line monitoring of the physical condition of continuously extruded food materials. Here any change in temperature, viscosity or water content would be expected to change relaxation times and/or diffusion coefficients and hence be detectable.

EXAMPLE 6

On line detection of cracked or broken materials. A crack gives no NMR signal so can be detected.

EXAMPLE 7

On-line monitoring of the success of a "de-pitting" plant removing pits from the inside of cherries, olives and the like moving on a conveyor.

EXAMPLE 8

On-line monitoring of the porosity and internal structure of cheeses, breads, and layered food products.

EXAMPLE 9

On line monitoring of filling levels within packaged goods.

EXAMPLE 10

On line monitoring of Theological changes in pastes, slurries, chocolates and other opaque semi-fluid materials flowing down pipes or tubes.

EXAMPLE 11

On line monitoring of the progress of operations such as baking, heating, cooling, drying, rehydration, freezing etc.

EXAMPLE 12

On-line monitoring of the composition of flowing chemical mixtures in the chemical and pharmaceutical industries.

APPENDIX 1

A Theoretical Analysis of Motionally Modified FID's

For the time being, effects of spin relaxation, spin diffusion, and spin couplings are ignored. Consider spins in the volume element dV at position vector r(0) at time 0. At time t, this will have moved to r(t)=r(0)+vt, where v is the linear velocity. The precession frequency at r(t) will be $$\omega(r(t),t)=2\pi f(r(t),t)=\gamma B_0+\gamma G.r(t)=\gamma B_0+\gamma G.r(0)+\gamma G.vt \quad [1]$$

As the spins initially at r(0) are carried along in the field gradient, they will accumulate a net phase angle given by $$\phi(r(t),t)=\int_0^t dt' 2\pi f(r(t'),t')=\gamma B_0 t+\gamma G.r(0)t+\gamma G.vt^2/2 \quad [2]$$

The spin density ρ(r(t),t) of spins at r(t) at time t is clearly equal to ρ(r(0),0) if we ignore diffusion and bulk motion of the sample other than the linear translation v. The contribution dS(r(t),t) to the total signal S(t) from spins at r(t) is therefore given by $$dS(r(t),t)=A.\rho(r(t),t).\exp[i\phi(r(t),t)]=A.\rho(r(0),t).\exp[i\gamma B_0 t+i\gamma G.r(0)t+i\gamma G.vt^2/2] \quad [3]$$

Neglect the constant of proportionality, A, and write r(0) simply as r and ρ(r(0),t) simply as ρ(r). The phase factor exp($i\gamma B_0 t$) is eliminated by the demodulator by setting it "on-resonance". This leaves, $$dS(r(t),t)=\rho(r).\exp[i\gamma G.rt+i\gamma G.vt^2/2] \qquad [4]$$

The total signal S(t) is then given by integrating over the whole volume of the sample:

$$S(t)=\int dV\rho(r).\exp[i\gamma G.rt+i\gamma G.vt^2/2] \qquad [5]$$

$$S(t)=\exp[i\gamma G.vt^2/2]\int dV\rho(r).\exp[i\gamma G.rt] \qquad [6]$$

The integral is none other than the conventional expression for imaging a stationary object in a linear gradient. Equation [6] shows that this is modulated by the exponential factor exp[$i\gamma G.vt^2/2$] arising from the motion. Note that the vector product shows there is no motional modulation or echo when the gradient is orthogonal to v. Equation [6] also shows that to extract an image from a motional echo one first multiplies the FID by the factor exp[$-i\gamma G.vt^2/2$], then Fourier transforms the result in the normal way for imaging.

The existence of Artificial "Pseudo-echoes" in the Computer Simulation

It is observed that when a finite number of voxels are used to simulate the formation of motionally modified FID's, that a periodic train of echoes are formed. (See Appendix 2). These echoes are displaced to longer times as the number of voxels (the digitisation) increases. In the limit of an infinite number of voxels, corresponding to an experiment on a real object, no echo will be observed. The existence of these "pseudo echoes" can be analysed as follows.

Consider equation [4] for the signal from a volume element $$dS(r(t),t)=\rho(r).\exp[i\gamma G.rt+i\gamma G.vt^2/2] \qquad [7]$$

The motional phase factor in this equation is $\gamma G.v\, t^2/2$. There will be rephasing of this factor if it is a multiple of $\pi$. That is if, $$\gamma G.vt^2/2=\pi M, \text{ where } M \text{ is an integer, } 0, 1, 2 \ldots \qquad [8]$$

This will be true at times, t, such that, $t=[2\pi M/\gamma G.v]^{1/2}$. A motional echo will only be formed if the stationary phase factor, $\gamma G.r\, t$, in equation [7] is also a multiple of $\pi$ at the times, $t=[2\pi M/\gamma G.v]^{1/2}$. In other words, $\phi_{stat}=\gamma G.r\, t$, must be a multiple of $\pi$ at $t=[2\pi M/\gamma G.v]^{1/2}$ for a motional echo.

But the frequency $\gamma G.r$ has to lie within the digitised spectral width. In other words it must correspond to a point $k\gamma G.\Delta x$ where k is an integer such that $-N/2<=k<=(N-1)/2$. Here N is the number of points in the FID and therefore in the spectrum obtained by Fourier transformation. N is assumed to be a power of 2, typically 256 or 512 points. Therefore $$\phi_{stat}=k\gamma G.\Delta x.t \qquad [9]$$

Here $\Delta x$ is the voxel size given by $v.\Delta t$ where $\Delta t$ is the dwell time, which, by Nyquist's theorem is related to $\Delta x$ as, $$\text{Spectral width}=2\pi/\Delta t=\gamma G.N\Delta x \qquad [10]$$

Substituting $\Delta x=v\Delta t$, equation [10] becomes $2\pi/\Delta t=\gamma G.v N\Delta t$ or $$\Delta t=[2\pi/\gamma G.vN]^{1/2} \qquad [11]$$

Therefore $$\phi_{stat}=k\gamma G.v\Delta t.t=(2\pi)^{1/2}k\gamma G.vt/[\gamma G.vN]^{1/2} \qquad [12]$$

At the time that the motional phase factor is refocused, $t=[2\pi M/\gamma G.v]^{1/2}$, the stationary phase factor is therefore $$\phi_{stat}=k\gamma G.v[2\pi M/\gamma G.v]^{1/2}(2\pi)^{1/2}/[\gamma G.vN]^{1/2} \qquad [13]$$

or $$\phi_{stat}=2\pi k[M/N]^{1/2} \qquad [14]$$

But k is an integer, therefore, to be true, the factor $[M/N]^{1/2}$ must also be an integer, say, p, then $$[M/N]=p^2 \text{ or } M=p^2 N \qquad [15]$$

If p=0 the object is stationary. Taking p=+/−1 we find M=N. This is an integer because N is a power of 2, so both the motional and stationary phase factors are a multiple of $2\pi$ at $t=[N2\pi/\gamma G.v]^{1/2}$. This time occurs at the point $t/\Delta t$ in the FID. But from equation [11], $\Delta t=[2\pi/\gamma\, GvN]^{1/2}$. So this is at the point N. This proves there is a "pseudo-echo" at point N in the FID. Since the spectral width is also N points wide, this "pseudo-echo" is produced in the simulation (but not reality) when the object has translated a distance equal to the spectral width. Similarly there are pseudo-echoes at p=+/−2, +/−3 etc. corresponding to translation through 2 and 3 . . . sweep widths and to points 2N and 3N . . . pN in the FID.

Figure 14:
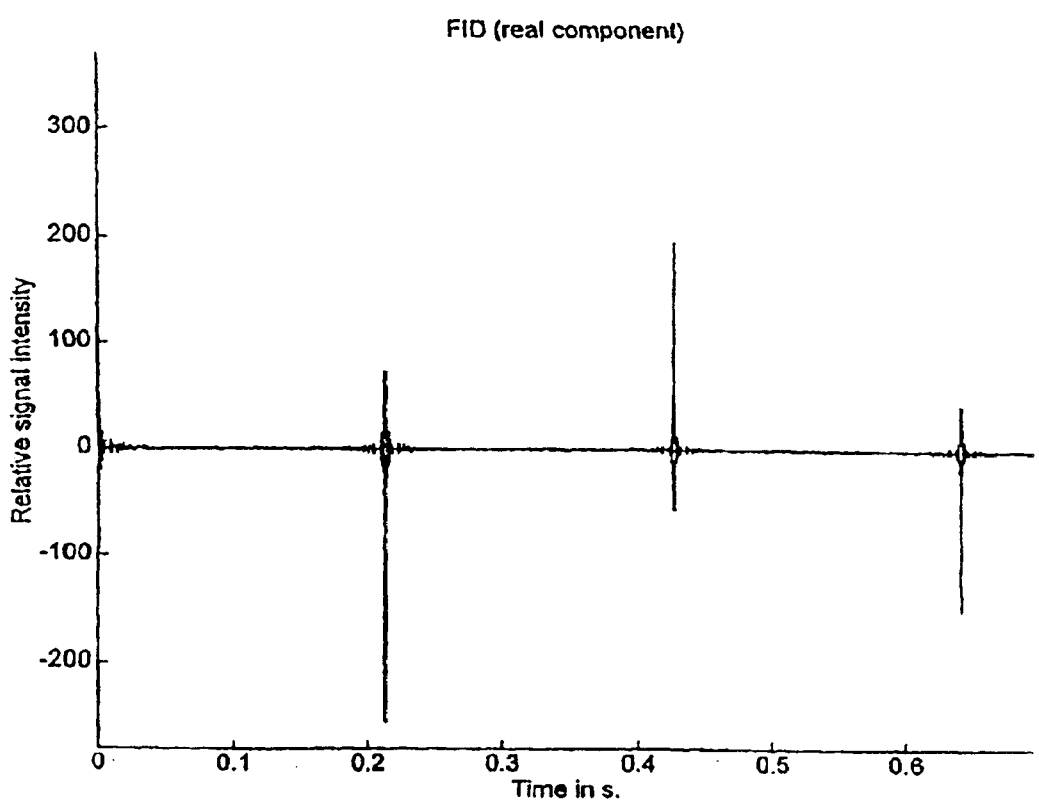
FIG. 14 is a plot of signal intensity versus time showing pseudo-echoes as generated by a computer simulation of free induction decays which are not produced in real measurements.
Figure 15:
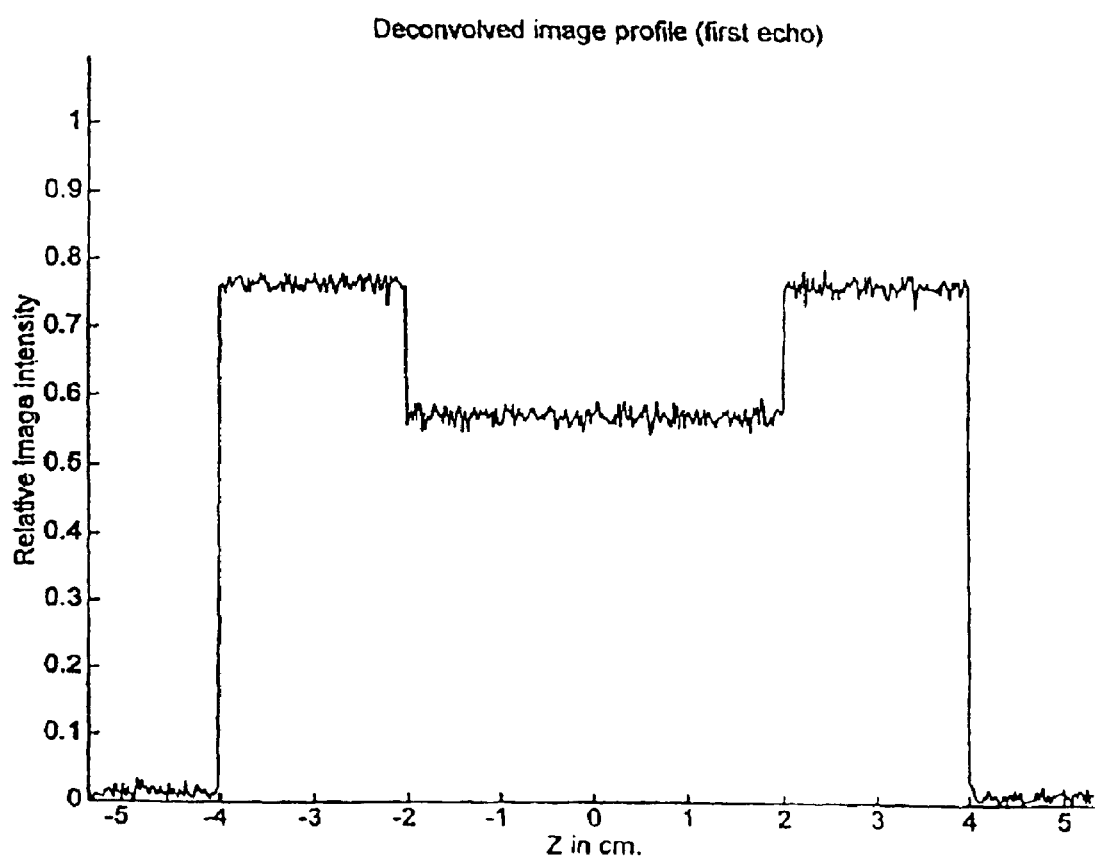
FIGS. 15 and 16 show deconvolved image profiles as a result of processing the pseudo-echoes of FIG. 14, with FIG. 15 corresponding to the first pseudo-echo and FIG. 16 corresponding to the second pseudo-echo.
Figure 16:
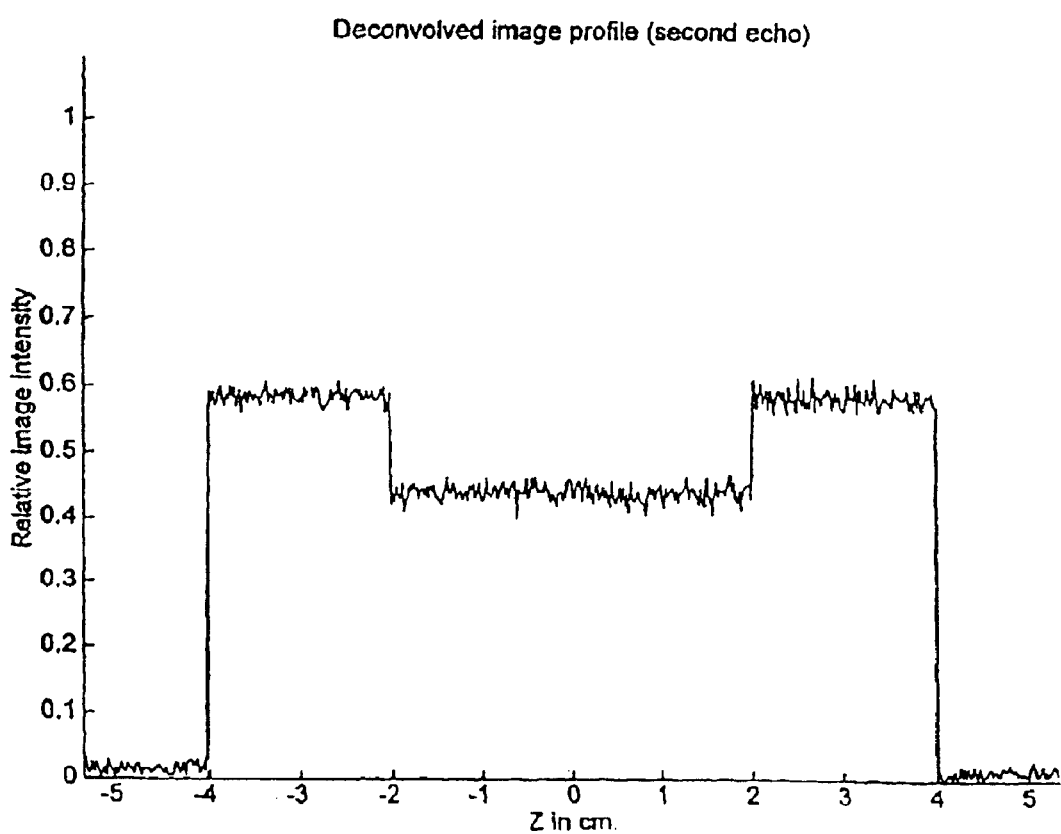
Figure 17:
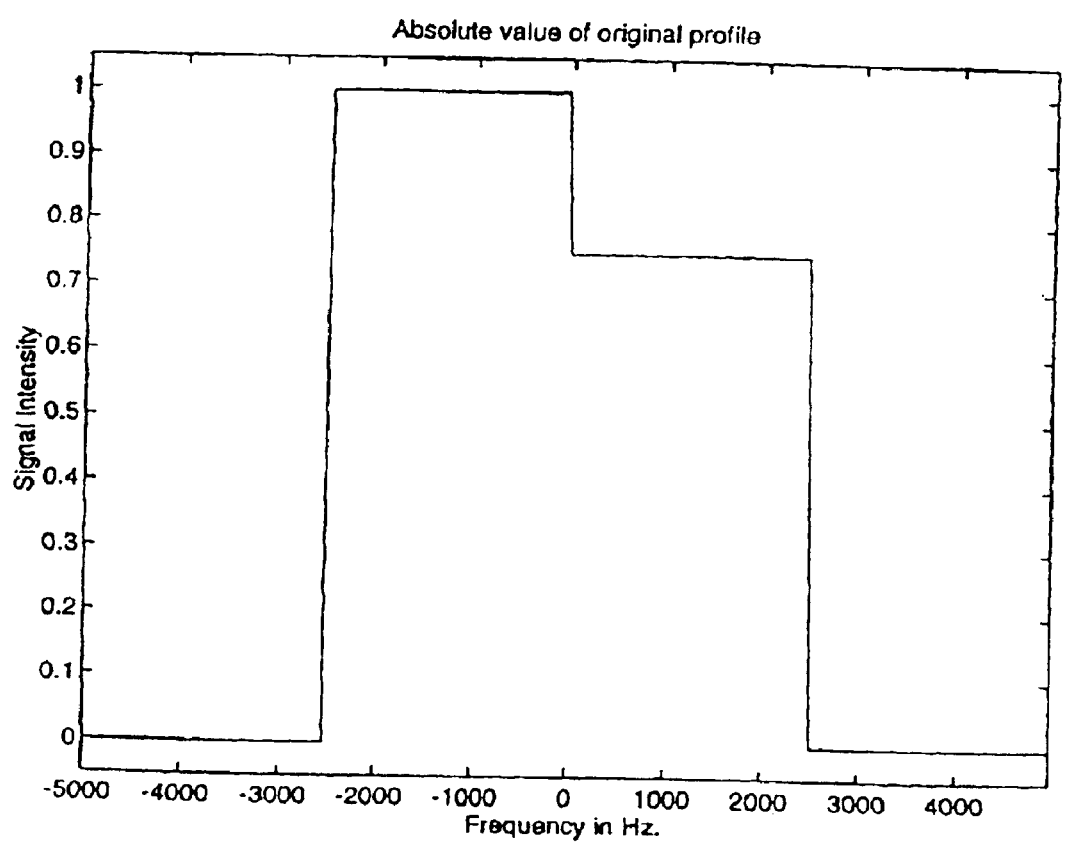
Figure 18:
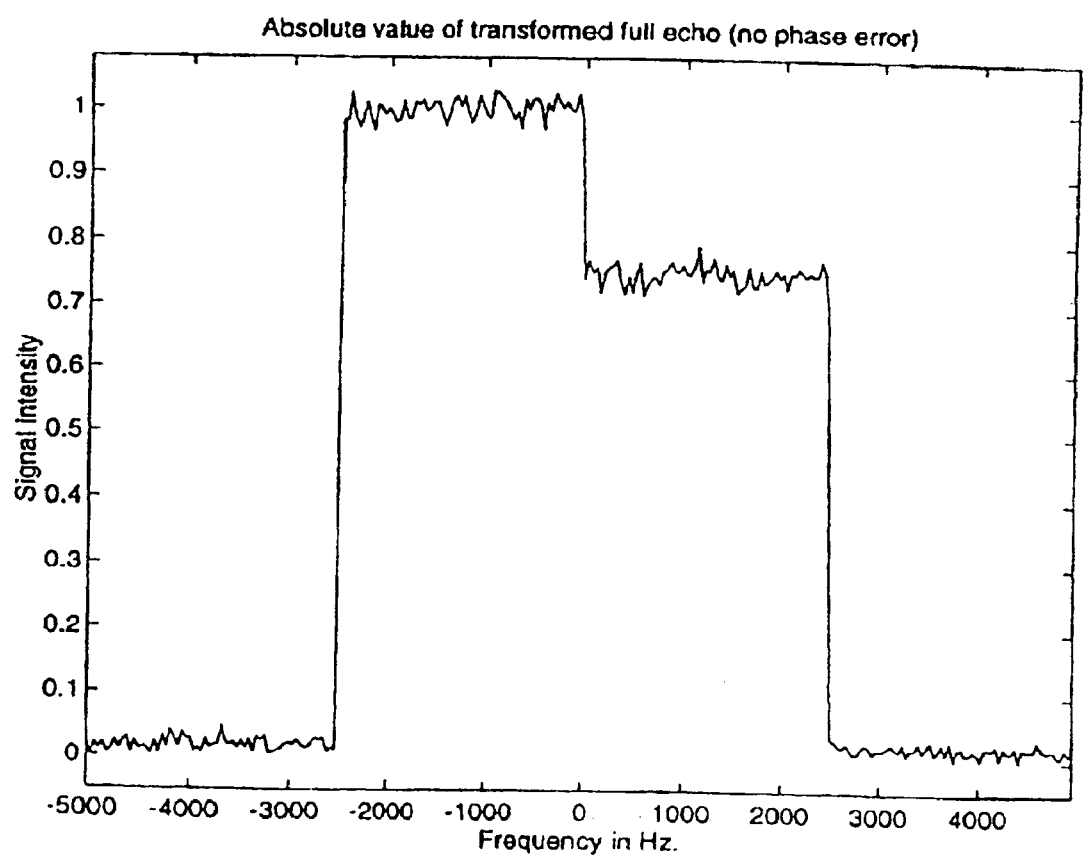
Figure 19:
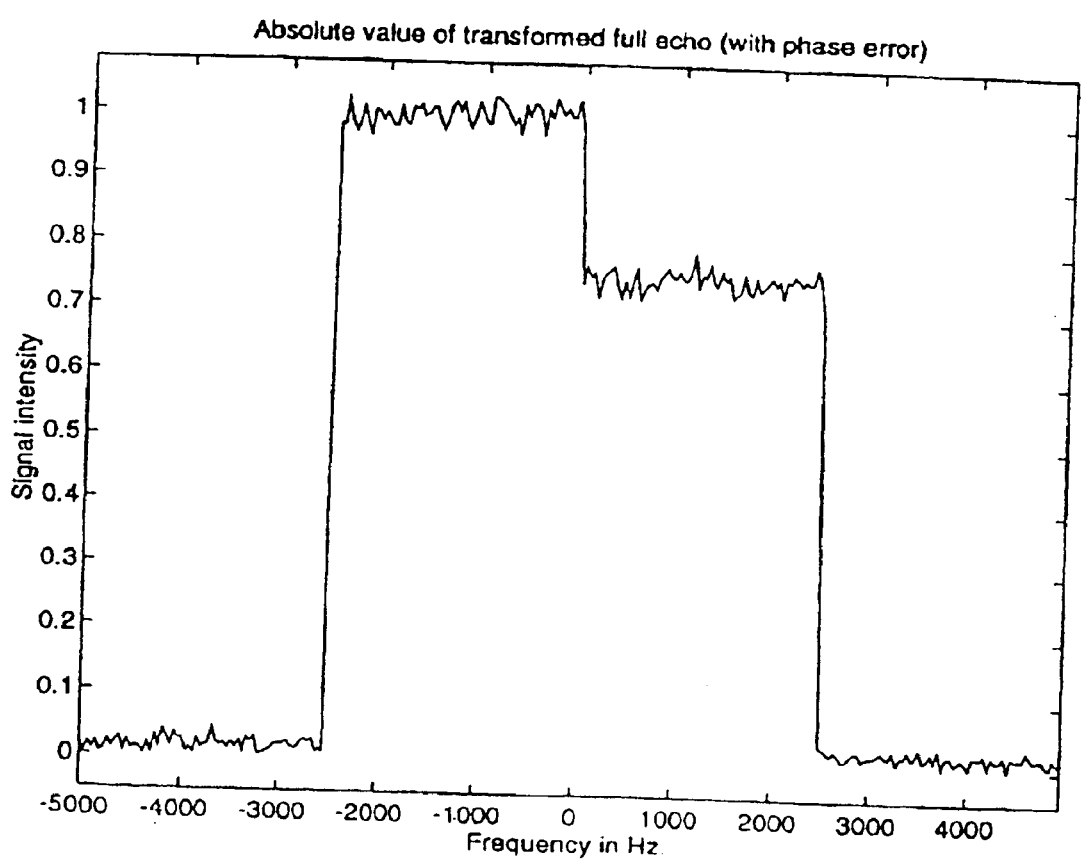
Figure 20:
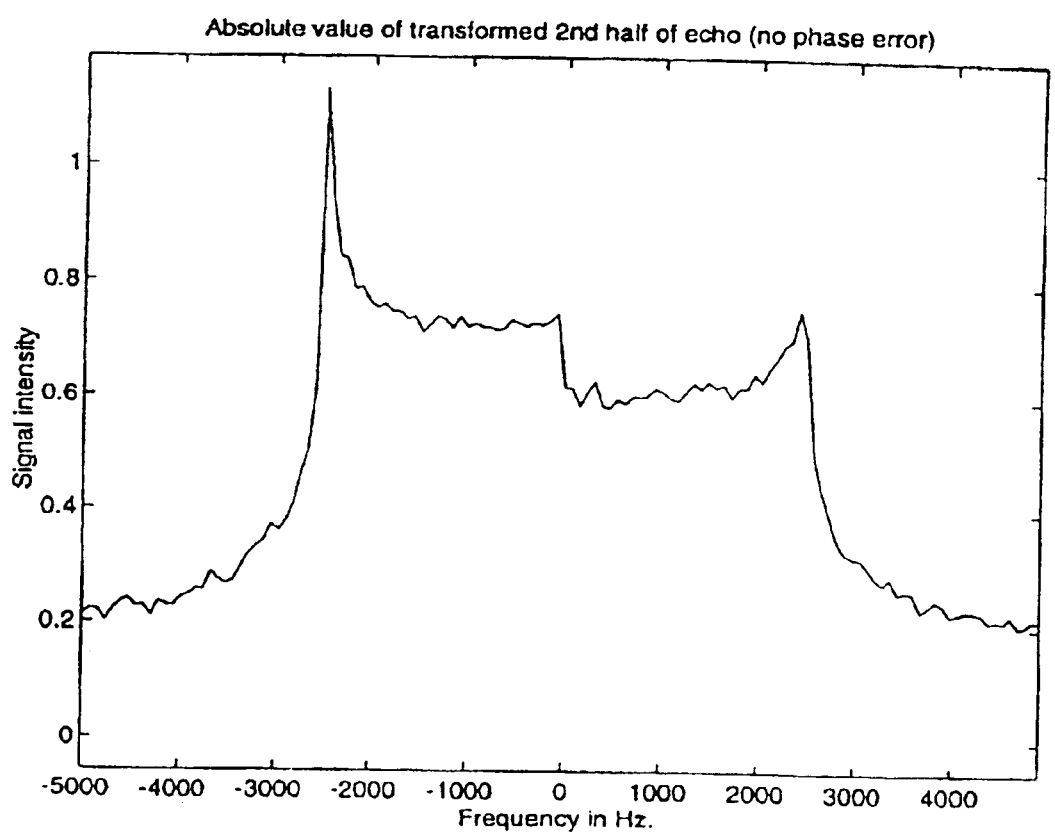
Figure 21:
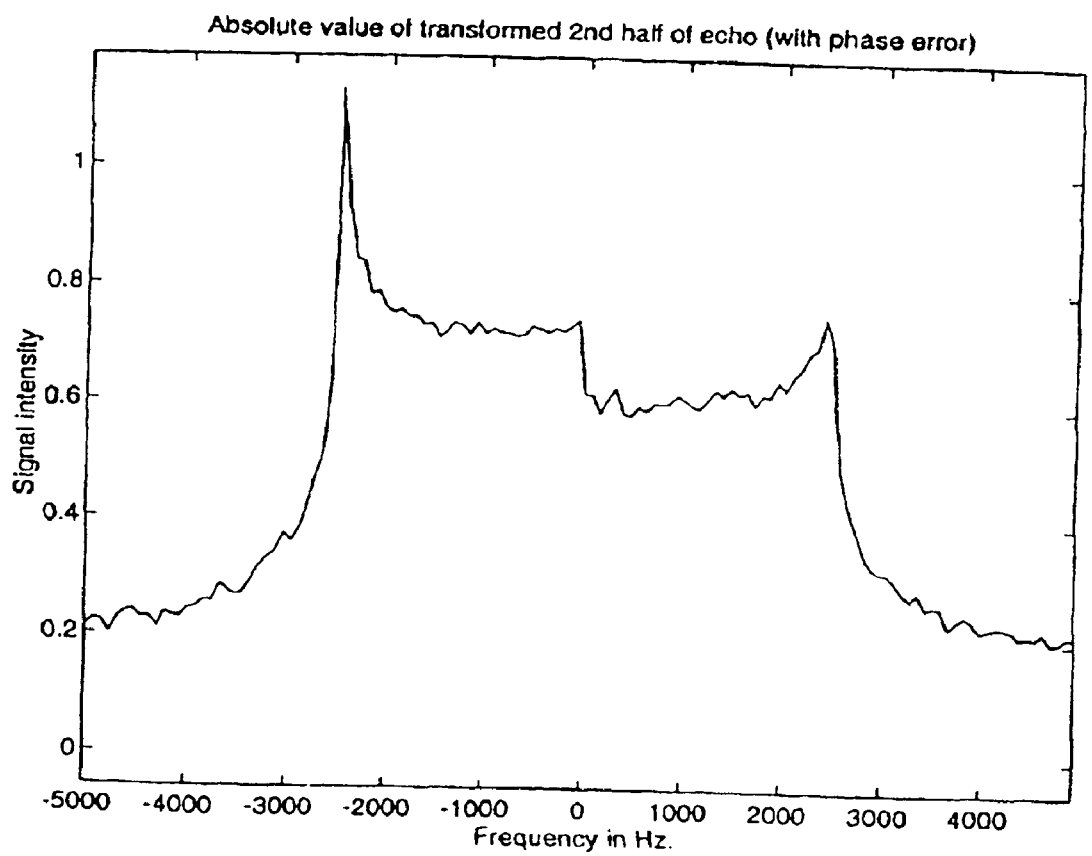
Figure 22:
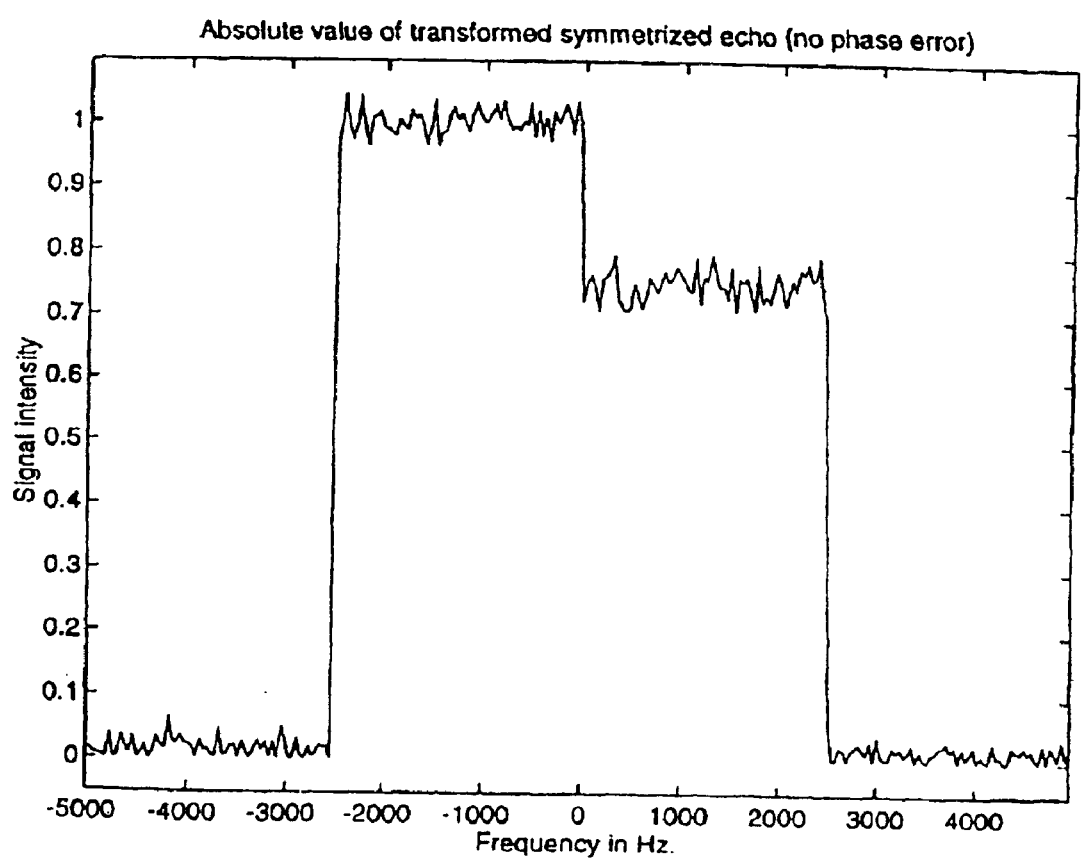
Figure 23:
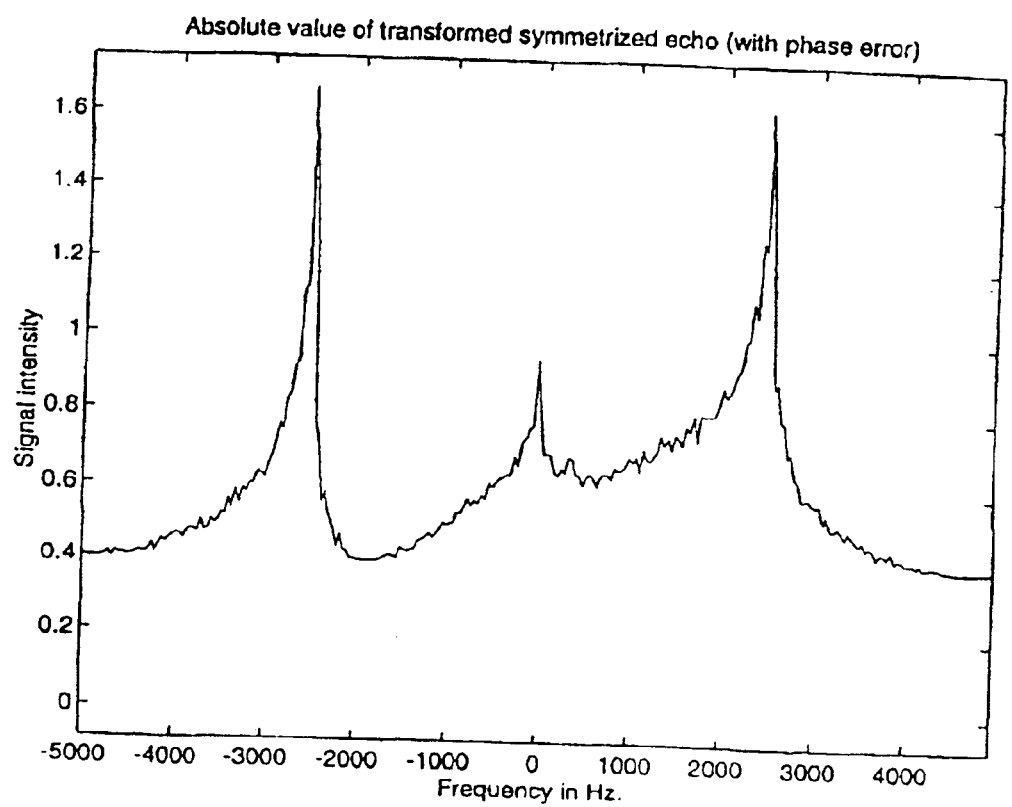
Figure 24:
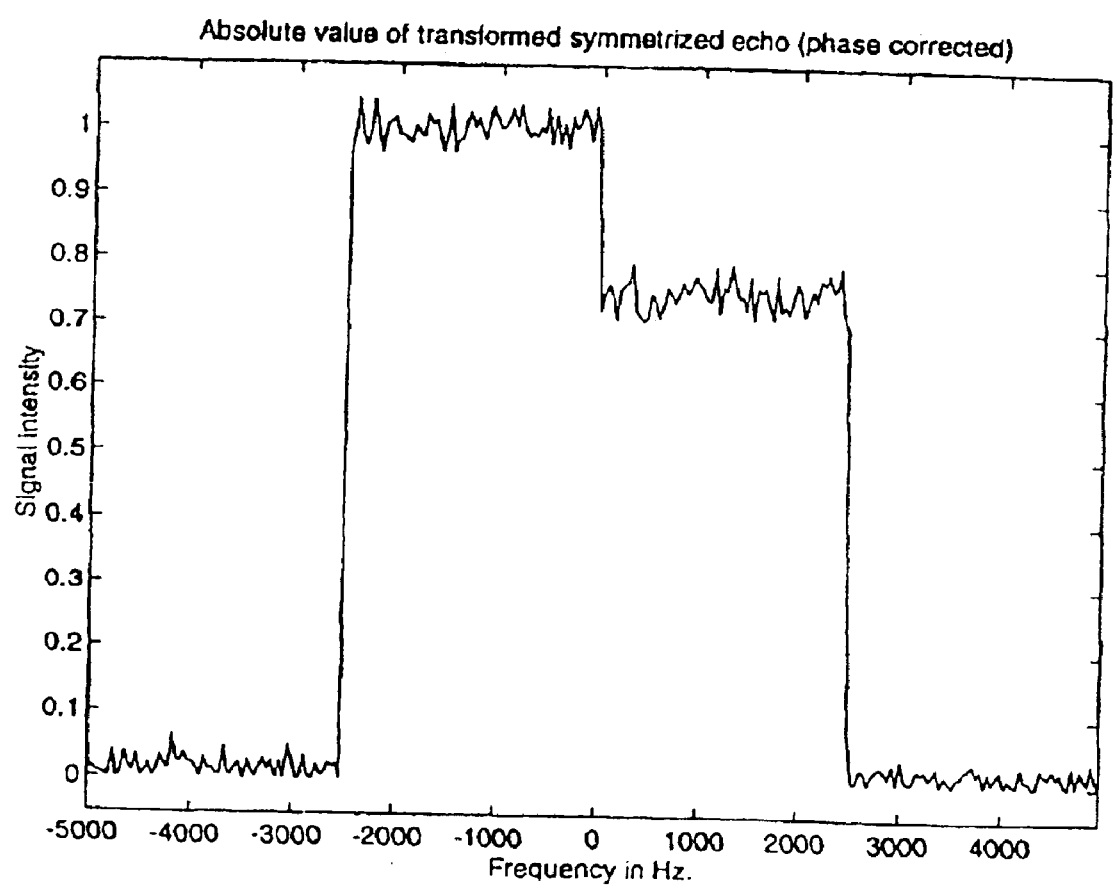

Pseudo-echoes are seen in the computer simulation of FIG. 14. FIGS. 15 and 16 show that pseudo-echoes can be processed just like genuine MMSE's to produce an image projections. However, unlike genuine MMSE's, pseudo-echoes can be displaced to longer acquisition times in the simulation by the expedient of increasing the number of cells per unit of spatial resolution within the object. In the limit of a real object, for which there are an infinite number of cells, the pseudo-echoes will be displaced to infinite time, and therefore will not be observed in the real world. They have been included because they will appear in computer simulations and could be confused with genuine MMSE's. To avoid pseudo-echoes, the magnetization of at least two voxels in the sample should be calculated per unit of digital resolution.

APPENDIX 2

The Computer Algorithm for Converting an MMFID into an Image Projection

This is based on equation [6] in Appendix 1:

$$S(t)=\exp[i\gamma G.vt^2/2]\int dV\rho(r).\exp[i\gamma G.rt] \qquad [6]$$

The integral is none other than the conventional expression for imaging a stationary object in a linear gradient. Equation [6] shows that this is modulated by the exponential factor exp[$i\gamma G.vt^2/2$] arising from the motion. Note that the vector product shows there is no motional modulation or echo when the gradient is orthogonal to v. Equation [6] also shows that to extract an image from an MMFID one first multiplies the FID by the factor exp[$-i\gamma G.vt^2/2$]. The resulting transformed FID is then corrected for zero-order phase imbalance by adjusting the phase so as to give a zero first point in the imaginary part of the FID. An echo can then formed by reflecting the FID using its complex conjugate, according to the following algorithm.

Let the FID be stored in an array f, of length N complex points. Then form a new array f', of length 2N complex points, as follows:

f'[1]=0;

For j=1 to N, f'[j+N]=f(j);

For j=2 to N, f'[j]=f'(2N+2−j)*.

Finally the "echo" is Fourier transformed to obtain an image projection. Resulting simulated image projections are shown in FIGS. 17 to 24 together with the distortions arising when phase imbalances are not corrected.

For generality in the simulation, the object symmetry has been deliberately removed by making the left hand side larger than the right hand side.

APPENDIX 3

The Origin of Motionally Modified Spin Echoes

Equation [7] in appendix 1 shows that motion in the field gradient Gz modifies the FID signal by the factor $\exp[i\gamma G.vt^2/2]$. We now show that this factor is unity whenever t is an integral multiple of the acquisition time, AQ.

Proof.

At the acquisition time, $t=N\Delta t=AQ$. But equation [11] in appendix 1 shows that $\Delta t=[2\pi/\gamma G.v\ N]^{1/2}$, so that $AQ=[2\pi N/\gamma G.v]^{1/2}$. At the acquisition time the exponential factor, $[i\gamma G.vt^2/2]$ is therefore, $$[i\gamma G.vAQ^2/2]=[i\gamma G.v\{2\pi N/\gamma G.v\}/2]=i\pi N$$

But $\exp(i\pi N)=1$ provided N is even. However, N is usually set to a multiple of 2, so: this condition is satisfied for all integral multiples of AQ. QED.

Figure 25:
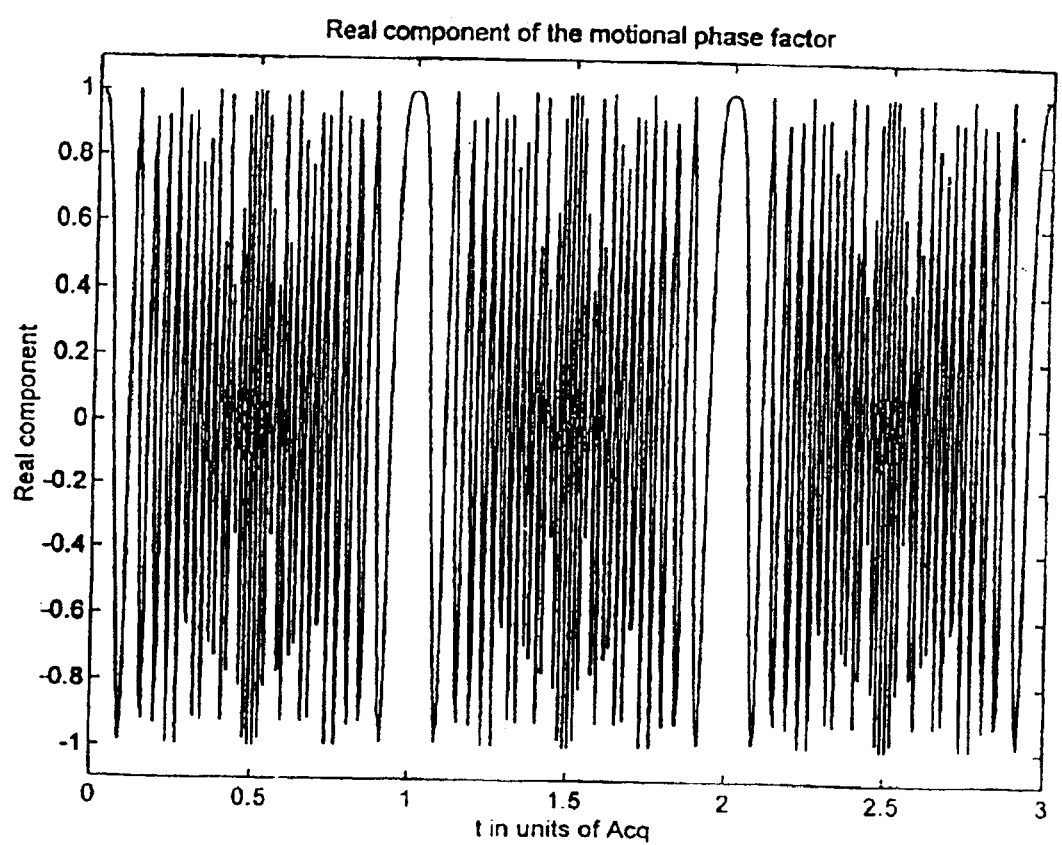
FIG. 25 shows a numerical evaluation of the real component of the motional phase factor $\exp\{i\gamma G.vt^2/2\}$ as a function of acquisition time.

FIG. 25 shows a numerical evaluation of the motional phase factor, $\exp[i\gamma G.vt^2/2]$, and confirms the unities at multiples of AQ. Physically, the instantaneous frequency ($\gamma G.vt/2$) of this factor increases continuously with time. However, since the time t is discretized in dwell time units, the effect of aliasing makes the apparent instantaneous frequency oscillate, returning to zero at multiples of AQ. In reality, at these times, the true frequency is a multiple of the sweep width SW (see Appendix 8) and the motional phase factor is unity.

The fact that the motional modulation factor is unity at times equal to multiples of AQ implies that motion in the field gradient can be neglected at these special times (but not at any other time). A standard Hahn-echo, CPMG or stimulated echo sequence will therefore create spin echoes and stimulated echoes, provided the refocusing RF pulses are aimed to be placed at multiples of AQ. The RF pulses must be short compared to the time for which the motional phase factor is unity, which is of the order of the dwell time. This should not be a problem since dwell times of the order of hundreds of microseconds will typically be used.

The Stability of Motionally Modified Spin Echoes to Vibrations and Non-linearities in $G_z$ Motionally modified spin echoes (MMSE's) are stable to small object vibrations and to gradient non-linearities.

Proof: Consider first vibrations along the direction of motion. Because all spins in the object will experience the same vibration (rigid object) they will all accumulate the same phase shift between spin echoes as a result of the vibration. It follows that the spin echo will experience a constant phase shift. But a constant phase shift simply means that, in quadrature detection, the receiver phase needs to be adjusted to bring the echo back into phase. Moreover the image is calculated by taking the modulus so a constant phase shift makes no difference. Note however, that, in general the phase shift between successive spin echoes will not be the same, so any attempt to add or subtract successive echoes must take this into account. Provided $B_0$ field is homogeneous vibrations in the plane perpendicular to the motion will have no effect because $G_x.v_z=G_y.v_z=0$. Similar arguments apply to the effect of small non-linearities in G.

APPENDIX 4

The Simulation of MMSE's and Their Transformation

Figure 26:
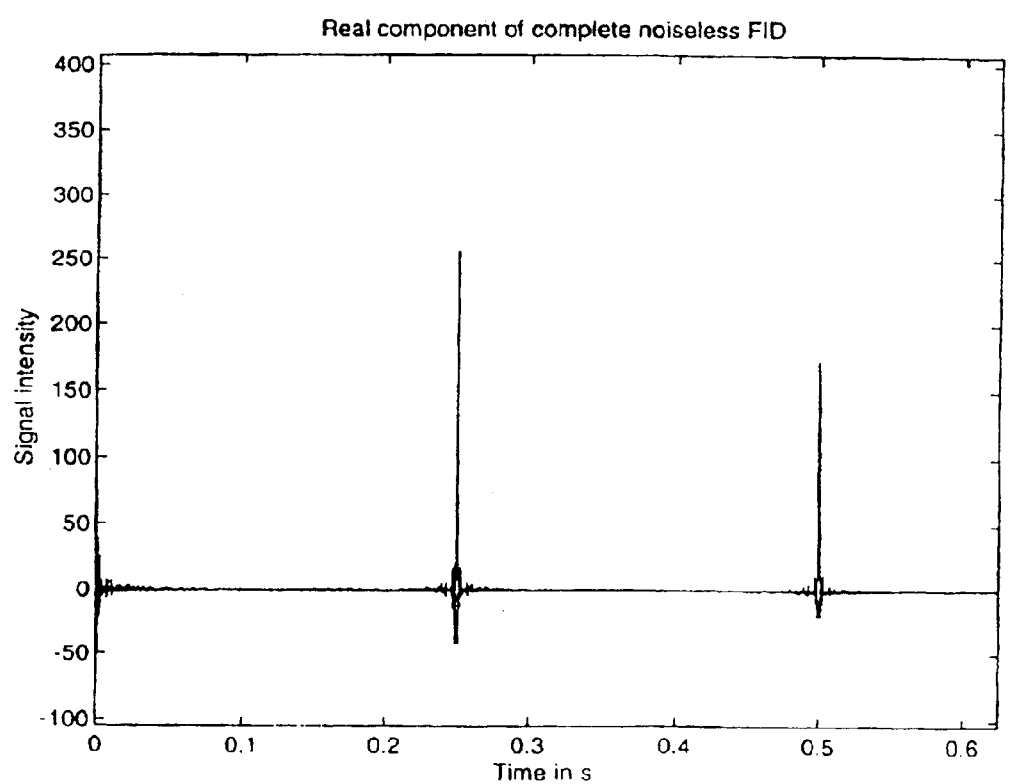
FIG. 26 shows a simulated signal of a moving object including an initial motionally modified free induction decay and the first two motionally modified spin echoes.
Figure 27:
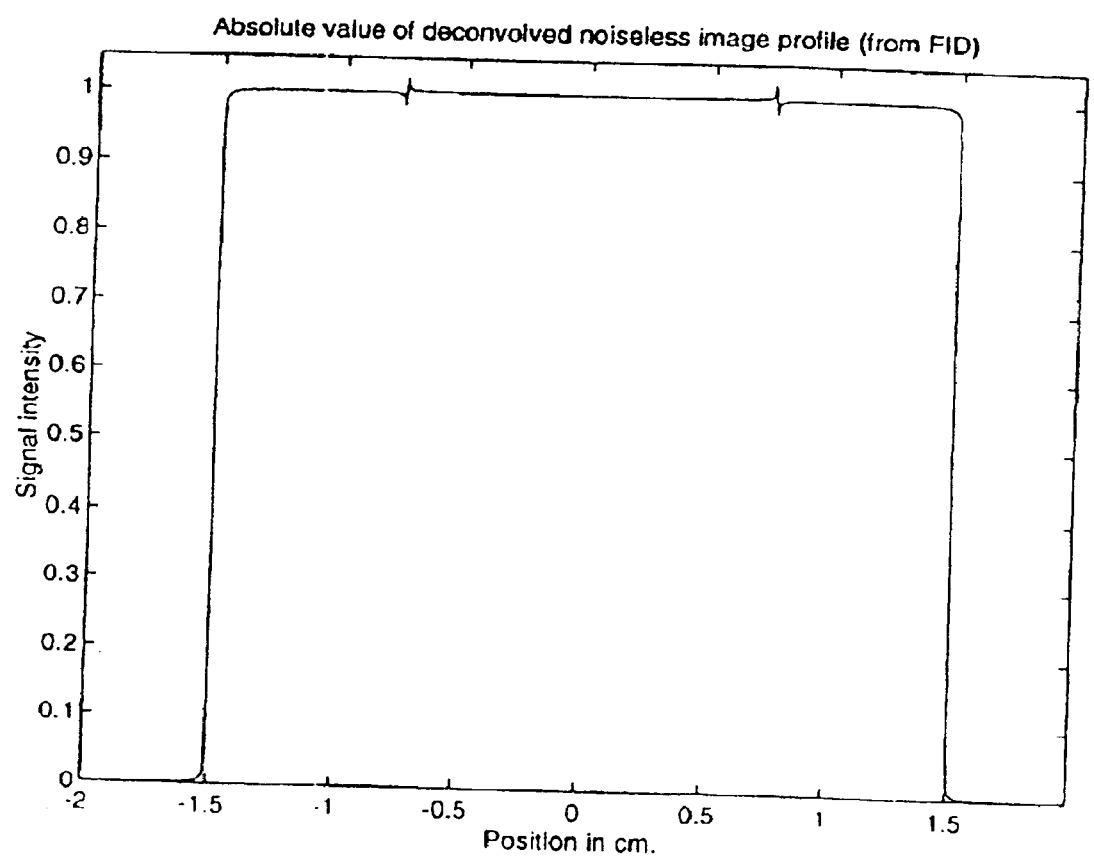
FIG. 27 shows the signal intensity values of a deconvolved noiseless image profile from the free induction decays of FIG. 26.
Figure 28:
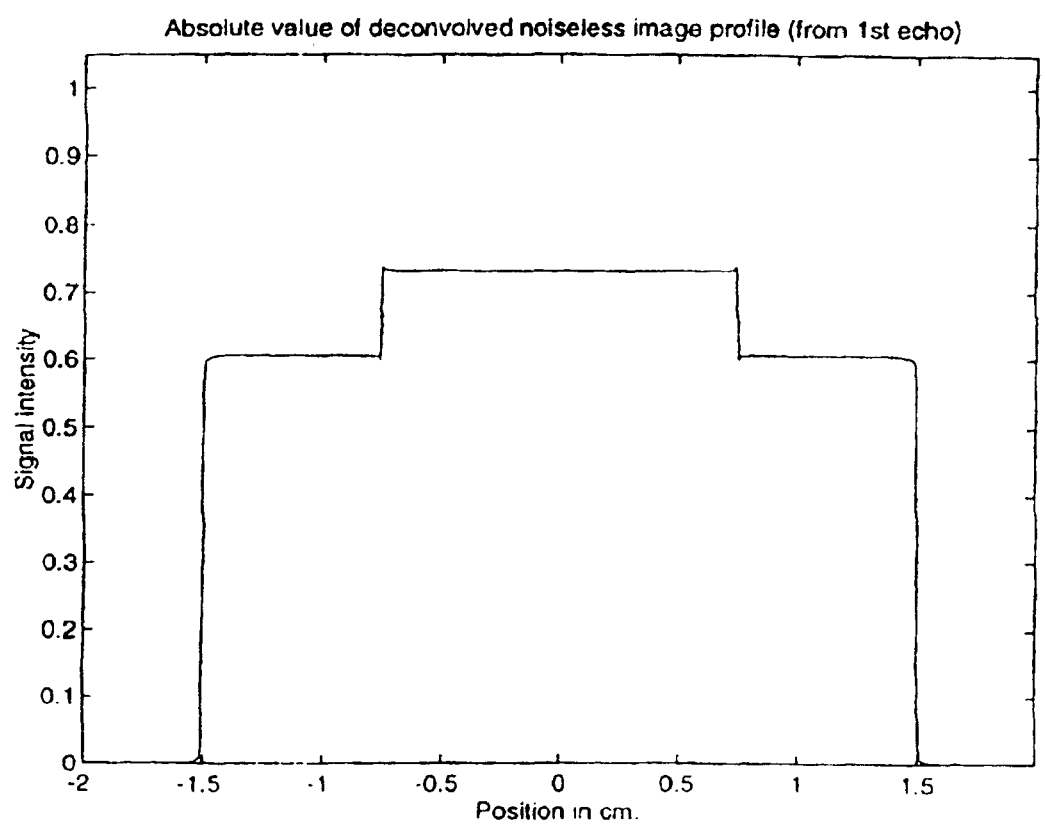
FIG. 28 shows the signal intensity values of a deconvolved noiseless image profile from the first spin echo of FIG. 26.
Figure 29:
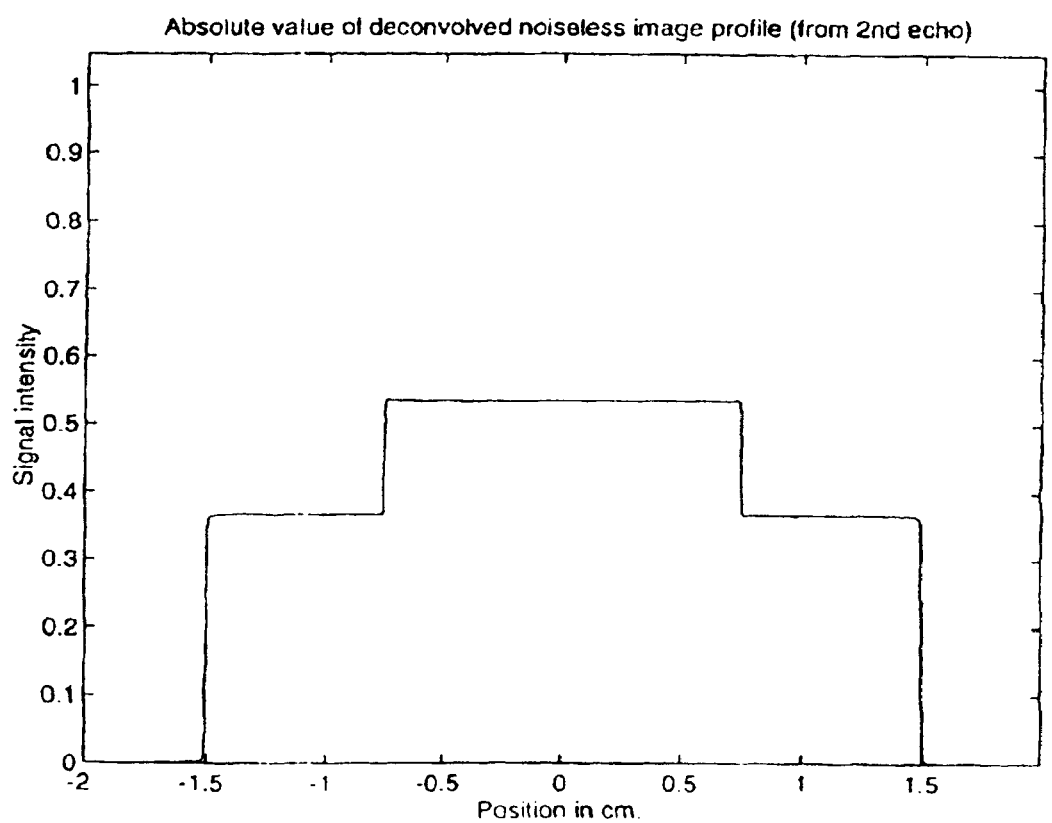
FIG. 29 shows the signal intensity values of a deconvolved noiseless image profile from the second spin echo of FIG. 26.
Figure 30:
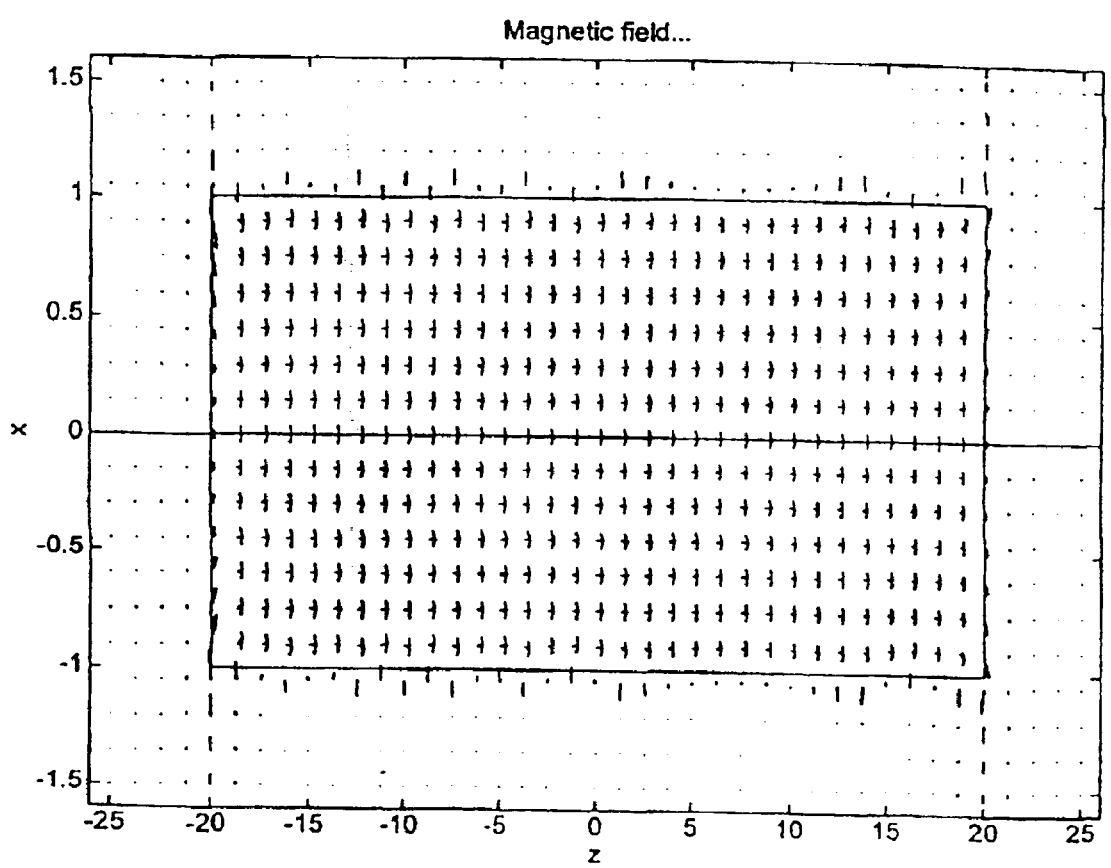
FIG. 30 shows a simulation of the magnetic field direction as a function of x and z spatial co-ordinates for a $G_z$ unit of the present invention.
Figure 31:
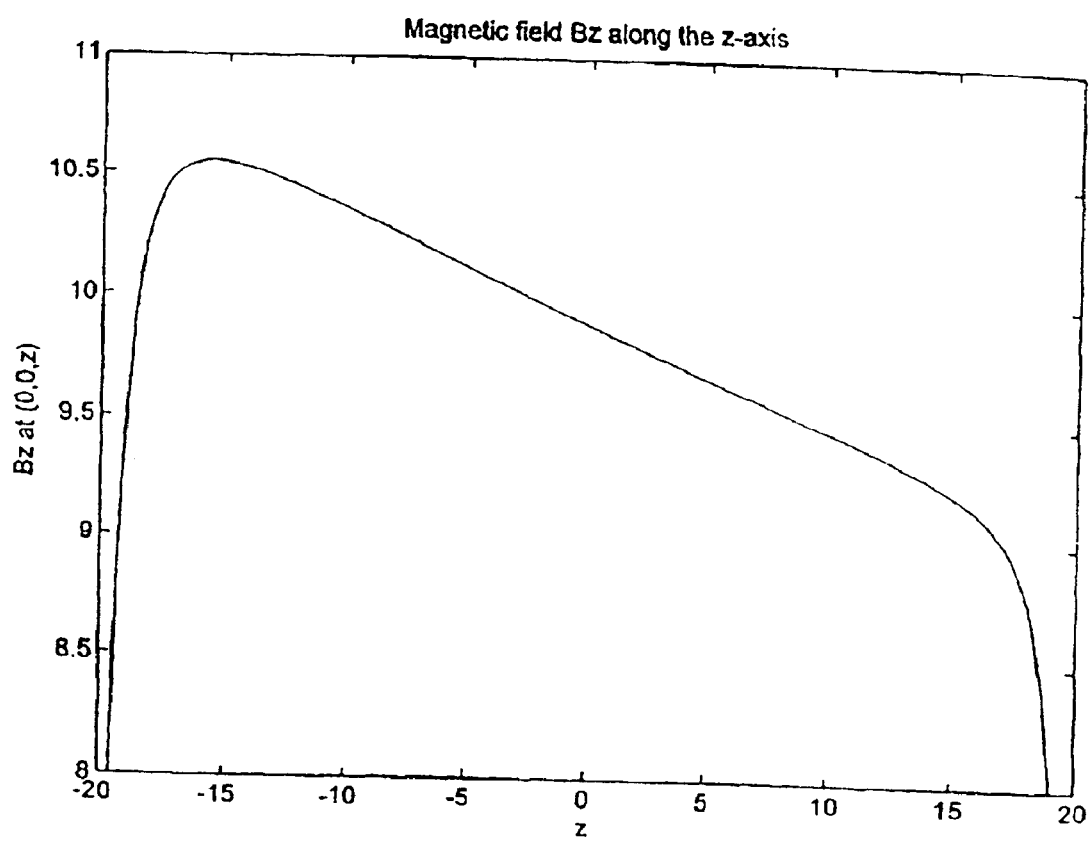
FIG. 31 shows a simulation of the magnetic field strength $B_z$ along the z axis as a function of z, with x=0, for the $G_z$ unit of FIG. 30.
Figure 32:
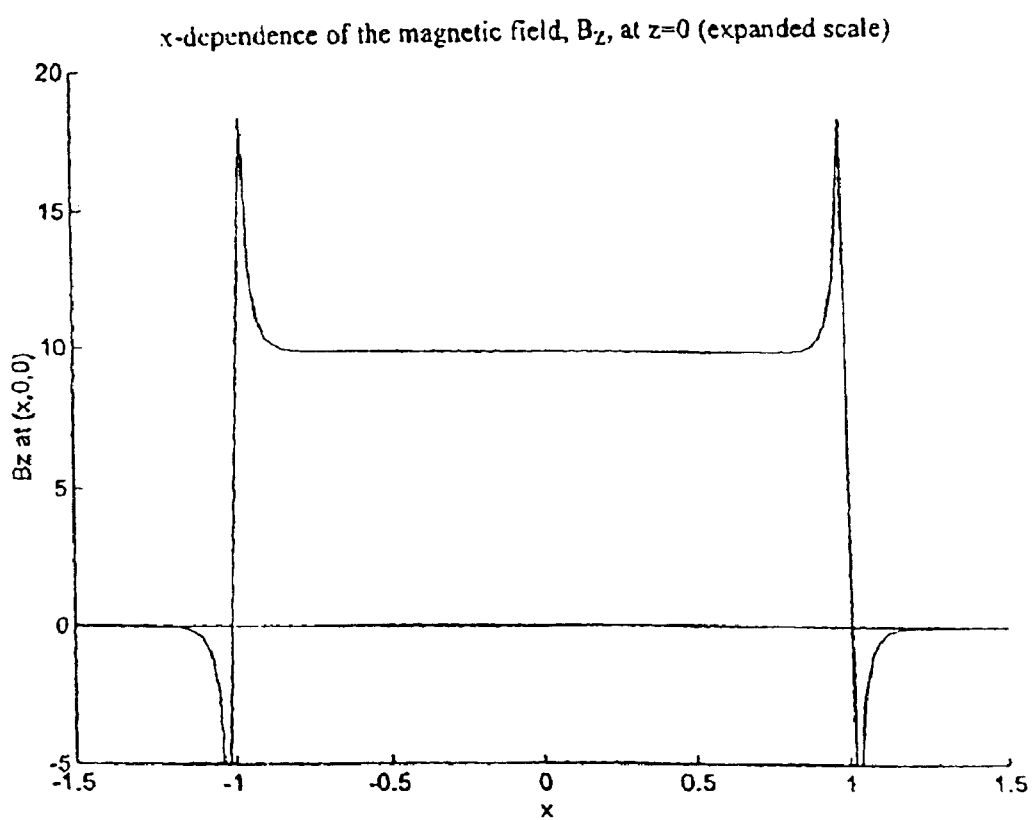
FIG. 32 shows a simulation of the magnetic field strength $B_z$ as a function of x, with z=0, for the $G_z$ unit of FIG. 30.
Figure 33:
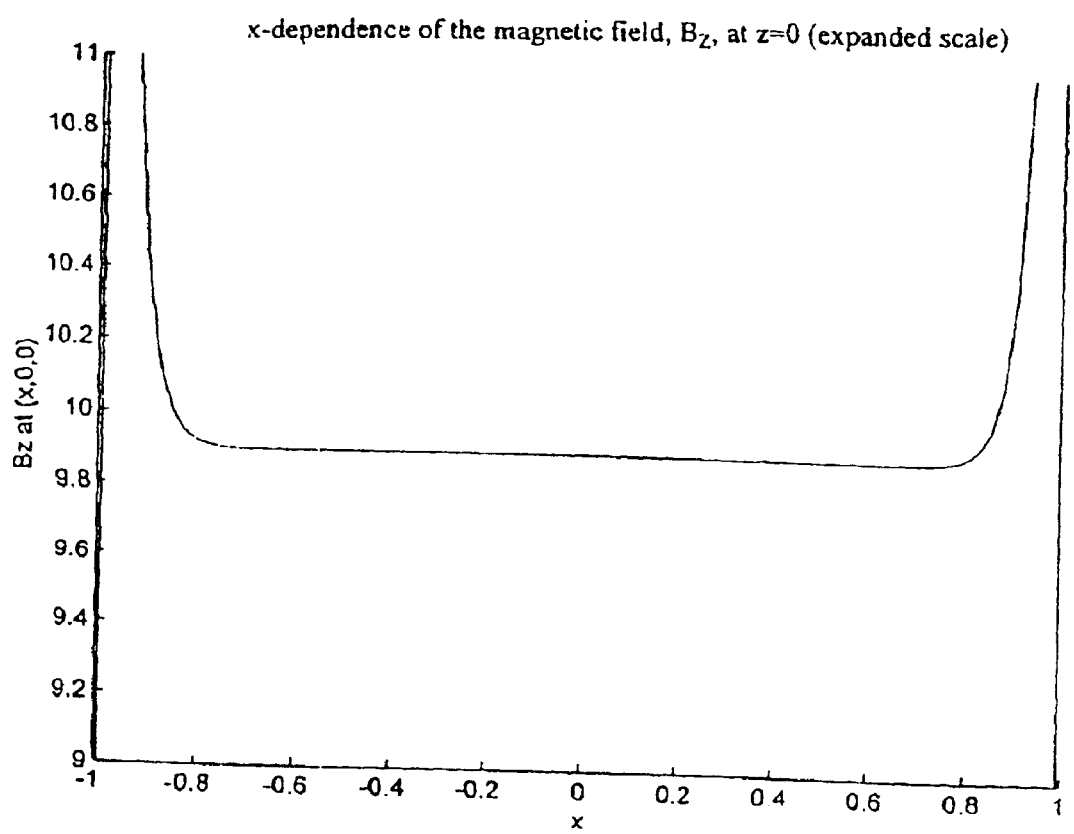
FIG. 33 shows a simulation of the magnetic field strength $B_z$ as a function of x, with z=0, for the $G_z$ unit of FIG. 30.
Figure 34:
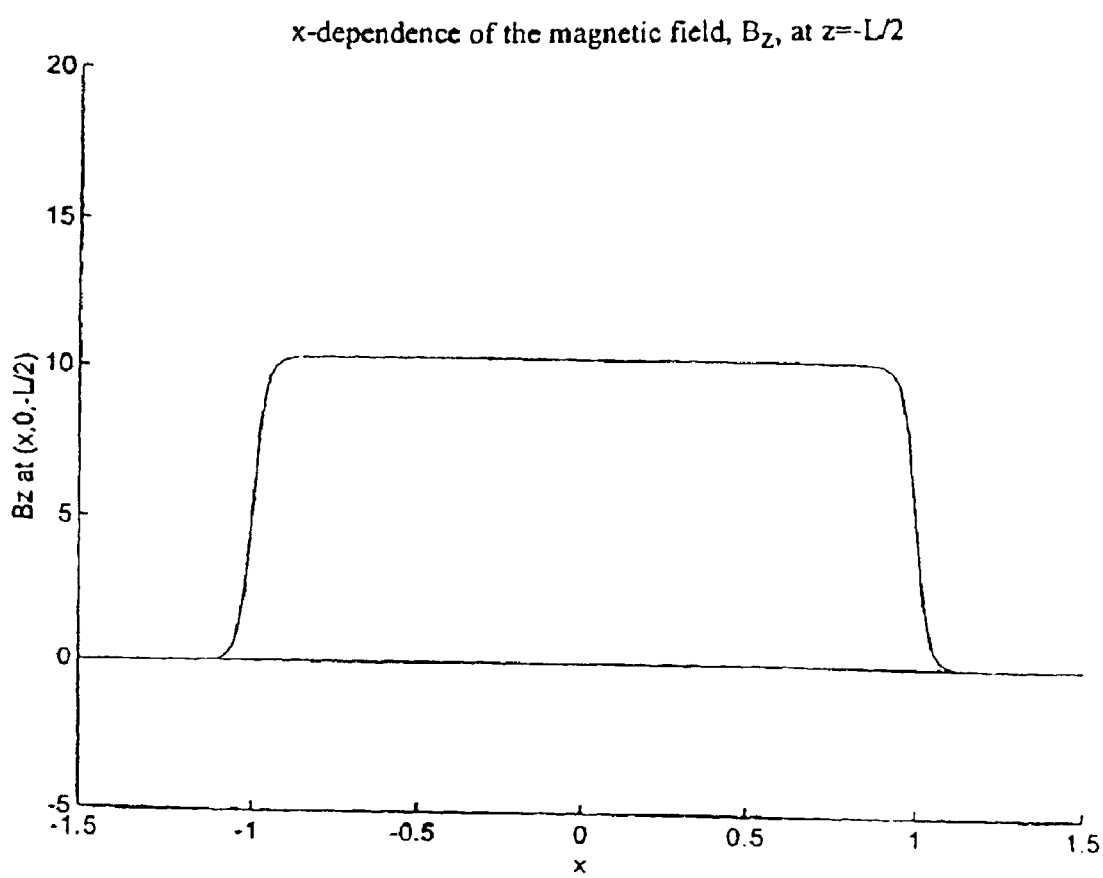
FIGS. 34 and 35 show a simulation of the magnetic field strength $B_z$ as a function of x, with z=−L/2, for the $G_z$ unit of FIG. 30.
Figure 35:
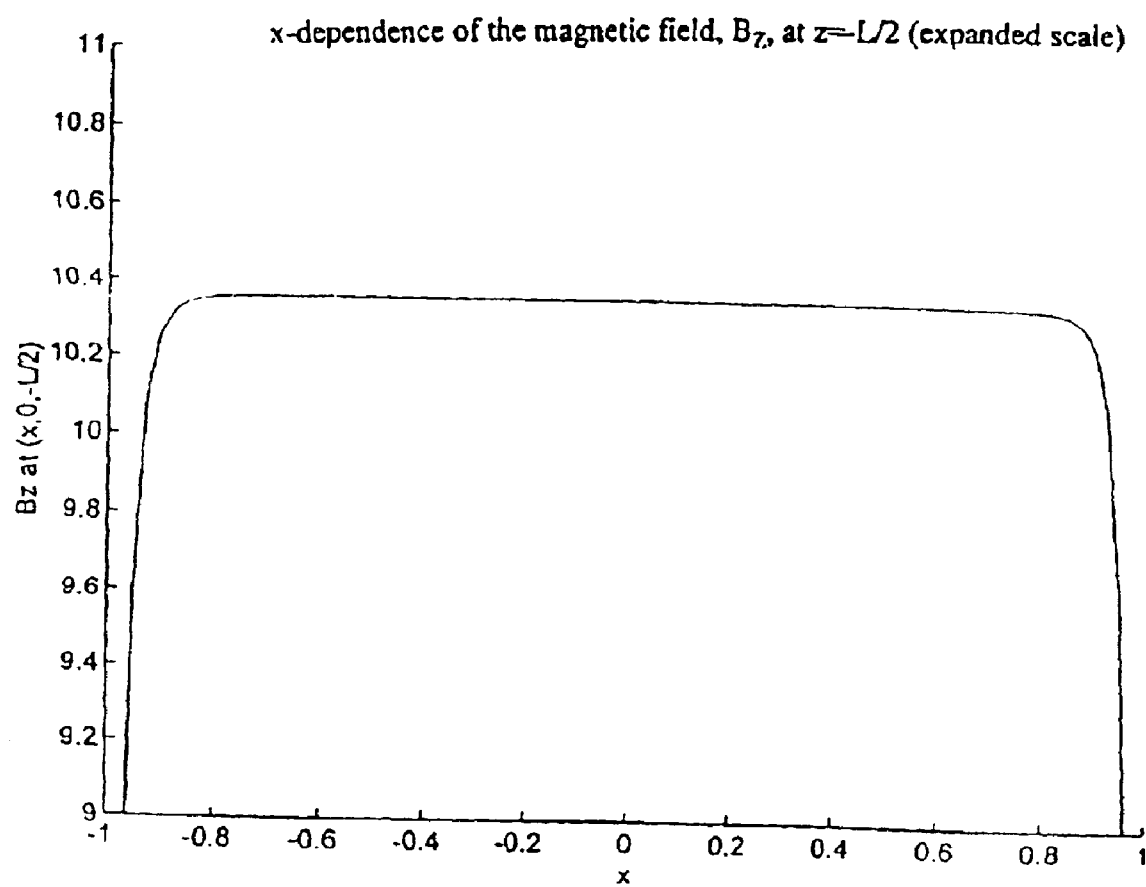
Figure 36:
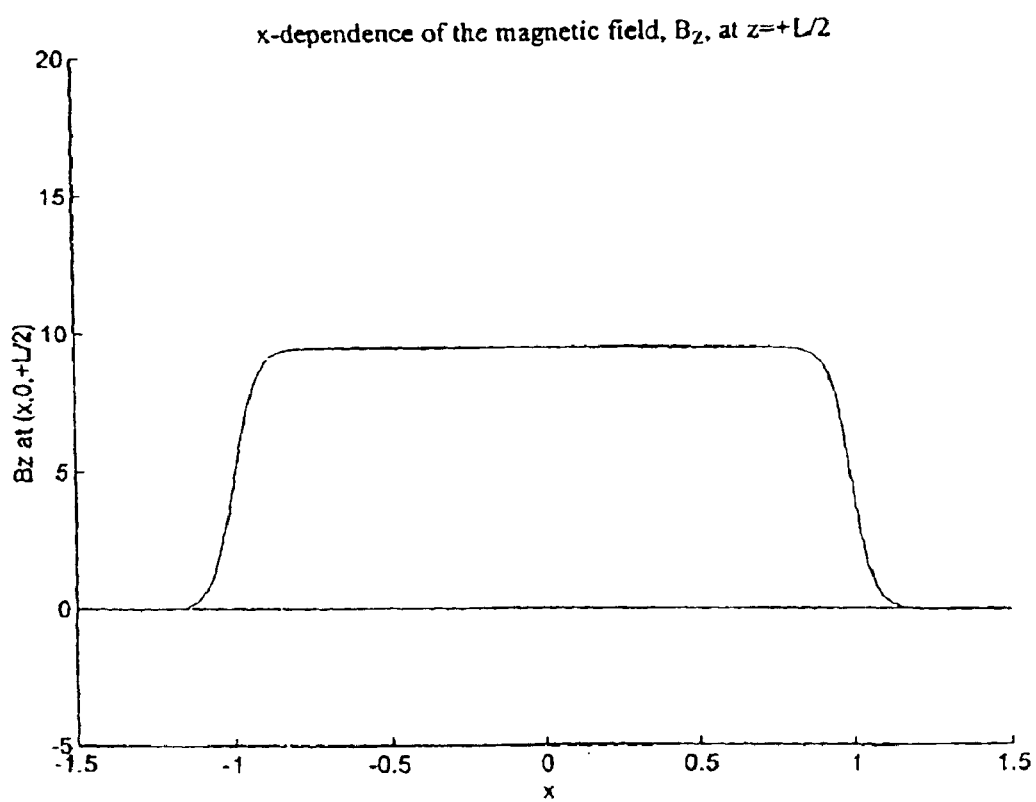
FIGS. 36 and 37 show a simulation of die magnetic field strength $B_z$ as a function of x, with z=+L/2, for the $G_z$ unit of FIG. 30.
Figure 37:
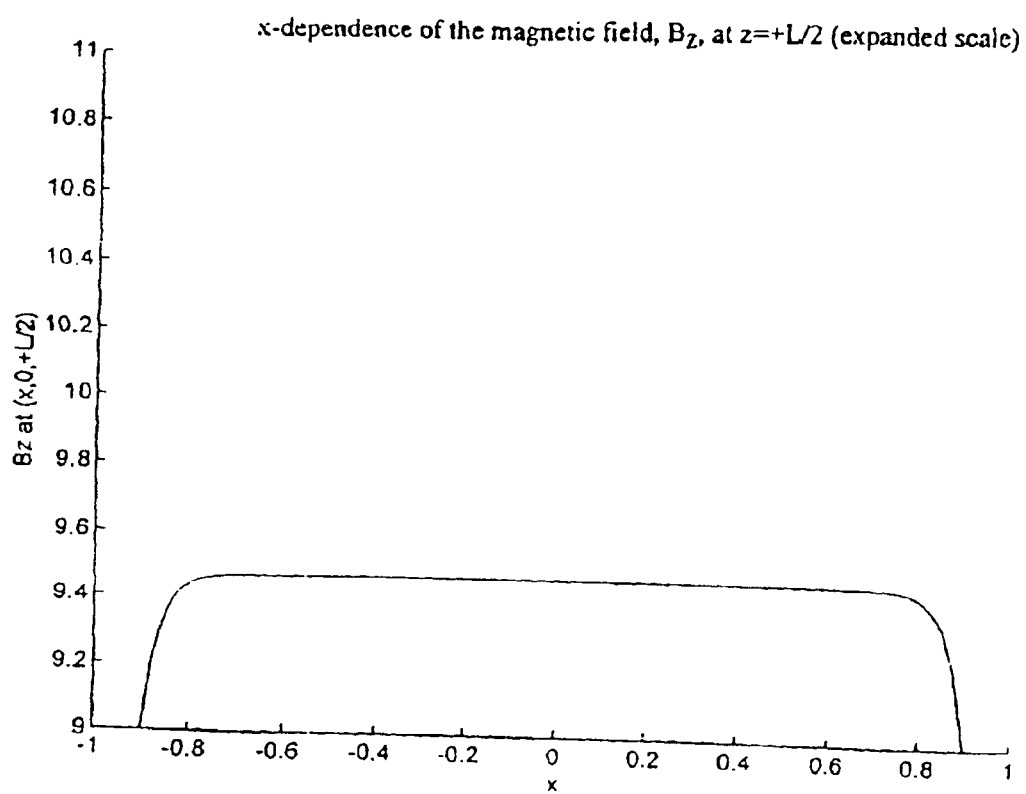
Figure 38:
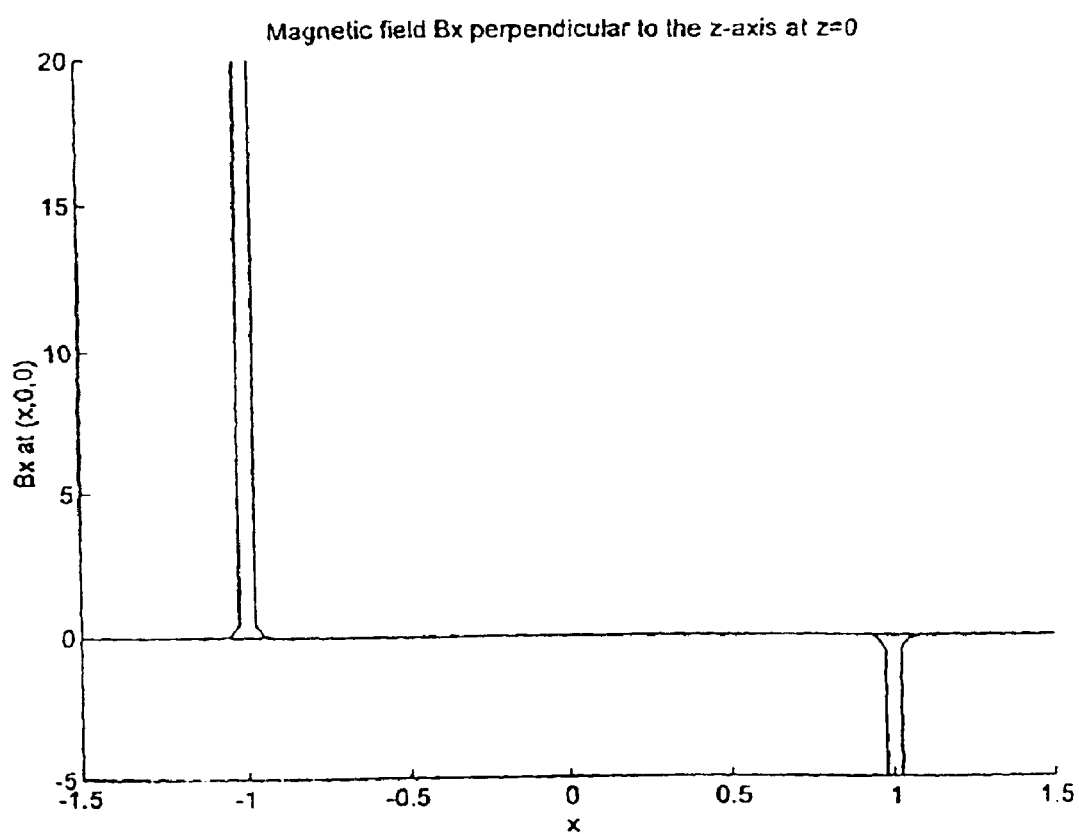
FIG. 38 shows a simulation of the magnetic field strength $B_x$ perpendicular to the z axis as a function of x, with z=0, for the $G_z$ unit of FIG. 30.
Figure 39:
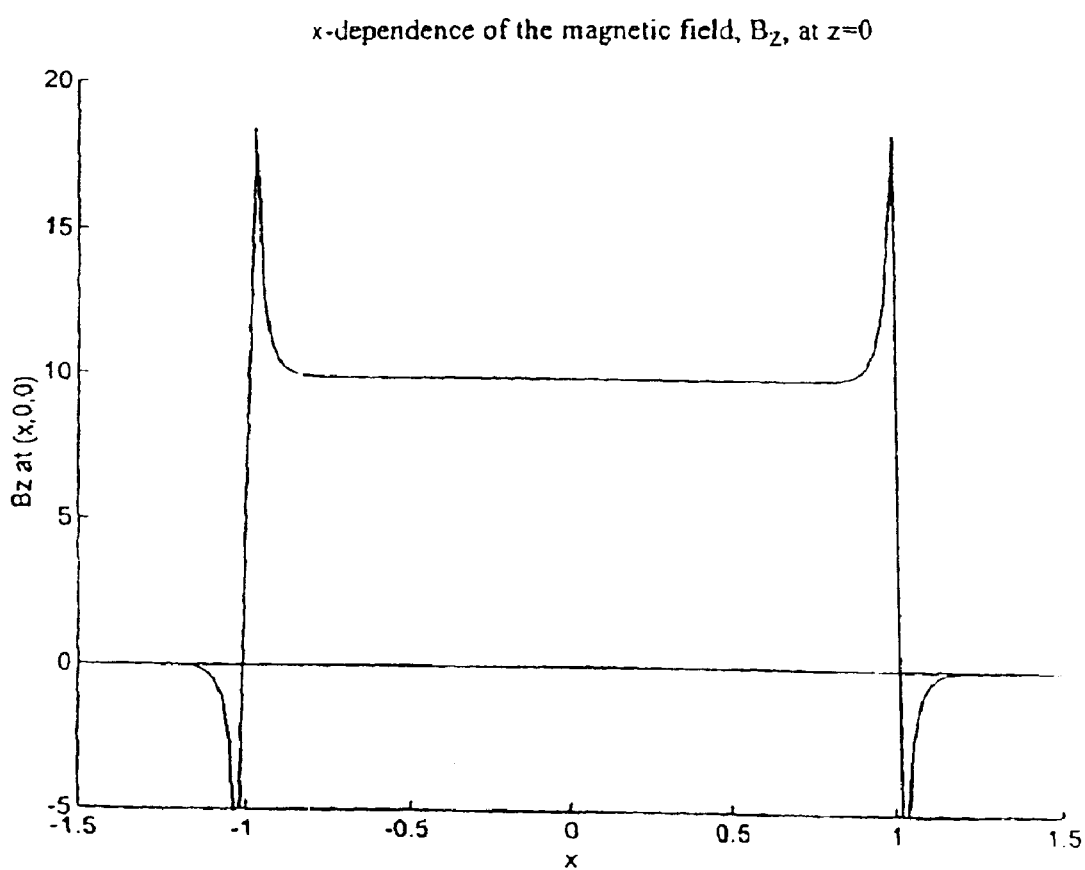
FIG. 39 shows a simulation of the magnetic field strength $B_z$ as a function of x, with z=0, for the $G_z$ unit of FIG. 30.
Figure 40:
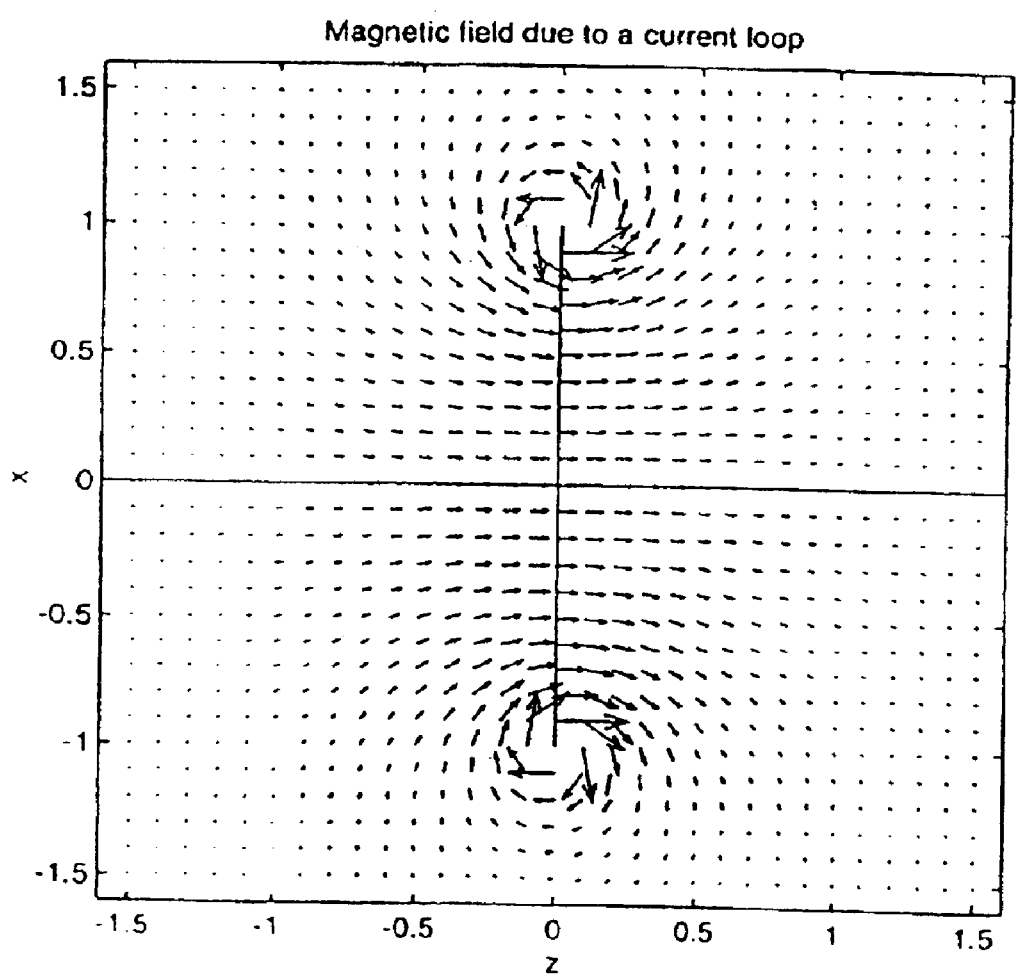
FIG. 40 shows a simulation of the magnetic field direction and strength as a function of x and z spatial co-ordinates for a $G_x$ unit of the present invention.
Figure 41:
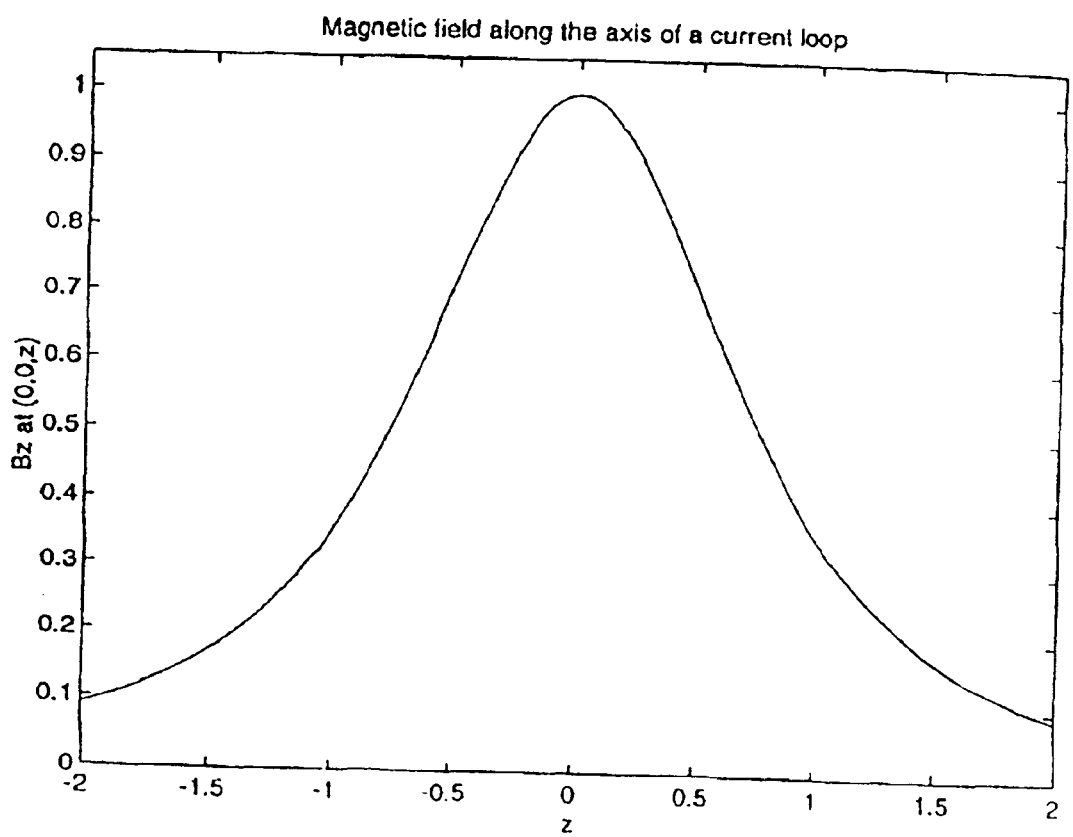
FIG. 41 shows a simulation of the magnetic field strength $B_z$ along the axis of a current loop as a function of z, at x=0, for the $G_x$ unit of FIG. 40.
Figure 42:
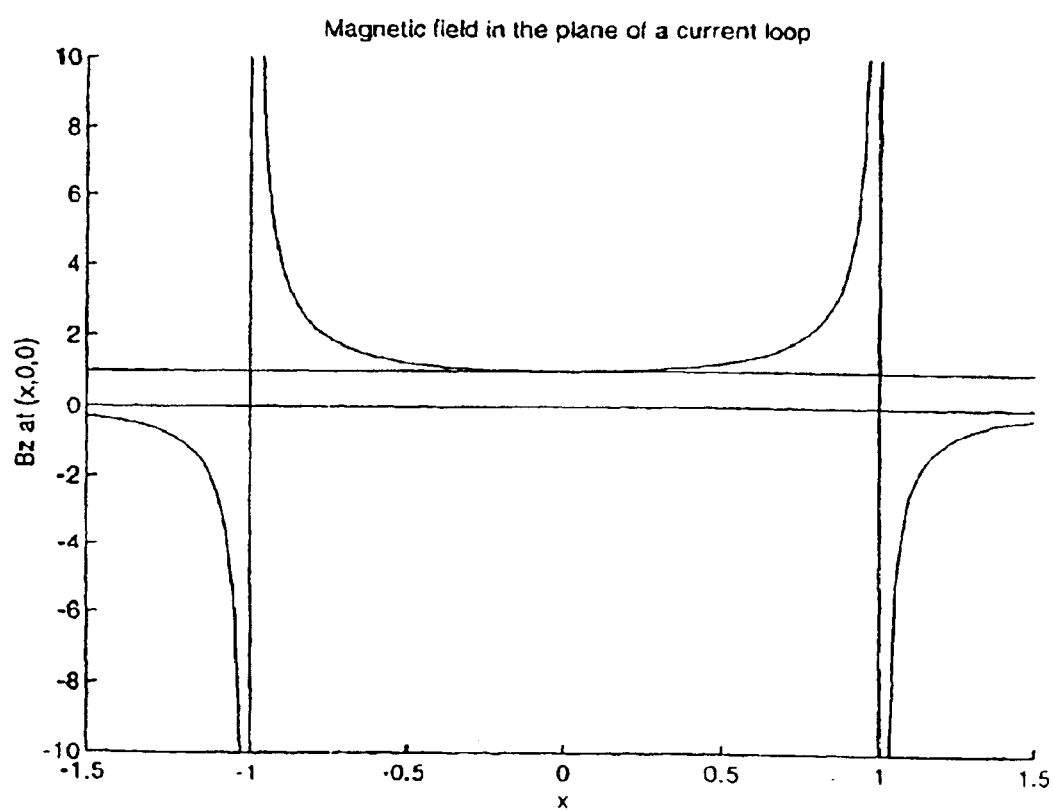
FIG. 42 shows a simulation of the magnetic field strength $B_z$ in the plane of a current loop as a function of x, at z=0, for the $G_x$ unit of FIG. 40.
Figure 43:
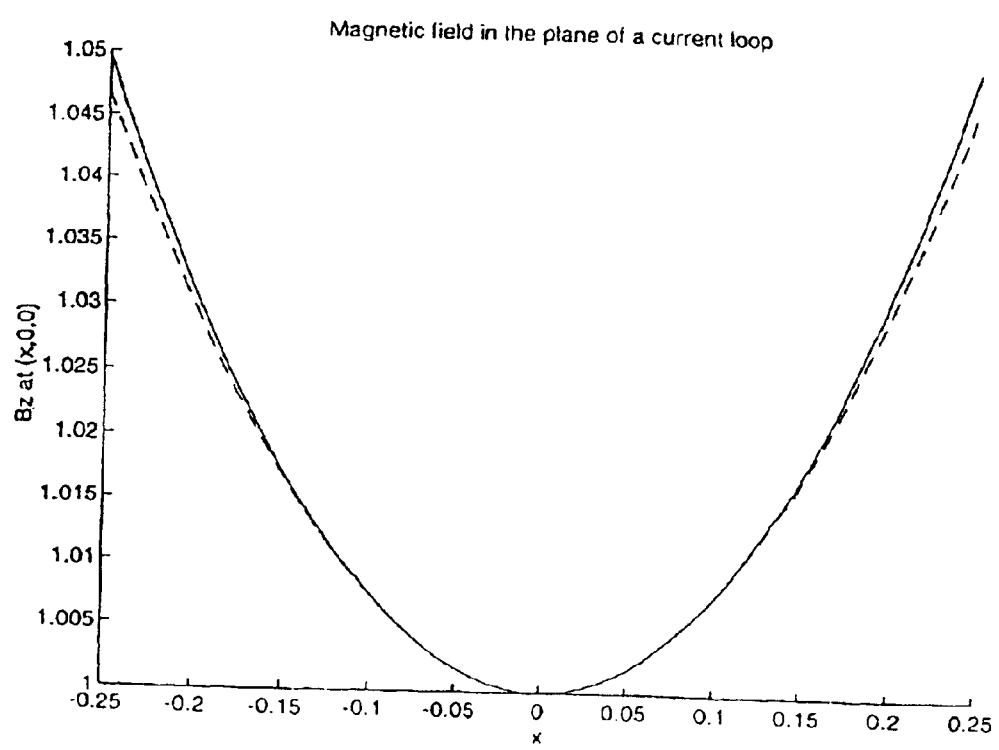
FIG. 43 shows a simulation of the magnetic field strength $B_z$ in the plane of a current loop as a function of x, at z=0, for the $G_x$ unit of FIG. 40.
Figure 44:
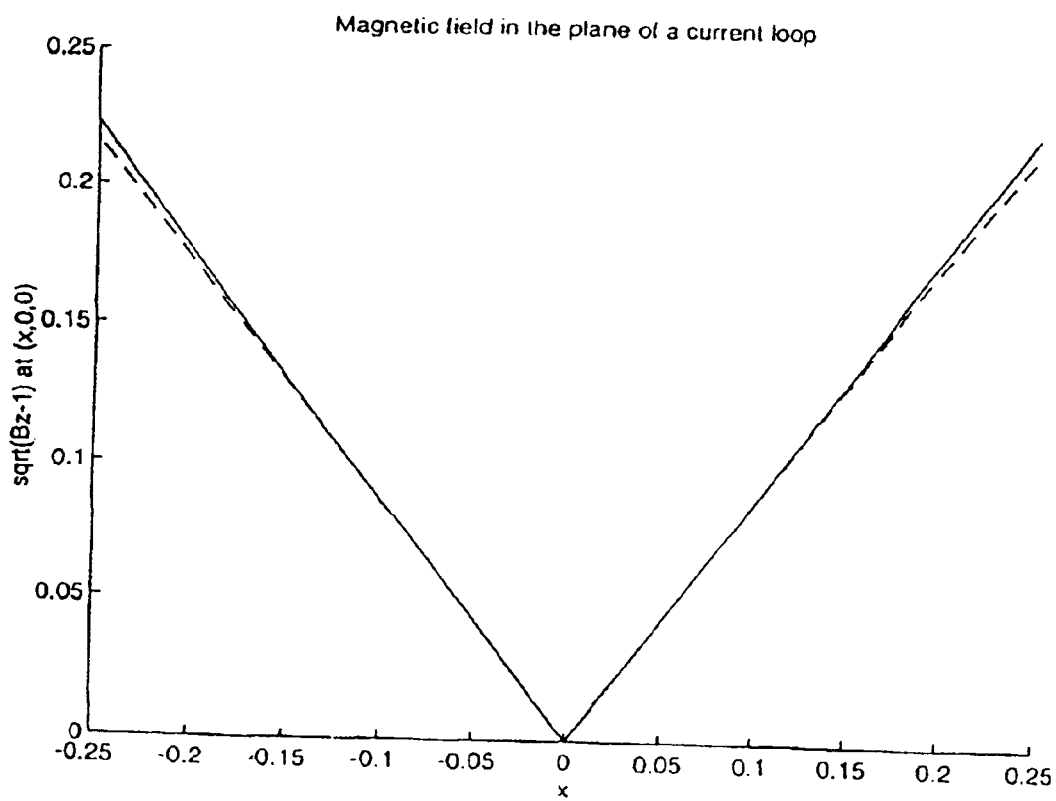
FIG. 44 shows a simulation of the square root of magnetic field strength $B_z-1$ in the plane of a current loop as a function of x, at z=0, for the $G_x$ unit of FIG. 40.

FIGS. 26 to 29 show the results of simulating the imaging of a moving cuboid shaped object with the CPMG pulse sequence (only the first two echoes are included). The $T_2$ of the outer quarters of the object is assumed to be shorter than that for the central half. FIG. 26 shows the simulated signal, including the initial MMFID and the first two MMSE's. The image of FIG. 27 is obtained from the MMFID by the method described previously and, as expected, shows no $T_2$ contrast. The subsequent images of FIGS. 28 and 29 are obtained from the first and second MMSE's respectively and show increasing $T_2$ weighted contrast.

APPENDIX 5

Simulated Field Gradients Within a $G_z$ Unit

We wish to create a linear field gradient, $G_z$, within a solenoid by using a non-uniform distribution of current coils along it. We must therefore compute the field, $B_z$, along the z-axis of N current loops or coils distributed along the axis at $z_1, z_2, \ldots z_N$. This can be done using the formula, $$B_z(z)=\Sigma_{i=1}^{N} 1/\{1+(z-z_i)^2\}^{3/2}$$

We now show that if the distances between coils are in an arithmetic progression, the field gradient is linear.

Distribute N current loops or coils along the z-axis between $z=+/-L$ in such a way that the distances between them form an arithmetic progression. Let the coils be situated at $z_1, z_2, \ldots z_N$, such that, for the first coil $z_1=-L$, and for the last coil, $z_{N+1}=+L$, (N>=2). Let the distance between $z_i$ and $z_{i+1}$ be $s_i$, i.e. $s_i=z_{i+1}-z_i$.

Then $$\Sigma_{i=1}^{j-1}s_i=\Sigma_{i=1}^{j-1}z_{i+1}-\Sigma_{i=1}^{j-1}z_i=\Sigma_{i=2}^{j}z_i-\Sigma_{i=1}^{j-1}z_i=z_j-z_1$$

therefore $$z_j=z_1+\Sigma_{i=1}^{j-1}s_i$$

The distances $s_i$ are chosen to be in arithmetic progression.

Let $s_1=\alpha d$, where $d$ is the increment and $\alpha>0$ $s_2=(\alpha+1)d$

. . .

$s_i=(\alpha+i-1)d$

Then $z_j=z_1+\Sigma_{i=1}^{j-1}(\alpha+i-1)d$ $z_j=z_1+\{2(\alpha-1)+j\}(j-1)d/2$ Putting j=N $L=-L+\{2(\alpha-1)+N\}(N-1)d/2$ Hence $d=4L/\{2(\alpha-1)+N\}(N-1)$ and $z_j=\{2(\alpha-1)+j\}(j-1)d/2-L$ Note that the length of the solenoid, L, is used as input when calculating the winding spacing. In principle L can be made as long as needed to acquire the image of the moving object. Representative examples, produced by a MATLAB program to calculate the field using these expressions, are shown in FIGS. 30 to 39 and these demonstrate the linearity of the $G_z$ gradient, as well as the homogeneity of the field in the x-y plane.

APPENDIX 6

Calculation of the Field Gradients Created by a Single Current Loop (the Gx Unit)

A MATLAB program has been written to calculate the magnetic field due to a circular current loop or coil centred at the origin in the x-y plane. This comprises the $G_x$ unit. Simulations of the magnetic field so derived are shown in FIGS. 40 to 44. Note the non-linear $G_x$ and $G_z$ gradients created by this unit.

APPENDIX 7

Extraction of the Velocity Distribution in a Flowing Fluid from an MMFID

Consider a fluid undergoing steady flow down a straight tube. Transverse magnetisation is excited in a thin layer of thickness, δ, in the x-y plane transverse to the direction of motion z, using a soft, shaped radiofrequency pulse in a field gradient $G_z$. For simplicity in the mathematical analysis we assume that the thickness is equal to a single voxel. The initial position of the excited layer is labelled r(0). The fluid elements, labelled i, within the layer each have a uniform velocity $v_i$ such that there is a velocity distribution $p(v_i)$ normalised so that, $$\Sigma_i p(v_i) = 1$$

The signal S(t) is then given by, $$S(t) = \exp\{i 2\pi \gamma Gr(0) t\} \Sigma_i p(v_i) \exp\{i 2\pi \gamma G v_i t^2 / 2\}$$

Note that the first factor is the same for all spins provided the initial thickness corresponds to one voxel. This factor can therefore be eliminated along with the resonance frequency by the demodulator. It follows that, $$S(t) = \Sigma_i p(v_i) \exp\{i 2\pi \gamma G v_i t^2 / 2\}$$

For a continuous velocity distribution this becomes, $$S(t) = \int dv\, p(v) \exp\{i 2\pi \gamma G v t^2 / 2\} \quad [A7.1]$$

Inversion of this Relationship:

Let $T = \pi \gamma G t^2$. Then $dT/dt = 2\pi \gamma G t$ and we assume the function S(t) in the transformed variable is s(T). It follows that $$s(T) = \int dv\, p(v) \exp\{i v T\}$$

This is a Fourier transform, so can be inverted:

$$p(v) = \int dT\, s(T) \exp\{-i v T\}$$

or $$p(v) = 2\pi \gamma G \int dt\, t\, S(t) \exp\{-i \pi \gamma G v t^2\} \quad [A7.2]$$

Equation [A7.2] is the desired relationship, showing how the velocity distribution p(v) can be obtained from the signal S(t).

Consistency Check:

This makes use of the following standard mathematical relationships:

$$\delta(w - w') = \int dt\, \exp[i(w - w')t] \quad [A7.3]$$

and $$\delta(w^2 - w'^2) = (1/2w')[\delta(w - w') + \delta(w + w')] \quad [A7.4]$$

and $$\delta(aw) = (1/a)\delta(w) \quad [A7.5]$$

Substituting equation [A7.2] into [A7.1] gives $$S(t) = \int dv\, 2\pi \gamma G \int dt'\, t'\, S(t') \exp\{\pi \gamma G v(t^2 - t'^2)\}$$

$$S(t) = 2\pi \gamma G \int dt'\, t'\, S(t') \int dv\, \exp\{i\pi \gamma G v(t^2 - t'^2)\}$$

Using relation [A7.3]:

$$S(t) = 2\pi \gamma G \int dt'\, t'\, S(t') \delta\{\pi \gamma G(t^2 - t'^2)\}$$

Using equation [A7.5]:

$$S(t) = 2\pi \gamma G \int dt'\, t'\, S(t') [1/\pi \gamma G] \delta(t^2 - t'^2)$$

Using equation [A7.4]:

$$S(t) = 2 \pi \gamma G \int dt'\, t'\, S(t') [1/\pi \gamma G](1/2t')[\delta(t - t') + \delta(t + t')]$$

But both t and t' must be >0, so the second delta function integral is zero. Therefore $$S(t) = \int dt'\, 2t'\, S(t')(1/2t') \delta(t - t') = S(t) \quad QED$$

The transformations are therefore consistent.

On-line Sensing of Fluid Rheology

For fluids undergoing steady flow down a cylindrical pipe under a steady pressure gradient there is a simple relationship between the velocity distribution p(v) and the radial velocity field v(r) and hence to fluid rheology. Some of these well-known relationships are summarised in the table below. The formal interrelationships between p(v) and v(r) for steady flow down a circular pipe are as follows:

Given p(v) Calculate v(r)

Let g(r) be the normalised radius distribution, i.e. g(r)dr is the volume fraction of the pipe having a radius between r and (r+dr). Then, if R is the pipe radius, $$g(r)dr = 2\pi r\, dr / \pi R^2 = 2r/R^2$$

such that $\int_0^R dr\, g(r) = 1$. Then $$p(v) dv = g(r) dr = 2r/R^2$$

Integrating this differential, assuming that the velocity on the wall at R is zero $$\int_0^{\Delta v} p(v) dv = \int_R^{r1} dr\, 2r/R^2 = (r1^2 - R^2)/R^2$$

where r1 is the radius corresponding to the velocity Δv. But the left hand integral can be written $p(v_{av}) \Delta v$ for small Δv, where $p(v_{av})$ is the mean of the spectrum between v=0 and v=Δv. Therefore $$p(v_{av}) \Delta v = (r1^2 - R^2)/R^2$$

or $$\Delta v (r1^2 - R^2)/R^2 p(v_{av}) \quad [A7.6]$$

Equation [A7.6] shows that, more generally, for a discrete set of points, $$\Delta v_j = (v_{j+1} - v_j) = -(r_{j+1}^2 - r_j^2)/R^2 p(v_{av,j}) \quad [A7.7]$$

where $r_1 = R$, $v_1 = 0$ and $$v_{av,j} = (v_j + v_{j+1})/2$$

Equation [A7.7] shows how the velocity profile, v(r), can be computed a(numerically) from an on-line measurement of p(v).

Given v(r) Calculate p(v)

The normalised signal given in equation [A7.1] can be written:

$$S(t) = (1/\pi R^2) \int_0^R dr \int_0^{2\pi} d\phi \, r \rho(r) \exp\{i 2\pi \gamma G v(r) t^2/2\} \text{ in real space.}$$

We assume a uniform fluid density, $\rho(r)$ 1,

The space integral can be transformed into a velocity space by

1. Calculating r(v) from v(r)
2. Noting that the integral is simply, $$S(t) = (1/\pi R^2) \int\int dv d\phi J(r,\phi/v,\phi) r(v) \exp\{i 2\pi \gamma G v t^2/2\}$$

where $J(r,\phi/v,\phi)$ is the Jacobean of the transformation:

But $J(r,\phi/v,\phi) = |(\partial r/\partial v)\phi|$ $$S(t) = (1/\pi R^2) 2\pi \int dv |(\partial r/\partial v)|_{100} |r(v)| \exp\{i 2\pi \gamma G v t^2/2\}$$

$$S(t) = (2/R^2) \int dv |(\partial r/\partial v)| r(v) \exp\{i 2\pi \gamma G v t^2/2\}$$

Comparison with equation [A7.1]

$$S(t) = \int dv p(v) \exp\{i 2\pi \gamma G v t^2/2\} \quad [A7.1]$$

shows that $$p(v) = (2/R^2)|(\partial r/\partial v)| r(v)$$

This equation shows how p(v) can be calculated from the theoretical velocity distributions, v(r), for different types of rheology:

| Rheological type | v(r) | p(v) |
|---|---|---|
| Newtonian fluid $\sigma = \mu(d\gamma/dt)$ $\mu$ is the shear viscosity | $v_{max}[1 - (r/R)^2]$ | $1/v_{max}$ |
| Power law fluid $\sigma = m (d\gamma/dt)^n$ | $v_{max}[1 - (r/R)^{[n+1/n]}]$ | $(2n/n + 1)(1/v_{max})$ $[1 - (v/v_{max})]^{\{(n-1)/(n+1)\}}$ |
| Plug flow | $v_{max}$ | $\delta(v - v_{max})$ |

APPENDIX 8

Typical Parameter Magnitudes

Here we illustrate how the magnitude of the $G_z$ field gradient is determined and present, by way of illustration, a physically reasonable set of parameter values for image acquisition.

All NMR parameters can be calculated from 4 independent parameters. These are

1) L, the length of the object to be imaged. This will usually be out of the control of the designer.
2) v, the object velocity. This will usually be determined by the industrial processing operator.
3) n, the number of points in the image that covers a distance L, and hence define the digitisation of the object (of length L) being imaged. The value of the integer n is arbitrary and need not be a power of 2.
4) N, the number of data points in the signal, and hence in the entire field of view of the one-dimensional image projection. N will be a multiple of 2 and will typically be 1024 or 2048. Also, $N \geq n$.

Other parameters can be calculated from this set of 4 parameters. These include:

The digital resolution, $\Delta z$, which is L/n.

The field of view (FOV), which is $N\Delta z = NL/n$.

The dwell time (the time between data points), which is $\Delta z/v$.

The image acquisition time, AQ, which is $N\Delta t$.

The sweep width, SW, (the frequency range covered by the entire image). $SW = 2\pi/\Delta t$ rad s$^{-1}$ or $1/\Delta t$ Hz.

The gradient $G_z$ which is SW/FOV.

The calculation of a set of physically reasonable parameters is presented below.

```
 1  % --- params.m ---
 2  %- Calculation of the parameters in a simulation of an
 3  % experiment to recover the image profile of a moving
 4  % sample by deconvolution.
 5  %- By KMW, Dec. 24, 1997.
 6
 7  % Set N, the time domain (must be a power of two)
 8  % N = the no. of time steps simulated
 9  %   = the no. of complex pts. in the MMFID
10  %   = the minimum no. of pts. in the image profile
11  N = 2048;
12
13  % Set M, the no. of units of spatial resolution (delta_z)
14  % across the sample. M must be <= N, so that the sample
15  % fits inside the field of view.
16  M = N-256;
17
18  % Set the length of the sample in the direction
19  %- of motion (z) in cm.
20  samplen = 4.0;
21
22  % Set the mean sample velocity v in cm/s.
23  v_mean = 32.0;
24
25  % Compute the spatial resolution in cm.
26  delta_z = samplen/M;
27
28  % Compute the field of view, or width of the image profile in cm.
29  fov = N*delta_z; % cm
30
31  % Compute the time increment (dwell time) in s, such that the
32  % sample moves one unit of spatial resolution per dwell time.
33  delta_t = delta_z/v_mean;
34
35  % compute the acquisition time in s.
36  acq = N*delta_t;
37
38  % Compute the sweep width by Nyquist's theorem.
39  sw = 1/delta_t;
40
41  % Compute the field gradient in Hz/cm.
42  % (N.B. 1 Maran gradient unit ~30 Hz/cm.)
43  g = sw/fov;
44
45  % Display the parameters.
46  disp('No. of pts. in time/frequency domains');
47  disp(N);
48  disp('NO. of pts. across sample');
49  disp(M);
50  disp('Sample length in cm.');
51  disp(samplen);
52  disp('Mean sample velocity in cm/s.');
53  disp(v_mean);
54  disp('Spatial resolution in μm.');
```

-continued

```
55  disp(delta_z*1e4);
56  disp('Dwell time in us.');
57  disp(delta_t*1e6);
58  disp('Acquisition time in s.');
59  disp(acq);
60  disp('Field of view of image profile in cm.');
61  disp(fov);
62  disp('Sweep width of image profile in kHz.');
63  disp(sw*1e-3);
64  disp('Minimum length of sampling region to acquire MMFID,
       in cm.');
65  disp(fov+samplen);
66  disp('Field gradient in kHz/cm. and Maran g.u. (approx.)');
67  disp([g*1e-3 g/30']);
```

No. of pts. in time/frequency domains
    2048
No. of pts. across sample
    1792
Sample length in cm.
    4
Mean sample velocity in cm/s.
    32
Spatial resolution in um.
    22.3214
Dwell time in us.
    69.7545
Acquisition time in s.
    0.1429
Field of view of image profile in cm.
    4.5714
Sweep width of image profile in kHz.
    14.3360
Minimum length of sampling region to acquire MMFID, in cm.
    8.5714
Field gradient in kHz/cm. and Maran g.u. (approx.)
    3.1360    104.5333

APPENDIX 9

In this appendix we define exemplary maximum and/or minimum limits on the magnitude of key physical quantities in the imaging experiments. These key physical quantities include:

1) The minimum length of the $B_0$ unit, the RF unit in FIG. 2 and of the Gz unit in FIG. 3.

FIG. 45 shows that, in a simple Hahn echo pulse sequence, the object travels a distance of $3v \times AQ$ between excitation and acquisition of both the rising and decaying parts of the motionally modified spin echo. This means that the minimum length of the $B_0$ unit, the RF unit (in FIG. 2) and of the Gz unit (in FIG. 3) is preferably $4v \times AQ$.

2) The minimum filter width (FW)

FIG. 45 shows that the object travels a distance equivalent to three times the sweep width (SW) during the simple Hahn echo pulse sequence. If the hardware is unable to change the resonance frequency of the radiofrequency pulses during the pulse sequence, then this means that the filter width is preferably at least 4×SW to acquire both the motionally modified FID of the 90 degree and the motionally modified spin echo of the 180 degree pulse. In other words $$\text{Filter width} \geq 4 \times SW \qquad [A9.1]$$

3) The maximum duration of the radiofrequency pulses

It is important that the radiofrequency pulses are of sufficiently short duration that all parts of the object are equally excited during the whole signal acquisition process. The excitation bandwidth of a square 90 degree radiofrequency pulse is approximately $1/(90°$ pulse duration$)$. Because a square radiofrequency pulse in the time domain gives a sinc function excitation bandshape in the frequency domain it is best to include a factor of in this expression to ensure that only the central lobe of the sinc function 5 is used to excite the object. This means that the excitation bandwidth of the 90 degree pulse is effectively $1/(5 \times 90°$ pulse duration$)$. FIG. 45, for the case of the simple Hahn echo pulse sequence, shows that the object travels a distance equivalent to 2× the sweep width (SW) during the interval between the two pulses. This means that the excitation bandwidth needs to be at least 3× the sweep width to encompass the whole of the object during its motion. This means that $$\text{Excitation bandwidth} \geq 3 \times SW$$

Noting that SW=1/DW where DW is the dwell time, this states that $$1/[5 \times (90° \text{ pulse duration})] \geq 3 \times (1/DW)$$

$$(90° \text{ pulse duration}) \leq DW/15 \qquad [A9.2]$$

This shows that the maximum 90 degree radiofrequency pulse duration is DW/15 and the maximum 180 degree pulse length is 2×DW/15. Radiofrequency pulses longer than this may not uniformly excite the whole object in the imaging sequence.

4) The maximum field gradient, Gz

It is well known that the attenuation in the amplitude of the spin echo in a Hahn echo experiment in the presence of a constant gradient, G, is given as, $$S(2\tau)/S(0) = \exp\{-2\gamma^2 G^2 D \tau^3/3\} \qquad [A9.3]$$

where $\gamma$ is the gyromagnetic ratio of the proton and $\tau$ is the 90–180° pulse spacing. Reference to FIG. 45 shows that the time "$\tau$" in the on-line imaging experiment is equal to AQ so that the echo attenuation arising from diffusion in the applied field gradient is $$S(2AQ)/S(0) = \exp\{-2\gamma^2 G_z^2 D(AQ)^3/3\} \qquad [A9.4]$$

In certain circumstances this will set an upper limit on the magnitude of the applied field gradient, Gz. In most industrial applications a weak gradient will be used so this will not be an important limiting factor.

APPENDIX 10

An Experimental Protocol for Adjusting the Applied Field Gradient, Gz

To prevent distortions of the images acquired by transforming motionally modified Free Induction Decays (MMFID's) or spin echoes (MMSE's) it is necessary that the magnitude of the applied field gradient, Gz, is adjusted to meet the criterion derived in Appendix 3, namely that, $$AQ = N\Delta t = [2\pi N/\gamma G.v]^{1/1} \qquad [A10.1]$$

Figure 46:
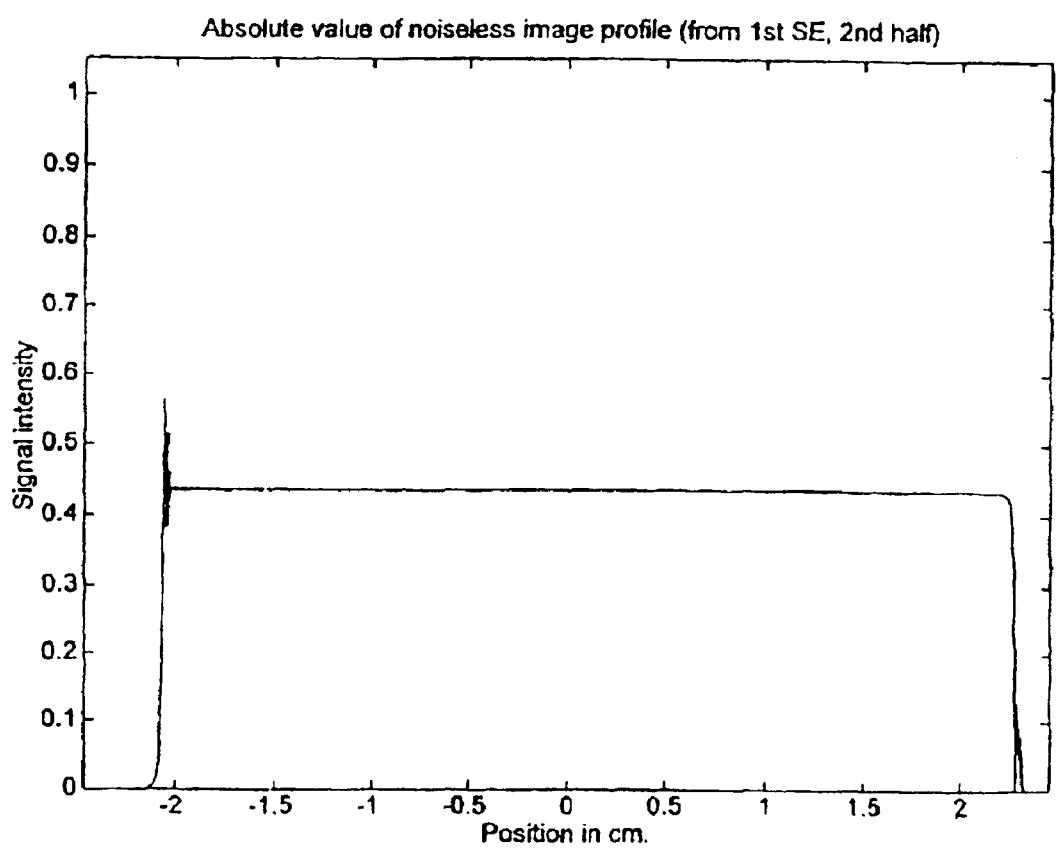
FIG. 46 shows the distortion in the output as a function of z derived from transforming the first motionally modified spin echo in a Hahn spin echo sequence, from a rectangular object, where the gradient field deviates from the ideal value by +1%.

This equation can be used to calculate the required magnitude of the applied field gradient, G, for: any given sample velocity, v, and acquisition time, AQ. However, in an actual experiment, the magnitude of the applied gradient, G, will need to be slightly adjusted (or tuned) experimentally so as to match this condition and minimize image distortions. In practice this is straightforward because computer simulations with the MATLAB programmed show that a gradient that is slightly too small gives rise to distortions (rapid oscillations) on the left hand side of the image of a rectangular shaped object (phantom) obtained by transforming the motionally modified spin echo (MMSE) in the Hahn spin echo sequence. This is seen in the simulation in FIG. 46, where a gradient only 1% larger than the ideal value derived from equation [A10.1] has been used. Conversely, a gradient that is slightly too small gives rise to distortions on the right hand side of the image. This is shown in FIG. 47 where a gradient that is 2% smaller than the exact value has been used in the simulation. For comparison, the image obtained using the exact value of the gradient is shown in FIG. 48 and is seen to be free of any oscillating distortions. Clearly the degree of distortion increases as the gradient deviates increasingly from the value calculated using equation [A 10.1].

What is claimed is:

1. A method of imaging an object undergoing continuous translational motion through a magnetic field by acquiring nuclear magnetic resonance signals therefrom comprising the steps of:

conveying the object to be analyzed through an imaging module at a predetermined velocity, v;

generating, within the imaging module, a spatially characterised constant magnetic field B0;

generating, within the imaging module, a spatially characterised, temporally constant magnetic field gradient, Gz substantially parallel to the direction of the velocity, v;

generating, within the imaging module, a radiofrequency field B1 pulse traverse to field B0;

detecting nuclear magnetic resonance signals weighted with at least one selected nuclear magnetic resonance parameter from said object, said generating steps and said detecting step occurring during a period in which said object is moving at said predetermined velocity; and correcting said signal for a motional phase factor acquired from the movement of said object at said predetermined velocity through said spatially characterised fields.

2. The method according to claim 1 wherein said step of generating said constant magnetic field $B_0$ comprises generating said field substantially parallel to the direction of the velocity, v.

3. The method according to claim 1 wherein said detecting step comprises detecting a free induction decay signal from the object passing through the imaging module motionally modified by the object's translational motion.

4. The method according to claim 1 wherein said detecting step comprises detecting the spin echo or gradient echo of the object passing through the imaging module motionally modified by the object's translational motion.

5. The method according to claim 1 in which the spatially characterized constant magnetic field $B_0$ is substantially spatially uniform.

6. The method according claim 1 in which the spatially characterized magnetic field gradient $G_z$ is substantially linear.

7. The method according to claim 1 further including the step of providing said $B_0$, $B_1$ and $G_z$ fields as spatially homogenous fields over a module length, in the direction of v, of at least v×AQ where AQ is the data acquisition time required to determine the magnetic resonance measurements.

8. The method according to claim 7 wherein the $B_0$, $B_1$ and $G_z$ fields are provided as spatially homogeneous fields over a module length, in the direction of v, of at least 4v×AQ.

9. The method according to claim 1 wherein the step of generating the radio frequency field pulse $B_1$ includes the step of triggering a first pulse with reference to arrival of the object in the module.

10. The method according to claim 9 further including the step of determining the timing of successive RF pulses $B_1$ according to a real time determination of the object velocity v.

11. The method according to claim 1 further including the step of determining the magnitude of $G_z$ according to the equation $2\pi n/AQ.L$ rad sec$^{-1}$ cm$^{-1}$ where n=the number of points in the image over the length L of the object to be imaged and AQ=the acquisition time.

12. The method according to claim 1 further including the step of inducing a longitudinal magnetization in the object parallel or antiparallel to its direction of movement prior to its entry into the imaging module.

13. The method according to claim 12 in which the step of inducing longitudinal magnetisation in the object comprises the step of passing the object through a polarizing module, for a predetermined time period, the polarizing module providing a magnetic field parallel to the direction of movement of the object.

14. The method according to claim 13 in which the predetermined time period is at least 5×$T_1$, where $T_1$ is the longitudinal relaxation time.

15. The method according to claim 1 further including the step of substantially preventing rotational movement of the object.

16. The method according to claim 1 further including the step of substantially preventing the movement of the object in any direction transverse to the predetermined velocity, v.

17. The method according to claim 1 in which the object element of a fluid being conveyed through the imaging module.

18. The method according to claim 3 further including the steps of correcting the motional modification of the free induction decay signal to remove the phase factor introduced by the motion and generating a one-dimensional image projection of the object from the acquired corrected free induction decay signal.

19. The method according to claim 18 in which:

the spatially characterised constant magnetic field $B_0$ is substantially spatially uniform;

the spatially characterised magnetic field gradient $G_z$ is substantially linear; and wherein the step of generating a one-dimensional image projection comprises the steps of:

transformation of the signal, in the time domain, by multiplication with the factor $\exp\{-i\gamma G.vt^2/2\}$;

adjusting the phase to give a zero first point in the imaginary part of the signal;

reflecting the signal using its complex conjugate; and performing a Fourier transform thereon.

20. The method according to claim 3 in which the step of generating the radiofrequency field further comprises the step of generating a spin echo pulse sequence 90-$_\iota$-(180-$_\iota$)$_n$, where $\iota$ is the pulse spacing and n is an integer$\geq$1 and wherein the $B_0$, $B_1$ and Gz fields are provided as spatially homogeneous fields over a module length, in the direction of v, of at least 4v×AQ.

21. The method according to claim 1 further including the steps of: detecting a free induction decay signal from the object passing through the imaging module motionally modified by the object's translational motion; correcting the motional modification of the free induction decay signal to remove the phase factor introduced by the motion and generating a one-dimensional image projection of the object from the acquired corrected free induction signal, and weighting said image with a further nuclear magnetic resonance parameter.

22. The method according to claim 21 wherein said further parameter is one or more of $T_2^*$, $T_2$, $T_1$, D or flow velocity, where $T_2^*$ is the transverse spin dephasing time in the field gradient $G_z$; $T_2$ is the transverse relaxation time; $T_1$ is the longitudinal relaxation time; and D is the self-diffusion coefficient.

23. The method of claim 22 wherein said further parameter is $T_1$ and wherein said RF pulse generating step includes inversion of the polarized magnetisation of the object by said $B_0$ field by a hard 180° pulse followed by recovery for a predetermined time, $t_1$, prior to said transverse RF pulse.

24. The method of claim 22 wherein said further parameter is D, further including the step of generating, within the imaging module, a spatially localised, non-uniform magnetic field gradient $G_x$ substantially transverse to $B_0$.

25. The method of claim 22 flier including the step of generating, within the imaging module, at least one additional linear magnetic field gradient $G_\phi$ transverse to $B_0$.

26. The method of claim 21 further including the steps of generating at least one further one-dimensional image projection of the object from the acquired motionally modified free induction decay signal, and weighting said image with a second further nuclear magnetic resonance parameter.

27. Apparatus for gathering nuclear magnetic resonance imaging data comprising:
a first field generating means for generating a spatially characterised, constant magnetic field $B_0$ in an imaging unit volume having a redetermined length along a longitudinal axis thereof, the $B_0$ field being substantially parallel to said longitudinal axis;
a second field generating means for generating, in said imaging unit volume, a spatially characterised magnetic field gradient $G_z$ substantially parallel to $B_0$, and comprising a coil having adjacent loops thereof separated by a distance which increases as a function of the distance along the coil axis;
a third field generating means for generating, within the imaging unit volume, radiofrequency field $B_1$ pulses transverse to field $B_0$, and comprising a cylindrical coil having a first series of loops in which the plane of each loop is tilted with respect to the cylinder axis so as to generate a field with a component perpendicular to the cylinder axis, and a second series of loops which generate a field which substantially eliminates a longitudinal component of the field generated by the first series of loops;
receiver means for detecting nuclear magnetic resonance signals weighted with at least one selected nuclear magnetic resonance parameter from said object;
wherein said first, second and third field generating means are all constructed to have mutually coaxial cylindrical geometry which construction can be generally extendable to an arbitrary length along said longitudinal axis.

28. Apparatus according to claim 27 wherein said third field generating means comprises a pair of coaxial coils, a first of said pair of coils having each loop occupy a plane substantially orthogonal to the axis of said coil and the second of said pair of coils having each loop occupy a plane tilted with respect to the planes of the loops of the first of said pair of coils.

29. Apparatus according to claim 27 in which said first, second and third field generating means each have a cylindrical geometry coaxial with one another.

30. Apparatus according to claim 27 in which the spatially characterized constant magnetic field $B_0$ is substantially spatially uniform and the spatially characterized magnetic field gradient $G_z$ is substantially linear.

31. Apparatus according to claim 27 in which said first field generating means comprises a hollow cylindrical permanent magnet.

32. Apparatus for gathering nuclear magnetic resonance imaging data comprising:
a first field generating means for generating a spatially characterised, constant magnetic field $B_0$ in an imaging unit volume having a predetermined length along a longitudinal axis thereof, the $B_0$ field being parallel to said longitudinal axis;
a second field generating means for generating, in said imaging unit volume, a spatially characterised magnetic field gradient $G_z$ substantially parallel to $B_0$;
a third field generating means for generating, within the imaging unit volume, radiofrequency field $B_1$ pulses transverse to field $B_0$;
receiver means for detecting nuclear magnetic resonance signals weighted with at least one selected nuclear magnetic resonance parameter from said object;
wherein at least said second field generating means comprises a coil in which each successive adjacent loop along the longitudinal axis is separated from a preceding loop by a distance which increases along the longitudinal axis.

33. Apparatus according to claim 32 wherein said third field generating means comprises a pair of coaxial coils, a first of said pair of coils having each loop occupy a plane substantially orthogonal to the axis of said coil and the second of said pair of coils having each loop occupy a plane tilted with respect to the planes of the loops of the first of said pair of coils.

34. Apparatus according to claim 32 in which said first, second and third field generating means each have a cylindrical geometry coaxial with one another.

35. Apparatus according to claim 32 in which the spatially characterized constant magnetic field $B_0$ is substantially spatially uniform and the spatially characterized magnetic field gradient $G_z$, is substantially linear.

36. Apparatus according to claim 32 in which said first field generating means comprises a hollow cylindrical permanent magnet.

37. Apparatus for gathering nuclear magnetic resonance data for imaging comprising:
a first field generating means for generating a spatially characterised, constant magnetic field $B_0$, in an imaging unit volume having a predetermined length along a longitudinal axis thereof;
conveyance means for conveying an object under analysis through said imaging unit volume at a predetermined velocity substantially along said longitudinal axis thereof;
a second field generating means for generating, in said imaging unit volume, a spatially characterised, temporally constant magnetic field gradient $G_z$ substantially parallel to the longitudinal axis;
a third field generating means for generating, within the imaging unit volume, radiofrequency field $B_1$ pulses transverse to field $B_0$;
receiver means for detecting nuclear magnetic resonance signals weighted with at least one selected nuclear magnetic resonance parameter from said object during a period in which said object is moving through said imaging unit volume at said predetermined velocity; and means for correcting said detected signals for a motional phase factor acquired from the movement of said object at said predetermined velocity through the imaging volume.

38. Apparatus according to claim 37 wherein said third field generating means comprises a pair of coaxial coils, a first of said pair of coils having each loop occupy a plane substantially orthogonal to the axis of said coil and the second of said pair of coils having each loop occupy a plane tilted with respect to the planes of the loops of the first of said pair of coils.

39. Apparatus according to claim 37 in which said first, second and third field generating means each have a cylindrical geometry coaxial with one another.

40. Apparatus according to claim 37 in which the spatially characterized constant magnetic field $B_0$ is substantially spatially uniform and the spatially characterized magnetic field gradient $G_z$, is substantially linear.

41. Apparatus according to claim 37 in which said first field generating means comprises a hollow cylindrical permanent magnet.

* * * * *